US008790656B2

(12) United States Patent
Meulenberg et al.

(10) Patent No.: US 8,790,656 B2
(45) **Date of Patent: *Jul. 29, 2014**

(54) PRRSV VACCINES

(75) Inventors: Johanna Jacoba Maria Meulenberg, Amsterdam (NL); Monique Helene Verheije, Dronten (NL)

(73) Assignee: Boehringer Ingelheim Vetmedica GmbH, Ingelheim am Rhein (DE)

(*) Notice: Subject to any disclaimer, the term of this patent is extended or adjusted under 35 U.S.C. 154(b) by 163 days.

This patent is subject to a terminal disclaimer.

(21) Appl. No.: 11/422,970

(22) Filed: Jun. 8, 2006

(65) Prior Publication Data

US 2006/0240041 A1 Oct. 26, 2006

Related U.S. Application Data

(63) Continuation of application No. 09/948,747, filed on Sep. 7, 2001, now abandoned, which is a continuation-in-part of application No. 09/874,626, filed on Jun. 5, 2001, now abandoned, and a continuation of application No. PCT/NL00/00152, filed on Mar. 8, 2000, said application No. 09/874,626 is a continuation of application No. 09/297,535, filed as application No. PCT/NL97/00593 on Oct. 29, 1997, now Pat. No. 6,268,199.

(30) Foreign Application Priority Data

| | | |
|---|---|---|
| Oct. 30, 1996 | (EP) | 96203024 |
| Mar. 8, 1999 | (EP) | 99200668 |

(51) Int. Cl.

| | |
|---|---|
| ***C12N 15/86*** | (2006.01) |
| ***A61K 39/12*** | (2006.01) |
| ***C07K 14/005*** | (2006.01) |
| ***C12N 7/00*** | (2006.01) |
| *A61K 39/00* | (2006.01) |

(52) U.S. Cl.

CPC .............. *C07K 14/005* (2013.01); *C12N 15/86* (2013.01); *C12N 2770/10034* (2013.01); *C12N 2770/10022* (2013.01); *C12N 2770/10043* (2013.01); *A61K 2039/5256* (2013.01); *A61K 2039/51* (2013.01); *C12N 2770/10061* (2013.01); *C12N 7/00* (2013.01); *A61K 39/00* (2013.01)

USPC .................. 424/204.1; 424/199.1; 424/218.1; 435/320.1

(58) Field of Classification Search

None

See application file for complete search history.

(56) References Cited

U.S. PATENT DOCUMENTS

| | | | | |
|---|---|---|---|---|
| 3,080,291 A | | 3/1963 | Sinha et al. | |
| 3,137,631 A | | 6/1964 | Soloway | |
| 3,959,457 A | | 5/1976 | Speaker et al. | |
| 4,015,100 A | | 3/1977 | Gnanamuthu et al. | |
| 4,122,167 A | | 10/1978 | Buynak et al. | |
| 4,205,060 A | | 5/1980 | Monsimer et al. | |
| 4,224,412 A | | 9/1980 | Dorofeev et al. | |
| 4,452,747 A | | 6/1984 | Gersonde et al. | |
| 4,468,346 A | | 8/1984 | Paul et al. | |
| 4,554,159 A | | 11/1985 | Roizman et al. | |
| 4,606,940 A | | 8/1986 | Frank et al. | |
| 4,636,485 A | | 1/1987 | van der Smissen | |
| 4,744,933 A | | 5/1988 | Rha et al. | |
| 4,753,884 A | | 6/1988 | Kit et al. | |
| 4,810,493 A | | 3/1989 | Patrick et al. | |
| 4,921,706 A | | 5/1990 | Roberts et al. | |
| 4,927,637 A | | 5/1990 | Morano et al. | |
| 4,944,948 A | | 7/1990 | Uster et al. | |
| 5,008,050 A | | 4/1991 | Cullis et al. | |
| 5,009,956 A | | 4/1991 | Baumann | |
| 5,132,117 A | | 7/1992 | Speaker et al. | |
| 5,206,163 A | | 4/1993 | Renard et al. | |
| 5,213,759 A | | 5/1993 | Castberg et al. | |
| 5,419,907 A | | 5/1995 | Paul et al. | |
| 5,476,778 A | | 12/1995 | Chladek et al. | |
| 5,510,258 A | | 4/1996 | Sanderson et al. | |
| 5,587,164 A | | 12/1996 | Sanderson et al. | |
| 5,597,721 A | | 1/1997 | Brun et al. | |
| 5,620,691 A | * | 4/1997 | Wensvoort et al. | 424/184.1 |
| 5,674,500 A | | 10/1997 | Peeters et al. | |
| 5,677,429 A | | 10/1997 | Benfield | |
| 5,683,865 A | | 11/1997 | Collins et al. | |
| 5,690,940 A | | 11/1997 | Joo | |

(Continued)

FOREIGN PATENT DOCUMENTS

| | | |
|---|---|---|
| CA | 2103460 A1 | 12/1992 |
| DE | 145705 A1 | 1/1981 |

(Continued)

OTHER PUBLICATIONS

Moormann et al. J Virology 1996, vol. 70, pp. 763-770.*
Zhou et al. PNAS 1995, vol. 92, pp. 3009-3013.*
Dea et al. J. Clin. Microbiol. 1996 vol. 34, pp. 1488-14.*

(Continued)

*Primary Examiner* — Mary E Mosher
*Assistant Examiner* — Myron Hill
(74) *Attorney, Agent, or Firm* — Michael P. Morris; Joyce L. Morrison

(57) ABSTRACT

The invention relates to the field of PRRS viruses and infectious clones obtained from PRRS viruses. Furthermore, the invention relates to vaccines and diagnostic assays obtainable by using and modifying such infectious clones of PRRS viruses. The invention provides a porcine reproductive and respiratory syndrome virus (PRRSV) replicon having at least some of its original PRRSV nucleic acid deleted, said replicon capable of in vivo RNA replication, said replicon further having been deprived of at least some of its original PRRSV nucleic acid and/or having been supplemented with nucleic acid derived from a heterologous microorganism.

14 Claims, 4 Drawing Sheets

(56) References Cited

U.S. PATENT DOCUMENTS

Figure 1:
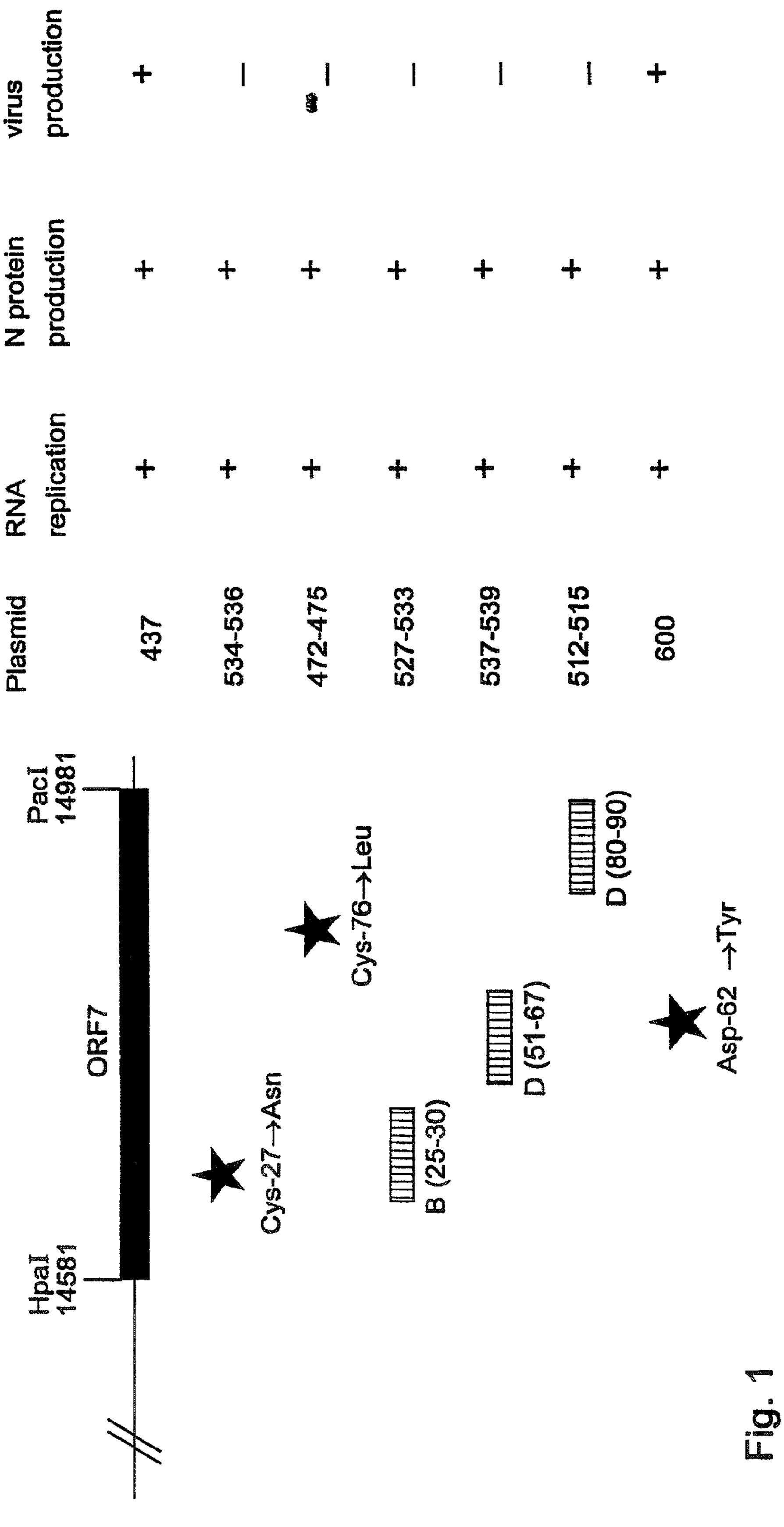

| | | | |
|---|---|---|---|
| 5,695,766 | A | 12/1997 | Paul et al. |
| 5,698,203 | A | 12/1997 | Visser et al. |
| 5,789,388 | A | 8/1998 | Visser et al. |
| 5,840,563 | A | 11/1998 | Chladek et al. |
| 5,846,805 | A | 12/1998 | Collins et al. |
| 5,858,729 | A | 1/1999 | Van Woensel et al. |
| 5,866,401 | A | 2/1999 | Hesse |
| 5,888,513 | A | 3/1999 | Plana Duran et al. |
| 5,910,310 | A | 6/1999 | Heinen et al. |
| 5,925,359 | A | 7/1999 | Van Woensel et al. |
| 5,968,525 | A | 10/1999 | Fitzgerald et al. |
| 5,976,537 | A | 11/1999 | Mengeling et al. |
| 5,989,563 | A | 11/1999 | Chladek et al. |
| 5,998,601 | A | 12/1999 | Murtaugh et al. |
| 6,001,370 | A | 12/1999 | Burch et al. |
| 6,015,663 | A | 1/2000 | Wesley et al. |
| 6,042,830 | A | 3/2000 | Chladek et al. |
| 6,080,570 | A | 6/2000 | Chladek et al. |
| 6,110,467 | A | 8/2000 | Paul et al. |
| 6,110,468 | A | 8/2000 | Collins et al. |
| 6,197,310 | B1 | 3/2001 | Wensvoort et al. |
| 6,241,990 | B1 | 6/2001 | Collins et al. |
| 6,251,397 | B1 | 6/2001 | Paul et al. |
| 6,251,404 | B1 | 6/2001 | Paul et al. |
| 6,268,199 | B1 * | 7/2001 | Meulenberg et al. ...... 435/235.1 |
| 6,380,376 | B1 | 4/2002 | Paul et al. |
| 6,391,314 | B1 | 5/2002 | Allan et al. |
| 6,455,245 | B1 | 9/2002 | Wensvoort et al. |
| 6,495,138 | B1 | 12/2002 | van Nieuwstadt et al. |
| 6,498,008 | B2 | 12/2002 | Collins et al. |
| 6,500,662 | B1 | 12/2002 | Calvert et al. |
| 6,592,873 | B1 | 7/2003 | Paul et al. |
| 6,641,819 | B2 | 11/2003 | Mengeling et al. |
| 6,660,513 | B2 | 12/2003 | Mengeling et al. |
| 6,773,908 | B1 | 8/2004 | Paul et al. |
| 6,806,086 | B2 | 10/2004 | Wensvoort et al. |
| 6,841,364 | B2 | 1/2005 | Yuan et al. |
| 6,855,315 | B2 | 2/2005 | Collins et al. |
| 6,982,160 | B2 | 1/2006 | Collins et al. |
| 7,018,638 | B2 | 3/2006 | Chu et al. |
| 7,081,342 | B2 | 7/2006 | Mengeling et al. |
| 7,109,025 | B1 | 9/2006 | Eloit et al. |
| 7,122,347 | B2 | 10/2006 | Verheije et al. |
| 7,132,106 | B2 | 11/2006 | Calvert et al. |
| 7,169,394 | B2 | 1/2007 | Chu et al. |
| 7,211,379 | B2 | 5/2007 | Ellis et al. |
| 7,232,680 | B2 | 6/2007 | Calvert et al. |
| 7,264,804 | B2 | 9/2007 | Collins et al. |
| 7,273,617 | B2 | 9/2007 | Yuan et al. |
| 7,312,030 | B2 | 12/2007 | van Rijn et al. |
| 7,335,361 | B2 | 2/2008 | Liao et al. |
| 7,335,473 | B2 | 2/2008 | Wensvoort et al. |
| 7,368,117 | B2 | 5/2008 | Fetzer et al. |
| 7,618,797 | B2 | 11/2009 | Calvert et al. |
| 7,632,636 | B2 | 12/2009 | Roof et al. |
| 7,691,389 | B2 | 4/2010 | Calvert et al. |
| 7,722,878 | B2 | 5/2010 | Vaughn et al. |
| 7,897,343 | B2 | 3/2011 | Wensvoort et al. |
| 2002/0012670 | A1 | 1/2002 | Elbers et al. |
| 2002/0098573 | A1 | 7/2002 | Meulenberg et al. |
| 2002/0172690 | A1 | 11/2002 | Calvert et al. |
| 2003/0049274 | A1 | 3/2003 | Meulenberg et al. |
| 2003/0118608 | A1 | 6/2003 | Wensvoort et al. |
| 2003/0157689 | A1 | 8/2003 | Calvert et al. |
| 2003/0219732 | A1 | 11/2003 | van Rijn et al. |
| 2004/0009190 | A1 | 1/2004 | Elbers et al. |
| 2004/0132014 | A1 | 7/2004 | Wensvoort et al. |
| 2004/0197872 | A1 | 10/2004 | Meulenberg et al. |
| 2004/0213805 | A1 | 10/2004 | Verheije |
| 2004/0224327 | A1 | 11/2004 | Meulenberg et al. |
| 2004/0253270 | A1 | 12/2004 | Meng et al. |
| 2006/0063151 | A1 | 3/2006 | Roof et al. |
| 2006/0205033 | A1 | 9/2006 | Meulenberg et al. |
| 2006/0240041 | A1 | 10/2006 | Meulenberg et al. |
| 2006/0286123 | A1 | 12/2006 | Fetzer et al. |
| 2007/0003570 | A1 | 1/2007 | Murtaugh et al. |
| 2007/0042000 | A1 | 2/2007 | Mengeling et al. |
| 2009/0148474 | A1 | 6/2009 | Roof et al. |
| 2010/0003278 | A1 | 1/2010 | Roof et al. |
| 2010/0028860 | A1 | 2/2010 | Roof et al. |
| 2010/0129398 | A1 | 5/2010 | Klinge et al. |
| 2011/0104201 | A1 | 5/2011 | Mengeling et al. |
| 2011/0117129 | A1 | 5/2011 | Roof et al. |
| 2011/0195088 | A1 | 8/2011 | Roof et al. |
| 2012/0189655 | A1 | 7/2012 | Wu et al. |

FOREIGN PATENT DOCUMENTS

| | | | |
|---|---|---|---|
| EP | 208672 | A1 | 1/1987 |
| EP | 0440219 | A1 | 8/1991 |
| EP | 0529584 | A2 | 3/1993 |
| EP | 587780 | A1 | 3/1994 |
| EP | 0 595 436 | A2 | 5/1994 |
| EP | 0610250 | A1 | 8/1994 |
| EP | 676467 | A2 | 10/1995 |
| EP | 0 732 340 | A2 | 9/1996 |
| EP | 0 835 930 | A1 | 4/1998 |
| EP | 0835929 | A1 | 4/1998 |
| EP | 0 839 912 | A1 | 5/1998 |
| EP | 1018557 | A2 | 7/2000 |
| FR | 2602791 | A1 | 2/1988 |
| GB | 2282811 | A | 4/1995 |
| GB | 2289279 | A | 11/1995 |
| JP | 62/198626 | A | 9/1987 |
| WO | 8803410 | A1 | 5/1988 |
| WO | 8908701 | A1 | 9/1989 |
| WO | 9221375 | A1 | 12/1992 |
| WO | 9303760 | A1 | 3/1993 |
| WO | 93/06211 | A1 | 4/1993 |
| WO | 93/07898 | A1 | 4/1993 |
| WO | 93/14196 | A1 | 7/1993 |
| WO | 94/18311 | | 8/1994 |
| WO | 94/18311 | A1 | 8/1994 |
| WO | 95/28227 | A1 | 10/1995 |
| WO | 9531550 | A1 | 11/1995 |
| WO | 9604010 | A1 | 2/1996 |
| WO | 9606619 | A1 | 3/1996 |
| WO | 96/36356 | A1 | 11/1996 |
| WO | 96/40932 | A1 | 12/1996 |
| WO | 97/00696 | | 1/1997 |
| WO | 97/31651 | A1 | 9/1997 |
| WO | 9731652 | A1 | 9/1997 |
| WO | 9818933 | A1 | 5/1998 |
| WO | 9835023 | A1 | 8/1998 |
| WO | 98/50426 | A1 | 11/1998 |
| WO | WO98/50426 | * | 11/1998 |
| WO | 98/55625 | | 12/1998 |
| WO | 9855626 | A2 | 12/1998 |
| WO | 00/53787 | A1 | 9/2000 |
| WO | 0065032 | A1 | 11/2000 |
| WO | 0159077 | A1 | 8/2001 |
| WO | 0190363 | A1 | 11/2001 |
| WO | 02/095040 | A1 | 11/2002 |
| WO | 03062407 | A1 | 7/2003 |
| WO | 2006002193 | A2 | 1/2006 |
| WO | 2006034319 | A2 | 3/2006 |
| WO | 2006074986 | A2 | 7/2006 |
| WO | 2007064742 | A2 | 6/2007 |
| WO | 2008109237 | A2 | 9/2008 |
| WO | 2008121958 | A1 | 10/2008 |
| WO | 2010025109 | A1 | 3/2010 |
| WO | 2011128415 | A1 | 10/2011 |

OTHER PUBLICATIONS

Allende, R. et al., North American and European Porcine Reproductive and Respiratory Syndrome Viruses Differ in Non-Structural Protein Coding Regins, Journal Gen. Virol. 80 (Pt 2), 307-315 (1999).

Andreyev VG., et al. Abstract, Genetic variation and phylogenetic relationships of 22 porcine reproductive and respiratory syndrome virus (PRRSV) fields strains based on sequence analysis of open reading frame 5, Arch Virol 142:993-1001, 1997.

Bramel-Verheije et al., Expression of a Foreign Epitope by Porcine Reproductive and Respiratory Syndrome Virus, 2000, Virology, pp. 380-389, vol. 278.

(56) References Cited

OTHER PUBLICATIONS

Kapur, V., et al., Abstract, Genetic Variation in Porcine reproductive and Respiratory Syndrome Virus Isolates in the Midwestern United States, Journal of Gen. Virol. 77, pp. 1271-1276 (1996).
Kim HS., et al., Abstract, Enhanced replication of porcine reproductive and respiratory syndrome (PRRS) virus in a homogeneous subpopulation of MA-104 cell line, Arch Virol. 133:477-483, 1993.
Kreutz, L.C., Abstract, "Cellular membrane factors are the major determinants of porcine reproductive and respiratory syndrome virus tropism," Virus Research 53 : 12 1-128, 1998.
Kwang, Jimmy, et al., Abstract, Cloning, Expression, and Sequence Analysis of the OrF4 Gene of the Porcine Reproductive and Respiratory Syndrome Virus MN-1b, J Vet Diagn. Invest 6, pp. 293-296 (1994).
Mardassi, H., et al., Abstract, Molecular Analysis of the OW'S 3 to 7 of Porcine Reproductive and Respiratory Syndrome Virus, Quebec Reference Strain, Arch Virol 140, pp. 1405-1418 (1995).
Meng, Xiang-Jin, Abstract, Molecular Cloning and Nucleotide Sequencing of the 3'-Terminal Genomic RNA of the Porcine Reproductive and Respiratory Syndrome Virus, Journal of General Virology 75, pp. 1795-1801 (1994).
Meulenberg, J.J.M., et al., Abstract, "An infectious cDNA clone of Porcine Reproductive and Respiratory Syndrome Virus" Chapter 24, pp. 199-206 Coronaviruses and Arteriviruses (Advances in Experimental Medicine and Biology, vol. 440), 1998.
Meng XJ., et al., Abstract, Phylogenetic analyses of the putative M (OW 6) and N (OW 7) genes of porcine reproductive and respiratory syndrome virus (PRRSV): implication for the existence of two genotypes of PRRSV in the U.S.A. and Europe, Arch Virol 140:745-755, 1995.
Morozovi., et al., Abstract, Sequence analysis of open reading frames (ORFs) 2 to 4 of a U.S. isolate of porcine reproductive and respiratory syndrome virus, Arch Virol 140: 13 13-1319,1995.
Murtaugh, M. P., et al., Abstract, Comparison of the Structural Protein Coding Sequences of the VR-2332 and Lelystad virus strain of the PRRS virus, Journal Arch. Virol. 140(8), pp. 145 1-1460 (1995).
Nelsen, C. J., et al., Porcine reproductive and respiratory syndrome virus comparison: Divergent evolution on two continents. J. Virol. 73 (1): pp. 270-280, 1999.
Rossow KD., Abstract, Porcine Reproductive and Respiratory Syndrome, Vet Pathol. 35: 1-20 (1998).
Suarez P., et al., Abstract, Phylogenetic relationships of European strains of porcine reproductive and respiratory syndrome virus (PRRSV) inferred from DNA sequences of putative ORF-5 and ORF-7 genes, Virus Research 42: 159-1 65, 1996.
Terpstra C., et al., Abstract, Experimental reproduction of porcine epidemic abortion and respiratory syndrome (mystery swine disease) by infection with Lelystad virus: Koch's postulates fulfilled, The Veterinary Quarterly, vol. 13, No. 3, pp. 13 1-1 36, Jul. 1991.
Van Dinten, L.D. et al., 1997, Proc. Natl. Acad. Sci. USA, 94(3):991-996.
Zimmerman JJ., et al., Abstract, General overview of PRRSV: A perspective from the United States, Veterinary Microbiology 55 : 187-1 96, 1997.
PCT International Preliminary Examination Report, PCT/NL02/003 14, dated Aug. 26, 2003, 6 pages.
VIIIth International Symposium on Nidoviruses (Corona and Arteriviruses), May 20-25, 2000.
NC-00 196 1, Porcine reproductive and respiratory syndrome virus, complete genome.
NO66 183, Porcine reproductive and respiratory syndrome virus RespPRRS MLV, complete genome.
AF325691, Porcine reproductive and respiratory syndrome virus isolate NVSL 97-7985 IA 1-4-2, complete genome.
AF176348, Porcine reproductive and respiratory syndrome virus isolate PA8 complete genome.
AF33 183 1, Procine reproductive and respiratory syndrome virus BJ-4, complete genome.
AE005 172, *Arabidopsis thaliana* chromosome 1, top arm complete sequence.
NC-002534, Lactate dehydrogenase-elevating virus, complete genome.
U87392, Porcine reproductive and respiratory syndrome virus strain VR-2332, complete genome.
M96262, Lelystad virus, complete genome.
AF184212, Porcine reproductive and respiratory syndrome virus strain SP, complete genome.
AF 159 149, Porcine reproductive and respiratory syndrome virus isolate MLV RespPRRSIRepro, complete genome.
AF046869, Porcine reproductive and respiratory syndrome virus isolate 16244B, 211 Aug. 1997 (Nebraska)pass.3, complete genome.
U15 146, Lactate dehydrogenase-elevating virus Plagemann strain, complete genome.
Mengeling et al., Mystery Pig Disease: Evidence and considerations for its etiology, In: Proceedings of the Mystery Swine Disease Committee Meeting, Oct. 6, 1990, Denver, Colorado, Livestock Conservation Institute, Madison, WI, USA.
Rottier et al., Predicted membrane topology of the coronavirus protein E1, Biochemistry, 1986, pp. 1335 1339, vol. 25.
Sethna et al., Coronavirus subgenomic minus-strand RNAs and the potential for mRNA replicons, Proc. Natl. Acad. Sci. 1989, USA, pp. 5626 5630, vol. 86.
Spaan et al., Coronaviruses: structure and genome expression, J. Gen. Virol., 1988, pp. 2939 2952, vol. 69.
Vries et al., All subgenomic mRNAs of equine arteritis virus contain a common leader sequence, Nucleic Acids Res., 1990, pp. 3241-3247, vol. 18.
U.S. Appl. No. 09/874,626, filed Jun. 5, 2001 (Abandoned).
U.S. Appl. No. 10/226,065, filed Aug. 21, 2002 now U.S. Patent No. 6,806,086 issued Oct. 19, 2002.
U.S. Appl. No. 11/966,036, filed Dec. 28, 2007 (Pending).
U.S. Appl. No. 10/737,658, filed Dec. 16, 2007 (Pending).
U.S. Appl. No. 10/300,699, filed Nov. 19, 2002 now U.S. Patent No. 7,122,344 issued Oct. 17, 2006.
U.S. Appl. No. 10/407,822, filed Apr. 4, 2003 now U.S. Patent No. 7,312,030 issued Dec. 25, 2007.
U.S. Appl. No. 10/891,444, filed Jul. 14, 2004 now U.S. Patent No. 7,335,473 issued Mar. 17, 2005.
U.S. Appl. No. 11/949,769, filed Dec. 4, 2007 (Pending).
U.S. Appl. No. 10/737,658, filed Dec. 16, 2003 (Abandoned).
U.S. Appl. No. 10/745,949, filed Dec. 23, 2003 (Abandoned).
U.S. Appl. No. 10/750,410, filed Dec. 30, 2003 (Pending).
U.S. Appl. No. 10/750,409, filed Dec. 30, 2003 (Pending).
U.S. Appl. No. 11/239,529, filed Sep. 29, 2005 (Pending).
U.S. Appl. No. 11/422,970, filed Aug. 6, 2006 (Pending).
Verheije et al., J. Virol., 76:1521-1526 (2002).
Wesley et al., "Differentiation of a porcine reproductive and respiratory syndrome virus vaccine strain from North American field strains by restrction fragment length polymorphism analysis of ORF 5". Journal of Veterinary Diagnostic Investigation, vol. 10, 1998, pp. 140-144.
"Dutch Team Isolates Mystery Pig Disease Agent", Animal Pharm, vol. 230, Abstract No. 00278268, Jun. 21, 1991, p. 21.
"For purification of viral RNA from Plasma, Serum, Cell-free body fluids, Cell-Culture supernatants". QIAamp® Viral RNA Mini Kit Handbook, Qiagen, Jan. 1999, Cat #52906, pp. 1-35.
"Frontiers closing to mystery disease pigs". Animal Pharm., No. 228, May 24, 1991, p. 2.
"Revision of the taxonomy of the Coronavirus, Torovirus, and Arterivirus genera". Archives of Virology, vol. 135, 1994, pp. 227-239.
Abstracts of Papers Presented at the 71st Annual Meeting of the Conference of Research Workers in Animal Disease, Nos. 1-6, Nov. 5-6, 1990, 2 pages.
Aksenova et al., "Cultivation of the rabies virus in the continuous kidney cell line 4647 from the green marmoset". Vopr. Virusol., vol. 30, No. 2, 1985, pp. 180-182. (See Axenova for English Abstract).
Albina et al., "Immune responses in pigs infected with porcine reproductive and respiratory syndrome virus (PRRSV)". Veterinary Immunology and Immunopathology, vol. 61, 1998, pp. 49-66.
Allan et al., "Experimental infection of colostrum deprived piglets with porcine circovirus 2 (PCV2) and procine reproductive and res-

(56) References Cited

OTHER PUBLICATIONS piratory syndrome virus (PRRSV) potentiates PCV2 replication". 2000, Archives of Virology, vol. 145, pp. 2421-2429.
Allende et al., "Mutations in the genome of porcine reproductive and respiratory syndrome virus responsible for the attenuated phenotype". Archives of Virology, vol. 145, No. 6, Jun. 2000, pp. 1149-1161.
Altschul et al., "Basic Local Alignment Search Tool". Journal of Molecular Biology, vol. 215, 1990, pp. 403-410.
Ashworth et al., "Antibody-dependent cell-mediated cytotoxicity (ADCC) in Aujeszky's disease". Archives of Virology, vol. 59, No. 4, 1979, pp. 307-318.
Axenova, T.A. "Propagation of Rabies Vaccine Virus in Continuous Green Monkey Kidney Cells 4647". Vopr. Virusol., vol. 30, No. 2, 1985, p. 182. (English Abstract of Aksenova Reference.).
Backstrom et al., "Respiratory Diseases of Swine". Veterinary Clinics of North America: Large Animal Practice, vol. 4, No. 2, Nov. 1982, pp. 259-276.
Barfoed et al., "DNA vaccination of pigs with open reading frame 1-7 of PRRS virus". Vaccine, vol. 22, 2004, pp. 3628-3641.
Baric et al., "Interactions between Coronavirus Nucleocapsid Protein and Viral RNAs: Implications for Viral Transcription". Journal of Virology, vol. 62, No. 11, Nov. 1988, pp. 4280-4287.
Baric et al., "Subgenomic Negative-Strand RNA Function during Mouse Hepatitis Virus Infection". Journal of Virology, vol. 74, No. 9, May 2000, pp. 4039-4046.
Bautista et al., "Comparison of Porcine Alveolar Macrophages and CL 2621 for the Detection of Porcine Reproductive and Respiratory Syndrome (PRRS) Virus and Anti-PRRS Antibody". Journal of Veterinary Diagnostic Investigation, vol. 5, No. 2, Apr. 1993, pp. 163-165.
Bautista et al., "Serologic Survey for Lelystad and VR-2332 Strains of Porcine Respiratory and Reproductive Syndrome (PRRS) Virus in US Swine Herds". Journal of Veterinary Diagnostic Investigation, vol. 5, No. 4, Oct. 1992, pp. 612-614.
Beale, AJ, "Vaccines and antiviral drugs". Principles of bacteriology, virology and immunity, vol. 3, Ch. 86, 1984, pp. 147-161.
Beare et al., "Further Studies in Man of Man of HSw1N1 Influenza Viruses". Journal of Medical Virology, vol. 5, 1980, pp. 33-38.
Beghi et al., "Guillain-Barré Syndrome: Clinicoepidemiologic Features and Effect of Influenza Vaccine". Archives of Neurology, vol. 42, No. 11, 1985, pp. 1053-1057.
Benfield et al., "Characterization of swine infertility and respiratory syndrome (SIRS) virus (isolate ATCC VR-2332)". Journal of Veterinary Diagnostic Investigation, vol. 4, 1992, pp. 127-133.
Benfield et al., "Etiologic Agent of Swine Infertility and Respiratory Syndrome in the United States". 72st Annual Meeting of the Conference of Research Workers in Animal Disease, Chicago, IL, Nov. 11-12, 1991, p. 48, Abstract No. 268.
Benfield et al., "Properties of SIRS Virus Isolate ATCC VR-2332 in the United States and Preliminary Characterization of a Monoclonal Antibody to this Virus". American Association of Swine Practitioners Newsletter, vol. 4, No. 4, Jul./Aug. 1992, pp. 19-21.
Berendt et al., "Evaluation of Commercially Prepared Vaccines for Experimentally Induced Type/A/New Jersey/8/76 Influenza Virus Infections in Mice and Squirrel Monkeys". The Journal of Infectious Diseases, vol. 136, Dec. 1977, pp. S712-S718.
Berendt et al., "Reaction of Squirrel Monkeys to Intratracheal Inoculation with Influenza/A/New Jersey/76 (Swine) Virus". Infection and Immunity, vol. 16, No. 2, May 1977, pp. 476-479.
Bilodeau et al., "'Porcine Reproductive and Respiratory Syndrome' in Quebec". The Veterinary Record, Aug. 3, 1991, p. 102.
Blackburn et al., "Use of human influenza vaccine to protect against blue-eared pig disease". Veterinary Record, vol. 129, No. 1, Jul. 1991, p. 19.
Bohl et al., "Isolation and Serotyping of Porcine Rotaviruses and Antigenic Comparison with Other Rotaviruses". Journal of Clinical Microbiology, vol. 19, No. 2, Feb. 1984, pp. 105-111.
Bouillant et al., "Viral Susceptibility of a Cell Line Derived from the Pig Oviduct". Canadian Journal of Comparative Medicine, vol. 39, 1975, pp. 450-456.
Boursnell et al., "Sequence of the membrane protein gene from avian coronavirus IBV". Virus Research, vol. 1, 1984, pp. 303-313.
Boursnell et all., "Completion of the Sequence of the Genome of the Coronavirus Avian Infectious Bronchitis Virus". Journal of General Virology, vol. 68, 1987, pp. 57-77.
Bowie et al., "Deciphering the Message of Protein Sequences: Tolerance to Amino Acid Substitutions". Science, vol. 247, 1990, pp. 1306-1310.
Boyer et al., "Infectious Transcripts and cDNA Clones of RNA Viruses". Virology, vol. 198, No. 2, Feb. 1994, pp. 415-426.
Bredenbeek et al., "The primary structure and expression of the second open reading frame of the polymerase gene of the coronavirus MHV-A59; a highly conserved polymerase is expressed by an efficient ribosomal frameshifting mechanism". Nucleic Acids Research, vol. 18, No. 7, 1990, pp. 1825-1832.
Brenner et al., "A Negative Staining Method for High Resolution Electron Microscopy of Viruses". Biochimica Et Biophysica Acta, vol. 34, 1959, pp. 103-110.
Brinton-Darnell et al., "Structure and chemical-physical characteristics of lactate dehydrogenase-elevating virus and its RNA". Journal of Virology, vol. 16, No. 2, Aug. 1975, pp. 420-433.
Brinton-Darnell, M. "Lactate Dehydrogenase-Elevating, Equine Arteritis and Lelystad Viruses". Encyclopedia of Virology, vol. 2, 1999, pp. 763-771.
Bruner, D.W., "Table XXXXII. Characteristics of Viral Respiratory Infections in Swine" Hagan's Infectious Diseases of Domestic Animals: With Special Reference to Etiology, Diagnosis, and Biologic Therapy, Sixth Edition, Comstock Publishing Associations, a division of Cornell University Press, Ithaca and London, 1973, 5 pages.
Brüggemann et al., "Immunoglobulin V region variants in hybridoma cells. I. Isolation of a variant with altered idiotypic and antigen binding specificity". The EMBO Journal, vol. 1, No. 5, 1982, pp. 629-634.
Buck, K. W., "Comparison of the Replication of Positive-Stranded RNA Viruses of Plants and Animals". Advances in Virus Research, vol. 47, 1996, pp. 159-251.
Burgess et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue". The Journal of Cell Biology, vol. 111, 1990, pp. 2129-2138.
Burroughs, et al., "Relationship of San Miguel Sea Lion Virus to Other Members of the Calicivirus Group". Intervirology, vol. 10, 1978, pp. 51-59.
Cabasso et al., "Propagation of Infectious Canine Hepatitis Virus in Tissue Culture". Proceedings of the Society for Experimental Biology and Medicine, vol. 85, 1954, pp. 239-245.
Caeiro et al., "In vitro DNA replication by cytoplasmic extracts from cells infected with African swine fever virus". Virology, vol. 179, No. 1, Nov. 1990, pp. 87-94.
Callebaut et al., "Antigenic Differentiation between Transmissible Gastroenteritis Virus of Swine and a Related Porcine Respiratory Coronavirus". Journal of General Virology, vol. 69, 1988, pp. 1725-1730.
Carrascosa et al., "Relationship of San Miguel Sea Lion Virus to Other Members of the Calicivirus Group". Journal of Virological Methods, vol. 3, No. 6, Jan. 1982, pp. 303-310.
Carvajal et al., "Evaluation of a Blocking ELISA Using Monoclonal Antibodies for the Detection of Porcine Epidemic Diarrhea Virus and Its Antibodies". Journal of Veterinary Diagnostic Investigation, vol. 7, No. 1, Jan. 1995, pp. 60-64.
Cavanagh, D., "Nidovirales: a new order comprising Coronaviridae and Arteriviridae". Archives of Virology, vol. 142, No. 3, 1997, pp. 629-633.
Chang et al., "A cis-Acting Function for the Coronavirus Leader in Defective Interfering RNA Replication". Journal of Virology, vol. 68, No. 12, Dec. 1994, pp. 8223-8231.
Von Busse, F.W., Epidemiologic Studies on Porcine Reproductive and Respiratory Syndrome (PRRS). Tierarztliche Umschau, Dec. 1991, pp. 708-717 (Abstract in English p. 711).

(56) References Cited

OTHER PUBLICATIONS

Von Ohlinger et al., "Der Seuchenhafte Spatabort beim Schwein Ein Beitrag zur Atiologie des Porcine Reproductive and Respiratory Syndrome (PRRS)". Tierarztl, vol. 46, 1991, pp. 703-708.
Waltner-Toews et al., "A Field Trial to Evaluate the Efficacy of a Combined Rotavirus-Coronavirus/ *Escherichia coli* vaccine in Dairy Cattle"., Canadian Journal of Comparative Medicine, vol. 49, No. 1, 1985, pp. 1-9.
Wang et al., "Attenuation of porcine reproductive and respiratory syndrome virus strain MN184 using chimeric construction with vaccine sequence". Virology, vol. 371, 2008, pp. 418-429.
Ward et al., "Efficiency of human rotavirus propagation in cell culture". Journal of Clinical Microbiology, vol. 19, No. 6, Jun. 1984, pp. 748-753.
Wardley et al., "The Host Response to African Swine Fever Virus". Progress of Medical Virology, vol. 34, 1987, pp. 180-192.
Wassenaar et al., "Alternative Proteolytic Processing of the Arterivirus Replicase ORF1a Polyprotein: Evidence that NSP2 Acts as a Cofactor for the NSP4 Serine Protease". Journal of Virology, vol. 71, No. 12, Dec. 1997, pp. 9313-9322.
Webster et al., "Chemotherapy and Vaccination: a Possible Strategy for the Control of Highly Virulent Influenza Virus". Journal of Virology, vol. 55, No. 1, 1985, pp. 173-176.
Welch et al., "Construction and evaluation of genetically engineered replication-defective porcine reproductive and respiratory syndrome virus vaccine candidates". Veterinary Immunology and Immunopathology, vol. 102, 2004, pp. 277-290.
Wensvoort et al., "'Blue ear' disease in pigs". Veterinary Record, vol. 128, No. 24, Jun. 1991, p. 574.
Wensvoort et al., "'Lelystad agent'—the cause of abortus blauw (mystery swine disease)". Tijdschr Diergeneeskd, vol. 116, No. 13, Jul. 1991, pp. 675-676.
Wensvoort et al., "An Enzyme Immunoassay Employing Monoclonal Antibodies and Detecting Specifically Antibodies to Classical Swine Fever Virus". Veterinary Microbiology, vol. 17, 1988, pp. 129-140.
Wensvoort et al., "Antigenic Comparison of Lelystad Virus and Swine Infertility and Respiratory Syndrome (SIRS) Virus". Journal of Veterinary Diagnostic Investigation, vol. 4, 1992, pp. 134-138.
Wensvoort et al., "Bovine viral diarrhoea virus infections in piglets born to sows vaccinated against swine fever with contaminated vaccine". Research in Veterinary Science, vol. 45, 1988, pp. 143-148.
Wensvoort et al., "Characterization of Porcine and Some Ruminant Pestiviruses by Cross-neutralization" vol. 20, 1989, pp. 291-306.
Wensvoort et al., "Lelystad virus, the cause of porcine epidemic abortion and respiratory syndrome: a review of mystery swine disease research in Lelystad". Veterinary Microbiology, vol. 33, Nos. 1-4, Nov. 1992, pp. 185-193.
Wensvoort et al., "Mystery Swine Disease in the Netherlands the Isolation of Lelystad Virus". The Veterinary Quarterly, vol. 13, No. 3, 1991, pp. 121-130.
Wensvoort et al., "Production of Monoclonal Antibodies Against Swine Fever Virus and Their Use in Laboratory Diagnosis". Veterinary Microbiology, vol. 12, 1986, pp. 101-108.
Wensvoort et al., "The Porcine Reproductive and Respiratory Syndrome; Characteristics and diagnosis of the causative virus". Veterinary Biotechnology Newsletter, vol. 3, 1993, pp. 113-120.
Wesley et al., "Differentiation of vaccine (strain RespPRRS) and field strains of porcine reproductive and respiratory syndrome virus by restriction enzyme analysis". Proceedings of the American Association on Swine Practitioners, Nashville, TN, USA, 1996, pp. 141-143.
Westenbrink et al., "An enzyme-linked immunosorbent assay for detection of antibodies to porcine parvovirus". Journal of Virological Methods, vol. 23, 1989, pp. 169-178.
Wieczorek-Krohmer et al., "Porcine reproductive and respiratory syndrome virus (PRRSV): Monoclonal antibodies detect common epitopes on two viral proteins of European and U.S. isolates". Veterinary Microbiology, vol. 51, Nos. 3-4, Aug. 1996, pp. 257-266.
Witte, K.H. "The Situation of 'Epidemic Late Abortion of Swine' in the State of Northrhine-Westphalia". Workshop Seminar, Apr. 1991.
Woode, et al., "Porcine Rotavirus Infection". Diseases of Swine, Fifth Edition, Chapter 26, The Iowa State University Press, Ames, Iowa, 1981, pp. 310-322.
Woods et al., "Antigenicity of Inactivated Swine Influenza Virus Concentrated by Centrifugation". Research Communications in Chemical Pathology and Pharmacology, vol. 13, No. 1, 1976, pp. 129-132.
Woods et al., "Experimental challenge of pregnant gilts with swine influenza virus after vaccination". Research Communications in Chemical Pathology and Pharmacology, vol. 15, No. 4, Dec. 1976, pp. 787-795.
Woods et al., "Investigation of Four Outbreaks of Acute Respiratory Disease in Swine and Isolation of Swine Influenza Virus". Health Laboratory Science, vol. 5, No. 4, Oct. 1968, pp. 218-224.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, pp. 37-38.
Yamane et al., "Annual Examination of Influenza Virus Infection Among Pigs in Miyagi Prefecture, Japan: The Appearance of Hsw1N1 Virus". Acta Virologica, vol. 23, 1979, pp. 240-248.
Yang et al., "Comparative sequence analysis of open reading frames 2 to 7 of the modified live vaccine virus and other North American isolates of the porcine reproductive and respiratory syndrome virus". Archives of Virology, vol. 143, 1998, pp. 601-612.
Yoon et al., "A modified serum neutralization test for the detection of antibody to porcine reproductive and respiratory syndrome virus in swine sera". Journal of Veterinary Diagnostic Investigation, vol. 6, No. 3, Jul. 1994, pp. 289-292.
Yoon et al., "Failure to Consider the Antigenic Diversity of Porcine Reproductive and Respiratory Syndrome (PRRS) Virus Isolates May Lead to Misdiagnosis". Journal of Veterinary Diagnostic Investigation, vol. 7, Jul. 1995, pp. 386-387.
Yoon et al., "Isolation of a Cytopathic Virus from Weak Pigs on Farms with a History of Swine Infertility and Respiratory Syndrome". Journal of Veterinary Diagnostic Investigation, vol. 4, Apr. 1992, pp. 139-143.
Yu et al., "Specific Binding of Host Cellular Proteins to Multiple Sites within the 39 End of Mouse Hepatitis Virus Genomic RNA". Journal of Virology, vol. 69, No. 4, Apr. 1995, pp. 2016-2023.
Yuan et al., "Complete genome comparison of porcine reproductive and respiratory syndrome virus parental and attenuated strains". Virus Research, vol. 74, 2001, pp. 99-110.
Yuan et al., "Erratum to 'Complete genome comparison of porcine reproductive and respiratory syndrome virus parental and attenuated strains' [Virus Research 74 (2001) 99-110]". Virus Research, vol. 79, 2001, p. 187.
Yuan et al., "Molecular characterization of a highly pathogenic strain of PRRSV associated with porcine High Fever syndrome in China". 2007 International Porcine Reproductive and Respiratory Syndrome (PRRS) Symposium, Chicago, Illinois, Nov.-Dec. 2007, Poster 70.
Yuan et al., American Society for Virology, 16th Annual Meeting, Bozeman, Montana, Jul. 19-23, 1997, Abstract P29-5, p. 229.
Zeijst, et al., "The Genome of Equine Arteritis Virus". Virology, vol. 68, 1975, pp. 418-425.
Easterday, B.C., "Swine Influenza". Diseases of Swine, Sixth Edition, Iowa State University Press, 1986, pp. 244-315. (Part Two of Two—pp. 286-315). This NPL is too large for EFS submission. Therefore filing in two parts.
Easterday, et al., "Swine Influenza". In Diseases of Swine (8th Edition), BE Straw, S D'Allaire, WI. Mengeling, DJ Taylor, eds., Ames: Iowa State University Press, 1999, pp. 277-290.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, pp. 5227-5232.
Ehresmann et al., "RNA synthesized in calicivirus-infected cells is atypical of picornaviruses". Journal of Virology, vol. 22, No. 2, May 1977, pp. 572-576.
Ellis, R.W., "New Technologies for Making Vaccines". Vaccines, Chapter 29, Plotkin et al Eds., WB Saunders Company, Philadelphia, PA 1988, pp. 568-575.

(56) References Cited

OTHER PUBLICATIONS

Enjuanes et al., "Isolation and Properties of the DNA of African Swine Fever (ASF) Virus". Journal of General Virology, vol. 32, No. 3, Sep. 1976, pp. 479-492.
*Enzo Biochem Inc*. v. *Gen-Probe Incorporated et al*., No. 01-01230; Decided Jul. 15, 2002.
Estes et al., "Simian rotavirus SA11 replication in cell cultures". Journal of Virology, vol. 31, No. 3, Sep. 1979, pp. 810-815.
Fang et al., "Heterogeneity in nsp2 of European-like porcine reproductive and respiratory syndrome viruses isolated in the United States". Virus Research, vol. 100, 2004, pp. 229-235.
Fenner et al., "Immunization against Viral Diseases", Veterinary Virology, Ch. 14, 1992, pp. 265-271.
Fenner et al., "Viral Genetics and Evolution", Veterinary Virology, Ch. 5, 1992, pp. 89-95.
Ferrari et al., "Isolation of Cytopathic Strains of Rotavirus from Pigs". Microbiologica, vol. 9, No. 3, Jul. 1986, pp. 287-294.
Flint et al., "Virus Cultivation, Detection, and Genetics". Virology, Molecular Biology, Pathogenesis, and Control, Ch. 2, 2000, pp. 40-42.
Foss et al., "Adjuvant Danger Signals Increase the Immune Response to Porcine Reproductive and Respiratory Syndrome Virus". Viral Immunology, vol. 15, No. 4, 2002, pp. 557-566.
Frolov et al., "Alphavirus-based expression vectors: Strategies and applications". Proceedings of the National Academy of Sciences, vol. 93, Oct. 1996, pp. 11371-11377.
Fu et al., "Detection and survival of group A rotavirus in a piggery". Veterinary Record, vol. 125, 1989, pp. 576-578.
Fukuhara et al., "Evidence for endocytosis-independent infection by human rotavirus". Archives of Virology, vol. 97, Nos. 1-2, 1987, pp. 93-99.
Funkhouser et al., "Mutations in the 5'-noncoding, 2C and P3 Regions of the Genome Increase the Efficiency of Hepatitis A Virus Growth in MRC-5 Cells". Vaccines, vol. 94, Cold Springs Harbor Laboratory Press, 1994, pp. 345-349.
Garwes, D.J., "Transmissible gastroenteritis". Veterinary Record, vol. 122, 1988, pp. 462-463.
Geisbert et al., "Use of Immunoelectron Microscopy to Show Ebola Virus During the 1989 United States Epizootic". Journal of Clinical Pathology, vol. 43, No. 10, Oct. 1990, pp. 813-816.
Girard et al., "Experimentally induced porcine proliferative and necrotising pneumonia with an influenza A virus". The Veterinary Record, vol. 130, Mar. 1992, pp. 206-207.
Godeny et al., "Map location of lactate dehydrogenase-elevating virus (LDV) capsid protein (Vpl) gene", Virology, vol. 177, No. 2, Aug. 1990, pp. 768-771.
Godeny et al., "The 3' Terminus of Lactate Dehydrogenase-Elevating Virus Genome RNA Does Not Contain Togavirus or Flavivirus Conserved Sequences", Virology, vol. 72, 1989, pp. 647-650.
Goldfield et al., "Influenza in New Jersey in 1976: Isolations of Influenza A/New Jersey/76 Virus at Fort Dix". The Journal of Infectious Diseases, vol. 136, Supp. 3, 1977, pp. S347-S355.
Goldstein, et al., "Evaluation of Three Cell Culture Systems as Substrates for Influenza Virus Assay". Applied Microbiology, vol. 19, No. 4, Apr. 1970, pp. 580-582.
Gong et al., "Characterization of RNA synthesis during a one-step growth curve and of the replication mechanism of bovine viral diarrhoea virus". Journal of General Virology, vol. 77, 1996, pp. 2729-2736.
Gorcyca et al., RespPRRS: A new tool for the prevention and control of PRRS in pigs. Proceedings of the American Association of Swine Practitioners, Omaha, Nebraska, Mar. 1995, pp. 1-22.
Gourreau et al., "Diffusion du virus de la grippe du porc (H1N1=Hsw1N1) en France". Annales de l'Institut Pasteur/ Virologie, vol. 132, No. 2, Apr.-Jun. 1981, pp. 287-294.
Goyal, S., "Porcine Reproductive and Respiratory Syndrome", Journal of Veterinary Diagnostic Investigation, vol. 5, No. 4, 1993, pp. 656-664.
Gravell et al., "Differences among isolates of simian hemorrhagic fever (SHF) virus". Proceedings of the Society for Experimental Biology and Medicine, vol. 181, No. 1, 1986, pp. 112-119.
Graves, J.H., "Swine Vesicular Disease". Diseases of Swine, Fifth Edition, Chapter 23, The Iowa State University Press, Ames, Iowa, 1958, pp. 288-293.
Grebennikova et al., "Genomic characterization of virulent, attenuated, and revertant passages of a North American porcine reproductive and respiratory syndrome virus strain". Virology, vol. 321, 2004, pp. 383-390.
Greiner et al., "Quantitative relationship of systemic virus concentration on growth and immune response in pigs". Journal of Animal Science, vol. 78, 2000, pp. 2690-2695.
Grizzard et al., "Experimental production of respiratory tract disease in cebus monkeys after intratracheal or intranasal infection with influenza A/Victoria/3/75 or influenza A/New Jersey/76 virus". Infection and Immunity, vol. 21, No. 1, Jul. 1978, pp. 201-205.
Grouse, L.D., "Swine Flue Sequelae"., Journal of the American Medical Association, vol. 243, No. 24, 1980, p. 2489.
Grunert et al., "Sensitivity of Influenza A/New Jersey/8/76 (HswlNI) Virus to Amantadine-HCI". Journal of Infectious Diseases, vol. 136, No. 2, 1977, pp. 297-300.
Guan et al., "Requirement of a 5?-Proximal Linear Sequence on Minus Strands for Plus-Strand Synthesis of a Satellite RNA Associated with Turnip Crinkle Virus". Virology, vol. 268, No. 2, Mar. 2000, pp. 355-363.
Gubler et al., "A simple and very efficient method for generating cDNA libraries". Gene, vol. 25, 1983, pp. 263-269.
Gustafson, D.P., "Pseudorabies". Diseases of Swine, Fifth Edition, Ch. 14, The Iowa State University Press, Ames, Iowa, 1981, pp. 209-223.
Halbur et al., "Comparative pathogenicity of nine US porcine reproductive and respiratory syndrome virus (PRRSV) isolates in a five-week-old cesarean-derived, colostrum-deprived pig model". Journal of Veterinary Diagnostic Investigation, vol. 8, 1996, pp. 11-20.
Halbur et al., "Effects of different US isolates of porcine reproductive and respiratory syndrome virus (PRRSV) on blood and bone marrow parameters of experimentally infected pigs". Veterinary Record, vol. 151, 2002, pp. 344-348.
Halbur et al., "Variable Pathogenicity of Nine Porcine Reproductive and Respiratory Syndrome Virus (PRRSV) Isolates". Conference of Research Workers in Animal Diseases, Abstracts of Papers, Chicago, Illinois, paper #222, Nov. 1993.
Halbur et al., "Viral Pneumonia in Neonatal and Nursery pigs. Experimental Work with SIRS Agent and Evidence of Another New Viral Agent". Agri-Practice, vol. 12, No. 1, Jan.-Feb. 1991, pp. 23-34.
Hao et al., "Polymorphic genetic characterization of the ORF7 gene of porcine reproductive and respiratory syndrome virus (PRRSV) in China". Virology Journal, vol. 8:73, pp. 1-9.
Harlow & Lane, Editors, "Antibodies, A Laboratory Manual". Cold Spring Harbor: Cold Spring Harbor Laboratory, New York, 1988, pp. 423, 464-468.
Haynes et al., "Temporal and Morphologic Characterization of the Distribution of Porcine Reproductive and Respiratory Syndrome Virus (PRRSV) by In Situ Hybridization in Pigs Infected with Isolates of PRRSV that Differ in Virulence". Veterinary Pathology, vol. 34, 1997, pp. 39-43.
Heath, et al., "The Behaviour of Some Influenza Viruses in Tissue Cultures of Kidney Cells of Various Species". Archie. f. Virusforschung Bd. VIII HS, 1958, pp. 577-591.
Hedger et al., "Swine Vesicular Disease Virus". Virus Infections of Porcines, Elsevier Science Publishers, B.V., 1989, pp. 241-250.
Hennen, J., "Statistical methods for longitudinal research on bipolar disorders". Bipolar Disorders, vol. 5, 2003, pp. 156-168.
Hill, Howard, "Overview and History of Mystery Swine". Proceedings of the Mystery Swine Disease Committee Meeting, Denver, CO, Oct. 6, 1990, pp. 29-40.
Pejsak et al., "Clinical signs and economic losses caused by porcine reproductive and respiratory syndrome virus in a large breeding farm". Veterinary Microbiology, vol. 44, 1997, pp. 317-322.
Peng et al., "Analysis of Second-Site Revertants of a Murine Coronavirus Nucleocapsid Protein Deletion Mutant and Construc-

(56) References Cited

OTHER PUBLICATIONS tion of Nucleocapsid Protein Mutants by Targeted RNA Recombination". Journal of Virology, vol. 69, No. 6, Jun. 1995, pp. 3449-3457.
Penzes et al., "Characterization of a Replicating and Packaged Defective RNA of Avian Coronavirus Infectious Bronchitis Virus". vol. 203, No. 2, Sep. 1994, pp. 286-293.
Percy et al., "Expression of a Foreign Protein by Influenza A Virus". Journal of Virology, vol. 68, No. 7, Jul. 1994, pp. 4486-4492.
Pirtle et al., "Morphologic Heterogeneity of a Strain of Swine Influenza Virus (A/Swine/Wisconsin/1/68, Hsw1N1) Propagated at Different Temperatures". American Journal of Veterinary Research, vol. 36, No. 1, 1975, pp. 1783-1787.
Plagemann et al., "Lactate Dehydrogenase-Elevating Virus, Equine Arteritis Virus, and Simina Hemorrhagic Fever Virus: A New Group of Positive-Strand RNA Viruses". Advances in Virus Research, vol. 41, 1991, pp. 99-192.
Pol et al., "Pathological, ultrastructural, immunohistochemical changes caused by Lelystad virus in experimentally induced infections of mystery swine disease (synonym: porcine epidemic abortion and respiratory syndrome (PEARS)". Veterinary Quarterly, vol. 13, No. 3, Jul. 1991, pp. 137-143.
Polson et al., "An evaluation of the financial impact of Porcine Reproductive and Respiratory Syndrome (PRRS) in nursery pigs". Proceedings of the 13th International Pig Veterinary Society Congress, Jun. 1994, p. 31.
Polson et al., "Financial Implications of Mystery Swine Disease (MSD)". 1993, pp. 8-28.
Polson, DD, "Answers to Your Questions on PRRS". NOBL Laboratories, 1993, 18 Pages.
Polson, DD, "RespPRRS a PRRS Vaccine Review", NOBL Laboratories, 1993, 22 pages.
Porcine Reproductive and Respiratory Syndrome: A Report on the Seminar Held in Brussels on Nov. 4-5, 1991 and Organized by the European Commission.
Poser, C.M., "Swine Influenza Vaccination: Truth and Consequences". Archives of Neurology, vol. 42, No. 11, 1985, pp. 1090-1092.
Potgieter et al., "Isolation of Swine Influenza Virus in Oklahoma". Journal of the American Veterinary Medical Association, vol. 171, No. 8, 1977, pp. 758-760.
Potts et al., "Peroxidase-labeled primary antibody method for detection of pestivirus contamination in cell cultures". Journal of Virological Methods, vol. 26, No. 1, Oct. 1989, pp. 119-124.
Quaife, T. "Mystery Agent Isolated! Isolation of the etiological agent behind mystery swine disease is a major breakthrough". Swine Practitioner, Mystery Disease: Part 8, Nov. 1991, pp. 4-7.
Reed et al., "A Simple Method of Estimating Fifty Per Cent Endpoints"., The American Journal of Hygiene, vol. 27, No. 3, May 1938, pp. 493-497.
Reed et al., "Persistent Respiratory Virus Infection in Tracheal Organ Cultures". British Journal of Experimental Pathology, vol. 50, 1969, pp. 378-388.
Response to Opposition to European Patent No. 0 587 780, Aug. 30, 1996.
Rice et al., "Production of Infectious RNA Transcripts from Sindbis Virus cDNA Clones: Mapping of Lethal Mutations, Rescue of a Temperature-Sensitive Marker, and In Vitro Mutagenesis to Generate Defined Mutants". Journal of Virology, vol. 61, No. 12, Dec. 1987, pp. 3809-3819.
Roberts et al., "Abortion in Swine". Veterinary Ostetrics and Genital Diseases, Edwards Brothers, Inc., Ann Arbor, 1986, pp. 180-192.
Roof et al., "Efficacy of Modified Live Virus Porcine Reproductive and Respiratory Virus Vaccines Against Heterologous Respiratory Challenge". 4th International Symposium on Emerging and Re-emerging Pig Diseases, Rome, Jun. 28-Jul. 2, 2003, pp. 117-118.
Ropp et al., "Characterization of Emerging European-Like Porcine Reproductive and Respiratory Syndrome Virus Isolates in the United States"., Journal of Virology, vol. 78, No. 7, Apr. 2004, pp. 3684-3703.
Rossow et al., "Experimental porcine reproductive and respiratory syndrome virus infection in one-, four-, and 10-week-old pigs". Journal of Veterinary Diagnostic Investigation, vol. 6, 1993, pp. 3-12.
Roth et al., "Influenza virus hemagglutinin expression is polarized in cells infected with recombinant SV40 viruses carrying cloned hemagglutinin DNA". Cell, vol. 33, No. 2, Jun. 1983, pp. 435-443.
Roth et al., "The large external domain is sufficient for the correct sorting of secreted or chimeric influenza virus hemagglutinins in polarized monkey kidney cells". The Journal of Cell Biology, vol. 104, Mar. 1987, pp. 769-782.
Rovira et al., "Experimental Inoculation of Conventional Pigs with Porcine Reproductive and Respiratory Syndrome virus and Porcine Circovirus 2", J. Virol, jApr. 2002, vol. 76, no. 7, pp. 3232-3239.
Sagripanti et al., "The Cap Structure of Simian Hemorrhagic Fever Virion RNA". Virology, vol. 151, 1986, pp. 143-150.
Saif et al., "Serial propagation of porcine group C rotavirus (pararotavirus) in a continuous cell line and characterization of the passaged virus". Journal of Clinical Microbiology, vol. 26, No. 7, Jul. 1988, pp. 1277-1282.
Saif, L.J., "Coronavirus Immunogens". Veterinary Microbiology, vol. 37, No. 3-4, Nov. 1993, pp. 285-297.
Sarnow, P. "Role of 3'-End Sequences in Infectivity of Poliovirus Transcripts Made In Vitro". Journal of Virology, vol. 63, No. 1, Jan. 1989, pp. 467-470.
Sawicki et al., "Coronavirus Transcription: Subgenomic Mouse Hepatitis Virus Replicative Intermediates Function in RNA Synthesis". Journal of Virology, vol. 64, No. 3, Mar. 1990, pp. 1050-1056.
Schmidt et al., "Infection of Influenza A Viruses of Tracheal Organ Cultures Derived from Homologous and Heterologous Hosts". The Journal of Infectious Diseases, vol. 129, No. 1, 1974, pp. 28-36.
Scott, F.W., "Immunization against feline coronaviruses". Advances in Experimental Medicine and Biology, vol. 218, 1987, pp. 569-576.
Seal et al., "Analysis of the Serologic Relationship among San Miguel Sea Lion Virus and Vesicular Exanthema of Swine Virus Isolates. Application of the Western Blot Assay for Detection of Antibodies in Swine Sera to these Virus Types". Journal of Veterinary Diagnostic Investigation, vol. 7, No. 2, Apr. 1995, pp. 190-195.
Seal et al., "Isolation of caliciviruses from skunks that are antigenically and genotypically related to San Miguel sea lion virus Original Research". Virus Research, vol. 37, No. 1, Jun. 1995, pp. 1-12.
Seneca, H., "Influenza: epidemiology, etiology, immunization and management". Journal of American Geriatrics Society, vol. 28, No. 6, Jun. 1980, pp. 241-250.
Setzer et al., "Size Heterogeneity in the 3' End of Dihydrofolate Reductase Messenger RNAs in Mouse Cells". Cell, vol. 22, Nov. 1980, pp. 361-370.
Shaw et al., "Experimental rotavirus infection in three-week-old pigs". American Journal of Veterinary Research, vol. 50, No. 11, Nov. 1989, pp. 1961-1965.
Shen et al., "Determination of the complete nucleotide sequence of a vaccine strain of porcine reproductive and respiratory syndrome virus and identification of the Nsp2 gene with a unique insertion". Archives of Virology, vol. 145, No. 5, May 2000, pp. 871-883.
Shibata et al., "Detection of Human Papilloma Virus in Paraffin-Embedded Tissue Using the Polymerase Chain Reaction". The Journal of Experimental Medicine, vol. 167, No. 1, Jan. 1988, pp. 225-230.
Shieh et al., "The 5'-End Sequence of the Murine Coronavirus Genome: Implications of Multiple Fusion Sites in Leader-Primed Transcription". Virology, vol. 156, 1987, pp. 321-330.
Shin et al., "Assessment of Porcine Reproductive and Respiratory Syndrome Virus RNA Load in Sera and Tissues during Acute Infection". Journal of Veterinary Science, vol. 3, No. 2, 2002, pp. 75-85.
Shope et al., "The Susceptibility of Swine to the Virus of Human Influenza". Annual Meeting of the Society of American Bacteriologists in New York, 1936, pp. 791-801.
Shortridge et al., "Geographical Distribution of Swine (HSw1N1) and Hong Kong (H3N2) Influenza Virus Variants in Pigs in Southeast Asia". Intervirology, vol. 11, No. 1, 1979, pp. 9-15.
Skiadopoulos et al., "Identification of Mutations Contributing to the Temperature-Sensitive, Cold-Adapted, and Attenuation Phenotypes of the Live-Attenuated Cold-Passage 45 (cp45) Human

(56) References Cited

OTHER PUBLICATIONS

Parainfluenza Virus 3 Candidate Vaccine". Journal of Virology, vol. 73, No. 2, Feb. 1999, pp. 1374-1381.
Smith et al., "Isolation of Swine Influenza Virus from Autopsy Lung Tissue of Man". New England Journal of Medicine, vol. 294, Mar. 1976, pp. 708-710.
Smith et al., "San Miguel Sea Lion Virus Isolation, Preliminary Characterization and Relationship to Vesicular Exanthema of Swine Virus". Nature, vol. 244, Jul. 1973, pp. 108-110.
Snijder et al., "A 3'-Coterminal Nested Set of Independently Transcribed mRNAs Is Generated during Berne Virus Replication". Journal of Virology, vol. 64, No. 1, Jan. 1990, pp. 331-338.
Snijder et al., "Identification of a Novel Structural Protein of Arteriviruses". Journal of Virology, vol. 73, No. 8, Aug. 1999, pp. 6335-6345.
Snijder et al., "Non-structural proteins 2 and 3 interact to modify host cell membranes during the formation of the arterivirus replication complex". Journal of General Virology, vol. 83, 2001, pp. 985-994.
Snijder et al., "Proteolytic Processing of the Replicase ORF1a Protein of Equine Arteritis Virus". Journal of Virology, vol. 68, No. 9, Sep. 1994, pp. 5755-5764.
Snijder et al., "The carboxyl-terminal part of the putative Berne virus polymerase is expressed by ribosomal frameshifting and contains sequence motifs which indicate that toro- and coronaviruses are evolutionarily related". Nucleic Acids Research, vol. 18, No. 15, Aug. 1990, pp. 4535-4542.
Snijder et al., "The molecular biology of arteriviruses". Journal of General Virology, vol. 79, 1998, pp. 961-979.
Snijder et al., "Toroviruses: replication, evolution and comparison with other members of the coronavirus-like superfamily". Journal of General Virology, vol. 74, 1993, pp. 2305-2316.
Stephen et al., "Swine Influenza Virus Vaccine: Potentiation in Rhesus Monkeys in Antibody Responses by a Nuclease Resistant Derivative of Ply I-Poly C". U.S. Army Medical Research Institute of Infectious Diseases, Fort Detrick, Frederick, MD 21701, 1976, 10 pages.
Stephen et al., "Swine influenza virus vaccine: potentiation of antibody responses in rhesus monkeys". Science, vol. 197, No. 4310, 1977, pp. 1289-1290.
Stevenson et al., "Endemic Porcine Reproductive and Respiratory Syndrome Virus Infection of Nursery Pigs in Two Swine Herds without Current Reproductive Failure". Journal of Veterinary Diagnostic Investigation, vol. 5, 1993, pp. 432-434.
Stim, T.B., "Arbovirus Plaquing in Two Simian Kidney Cell Lines". Journal of General Virology, vol. 5, No. 3, Oct. 1969, pp. 329-338.
Suarez et al., "Direct detection of the porcine reproductive and respiratory syndrome (PRRS) virus by reverse polymerase chain reaction (RT-PCR)". Archives of Virology, vol. 135, No. 1-2, 1994, pp. 89-99.
Sumiyoshi et al., "Infectious Japanese Encephalitis Virus RNA Can Be Synthesized from In Vitro-Ligated cDNA Templates". Journal of Virology, vol. 66, No. 9, Sep. 1992, pp. 5425-5431.
Tahara et al., "Coronavirus Translational Regulation: Leader Affects mRNA Efficiency". Virology, vol. 202, No. 1, Aug. 1994, pp. 621-630.
Tao et al., "Host Range Restriction of Parainfluenza Virus Growth Occurs at the Level of Virus Genome Replication". Virology, vol. 220, 1996, pp. 69-77.
Tauraso et al., "Simian Hemorrhagic Fever: III. Characterization of a Viral Agent". The American Journal of Tropical Medicine and Hygiene, vol. 17, No. 3, May 1968, pp. 422-431.
Thacker, B., "Clinical Manifestations of PRRS Virus". 2003 PRRS Compendium: Second Edition, National Pork Board, Des Moines, IA, 2003, pp. 7-15.
Thanawongnuwech et al., "Effects of Low (Modified-live Virus Vaccine) and High (VR-2385)-Virulence Strains of Porcine Reproductive and Respiratory Syndrome Virus on Pulmonary Clearance of Copper Particles in Pigs". Veterinary Pathology, vol. 35, 1998, pp. 398-406.
Theil et al., "Isolation and Serial Propagation of Turkey Rotaviruses in a Fetal Rhesus Monkey Kidney (MA104) Cell Line". Avian Diseases, vol. 30, No. 1, 1985, pp. 93-104.
Theil et al., "Partial characterization of a bovine group A rotavirus with a short genome electropherotype". Journal of Clinical Microbiology, vol. 26, No. 6, Jun. 1988, p. 1094-1099.
Thomson et al., "Ontario. Proliferative and necrotizing pneumonia (PNP) of swine: the Ontario situation". Canadian Veterinary Journal, vol. 32, May 1991, p. 313.
Thouless et al., "Isolation of two lapine rotaviruses: Characterization of their subgroup, serotype and RNA electropherotypes". Archives of Virology, vol. 89, Nos. 1-4, 1986, pp. 161-170.
Tian et al., "Emergence of Fatal PRRSV Variants: Unparalleled Outbreaks of Atypical PRRS in China and Molecular Dissection of the Unique Hallmark". PLoS One, vol. 2, No. 6, e526, 2007, pp. 1-10.
Timony, P.J. "Equine Viral Arteritis", Manual of Standards for Diagnostic Tests and Vaccines, 1992, pp. 493-500.
Tizard et al., (no citation available) cited by the Examiner in U.S. Appl. No. 08/017,961, (filed Feb. 12, 1993; now abandoned).
Tobita et al., "Plaque Assay and Primary Isolation of influenza A Viruses in an Established Line of Canine Kidney Cells (MDCK) in the Presence of Trypsin". Medical Microbiology and Immunology, vol. 162, No. 1, Dec. 1975, pp. 9-14.
Todd et al., "Development of an adjuvant-active nonionic block copolymer for use in oil-free subunit vaccines formulations". Vaccine, vol. 15, No. 5, 1997, pp. 564-570.
Travassos et al., "Carajas and Maraba Viruses, Two New Vesiculoviruses Isolated from Phlebotomine Sand Flies in Brazil". American Journal of Tropical Medicine and Hygiene, vol. 33, No. 5, Sep. 1984, pp. 999-1006.
Tsunemitsu et al., "Isolation, characterization, and serial propagation of a bovine group C rotavirus in a monkey kidney cell line (MA104)". Journal of Clinical Microbiology, vol. 29, No. 11, Nov. 1991, pp. 2609-2613.
Ulmer et al., "Enhancement of DNA vaccine potency using conventional aluminum adjuvants". Vaccine, vol. 18, 2000, pp. 18-28.
Urasawa et al., "Sequential Passages of Human Rotavirus in MA-104 Cells". Microbiology and Immunology, vol. 25, No. 10, 1981, pp. 1025-1035.
Van Alstine, W.G., "Mystery Swine Disease in the United States". The New Pig Disease: Porcine Respiration and Reproductive Syndrome. A Report on the Seminar/Workshop Held in Brussels by the European Commission (Directorate-General for Agriculture), Apr. 29-30, 1991, pp. 65-70.
Van Alstine, W.G., "Past Diagnostic Approaches and Findings and Potentially Useful Diagnostic Strategies". Proceedings Mystery Swine Disease Committee Meeting, Oct. 6, 1990, pp. 52-58.
Van Berlo et al., "Equine Arteritis Virus-Infected Cells Contain Six Polyadenylated Virus-Specific RNAs". Virology, vol. 118, 1982, pp. 345-352.
Van Der Linden et al., "Virological kinetics and immunological responses to a porcine reproductive and respiratory syndrome virus infection of pigs at different ages". Vaccine, vol. 21, 2003, pp. 1952-1957.
Van Der Meer et al., "ORF1a-Encoded Replicase Subunits Are Involved in the Membrane Association of the Arterivirus Replication Complex". Journal of Virology, vol. 72, No. 8, 1998, pp. 6689-6698.
Van Der Most et al., "A Domain at the 3' End of the Polymerase Gene Is Essential for Encapsidation of Coronavirus Defective Interfering RNAs". Journal of Virology, vol. 65, No. 6, Jun. 1991, pp. 3219-3226.
Van Dinten et al., "Processing of the Equine Arteritis Virus Replicase ORF1b Protein: Identification of Cleavage Products Containing the Putative Viral Polymerase and Helicase Domains". Journal of Virology, vol. 70, No. 10, Oct. 1996, pp. 6625-6633.
Van Dinten et al., "Proteolytic Processing of the Open Reading Frame 1b-Encoded Part of Arterivirus Replicase Is Mediated by nsp4 Serine Protease and Is Essential for Virus Replication". Journal of Virology, vol. 73, No. 3, Mar. 1999, pp. 2027-2037.
Van Marle et al., "Arterivirus discontinuous mRNA transcription is guided by base pairing between sense and antisense transcription-regulating sequences". Proceedings of the National Academy of Sciences, vol. 96, 1999, pp. 12056-12061.

(56) References Cited

OTHER PUBLICATIONS

Van Marle et al., "Characterization of an Equine Arteritis Virus Replicase Mutant Defective in Subgenomic mRNA Synthesis". Journal of Virology, vol. 73, No. 7, Jul. 1999, pp. 5274-5281.
Van Marle et al., "Regulation of Coronavirus mRNA Transcription". Journal of Virology, vol. 69, No. 12, Dec. 1995, pp. 7851-7856.
Van Nieuwstadt et al., "Infection with porcine respiratory coronavirus does not fully protect pigs against intestinal transmissable gastroenteritis virus". The Veterinary Record, vol. 125, No. 3, 1989, pp. 58-60.
Van Nieuwstadt et al., "Proteins Encoded by Open Reading Frames 3 and 4 of the Genome of Lelystad Virus (Arteriviridae) Are Structural Proteins of the Virion". Journal of Virology, vol. 70, No. 7, Jul. 1996, pp. 4767-4772.
Van Nieuwstadt et al., "Use of two enzyme-linked immunosorbent assays to monitor antibody responses in swine with experimentally induced infection with porcine epidemic diarrhea virus". American Journal of Veterinary Research, vol. 42, Jul. 1991, pp. 1044-1050.
Van Zijl et al., "Live Attenuated Pseudorabies Virus Expressing Envelope Glycoprotein E1 of Hog Cholera Virus Protects Swine Against Both Pseudorabies and Hog Cholera". Journal of Virology, vol. 65, No. 5, May 1991, pp. 2761-2765.
Vennema et al., "Nucleocapsid-independent assembly of coronavirus-like particles by co-expression of viral envelope protein genes". The EMBO Journal, vol. 15, No. 8, 1996, pp. 2020-2028.
Verheije et al., "Safety and protective efficacy of porcine reproductive and respiratory syndrome recombinant virus vaccines in young pigs". Vaccine, vol. 21, 2003, pp. 2556-2563.
Veterinary Bulletin, vol. 58, No. 11, 1988, Nos. 6903-6909, p. 932.
Veterinary Bulletin, vol. 60, No. 3, 1990, Nos. 1536-1551, pp. 255-256.
Vieira et al., "New pUC-derived cloning vectors with different selectable markers and DNA replication origins". Gene, vol. 100, 1991, pp. 189-194.
Visser, Nicolaas, "Declaration of Dr. N. Visser". Nov. 14, 1995, pp. 1-11.
Meulenberg et al., "Nucleocapsid Protein N of Lelystad Virus: Expression by Recombinant Baculovirus, Immunological Properties, and Suitability for Detection of Serum Antibodies". Clinical and Diagnostic Laboratory Immunology, vol. 2, No. 6, Nov. 1995, pp. 652-656.
Meulenberg et al., "Posttranslational Processing and Identification of a Neutralization Domain of the GP4 Protein Encoded by ORF4 of Lelystad Virus". Journal of Virology, vol. 71, No. 8, Aug. 1997, pp. 6061-6067.
Meulenberg et al., "Subgenomic RNAs of Lelystad virus contain a conserved leader-body junction sequence". Journal of General Virology, vol. 74, 1993, pp. 1697-1701.
Molenkamp et al., "Isolation and Characterization of an Arterivirus Defective Interfering RNA Genome". Journal of Virology, vol. 74, No. 7, 2000, pp. 3156-3165.
Molenkamp et al., "The arterivirus replicase is the only viral protein required for genome replication and subgenomic mRNA transcription". Journal of General Virology, vol. 81, No. 10, 2000, pp. 2491-2496.
Montagnon, B.J., "Polio and rabies vaccines produced in continuous cell lines: a reality for Vero cell line". Dev Biol Stand., vol. 70, 1989, pp. 27-47.
Moore, C., "Porcine Proliferative and Necrotyzing Pneumonia Clinical Findings". Presented at American Association of Swine Practitioners, 22nd Annual Meeting, Mar. 3-5, 1991, pp. 443-453.
Moormann et al., "Hog cholera virus: identification and characterization of the viral RNA and the virus specific RNA synthesized in infected swine kidney cells". Virus Research, vol. 11, 1988, pp. 281-291.
Moormann et al., "Molecular cloning and nucleotide sequence of hog cholera virus strain brescia and mapping of the genomic region encoding envelope protein E1". Virology, vol. 177, No. 1, Jul. 1990, pp. 184-198.
Morin et al., "Severe proliferative and necrotizing pneumonia in pigs: A newly recognized disease". Canadian Veterinary Journal, vol. 31, Dec. 1990, pp. 837-839.
Morrison et al., "Brief Communications Serologic evidence incriminating a recently isolated virus (ATCC VR-2332) as the cause of swine infertility and respiratory syndrome (SIRS)". Journal of Veterinary Diagnostic Investigation, vol. 4, No. 2, Apr. 1992, pp. 186-188.
Morrison et al., "Sero-epidemiologic Investigation of Swine Infertility and Respiratory Syndrome (SIRS)". 72st Annual Meeting of the Conference of Research Workers in Animal Disease, Chicago, IL, Nov. 11-12, 1991, p. 55, Abstract No. 309.
Mountz et al., "The in vivo generation of murine IgD-secreting cells is accompanied by deletion of the Cμ gene and occasional deletion of the gene for the Cd1 domain". The Journal of Immunology, vol. 145, No. 5, Sep. 1990, pp. 1583-1591.
Mukamoto et al., "Immunogenicity in Aujeszky's disease virus structural glycoprotein gVI (gp50) in swine". Veterinary Microbiology, vol. 29, No. 2, Oct. 1991, pp. 109-121.
Murakami, et al., "Difference in growth behavior of human, swine, equine, and avian influenza viruses at a high temperature". Archives of Virology, vol. 100, Nos. 3-4, 1988, pp. 231-244.
Murphy et al., "Immunization Against Virus" in Virology, 2nd Edition, vol. 1, Fields, et al., eds. Raven Press, NY, 1990, pp. 469-502.
Murphy et al., "Virus Taxonomy". Chapter 2 in Fields Virology, 2nd. Edition, Fields, et al., eds, Raven Press, New York, 1990, pp. 9-35.
Murtaugh et al., "Genetic Variation in the PRRS Virus". Coronaviruses and Arteriviruses, Plenum Press, New York, 1998, pp. 787-794.
Murtaugh et al., "Immunological Responses of Swine to Porcine Reproductive and Respiratory Syndrome Virus Infection". Viral Immunology, vol. 15, No. 4, 2002, pp. 533-547.
Murtaugh et al., "Role of Viral Proteases in PRRS Immunity, Project Period Sep. 1, 1997-Dec. 31, 2002, no cost extension Jan. 1, 2003-Jun. 30, 2003". Final Report: Aug. 30, 2003, Department of Veterinary Pathology, University of Minnesota, St. Paul, MN and Boehringer Ingelheim Vetmedica, Inc., Ames, IA, 2003, pp. 1-38.
Murtaugh, "Allen D Lehman Swine Conference: the Evolution of the Swine veterinary profession: The PRRS Virus". University of Minnesota, Veterinary Continuing Education and Extension, vol. 20, 1993, pp. 43-47.
Myers et al., "Propagation of avian rotavirus in primary chick kidney cell and MA104 cell cultures". Avian Diseases, vol. 33, No. 3, Jul.-Sep. 1989, pp. 578-581.
Nakamura et al., "Studies on Swine Influenza III. Propagation of Swine Influenza Virus in Explants of Respiratory Tract Tissues from Fetal Pigs". The Cornell Veterinarian, vol. LX, No. 1, Jan. 1970, pp. 27-35.
Narayanan et al., "Characterization of the Coronavirus M Protein and Nucleocapsid Interaction in Infected Cells". Journal of Virology, vol. 74, No. 17, Sep. 2000, pp. 8127-8134.
NCBI: Accession No. M96262.2. "Lelystad virus, complete genome." Nov. 8, 2000.
NCBI: Accession No. NC_001639. Lactate dehydrogenase-elevating virus, complete genome. Dec. 8, 2008.
NCBI: Accession No. NC_002533. "Lelystad virus, complete genome." Nov. 11, 2000.
Nelson et al., "Differentiation of U.S. And European Isolates of Porcine Reproductive and Respiratory Syndrome Virus by Monoclonal Antibodies". Journal of Clinical Microbiology, vol. 31, No. 12, Dec. 1993, pp. 3184-3189.
Nelson et al., "High affinity interaction between nucleocapsid protein and leader/intergenic sequence of mouse hepatitis virus RNA". Journal of General Virology, vol. 81, 2000, pp. 181-188.
Nielsen et al., "Generation of an Infectious Clone of VR-2332, a Highly Virulent North American-Type Isolate of Porcine Reproductive and Respiratory Syndrome Virus". Journal of Virology, vol. 77, No. 6, Mar. 2003, pp. 3702-3711.
Nishimura et al., "Replication and Synthesis of Japanese Encephalitis Virus Ribonucleic Acids in Vero Cells". Japanese Journal of Microbiology, vol. 15, No. 4, 1971, pp. 309-316.

(56) References Cited

OTHER PUBLICATIONS

Nodelijk et al., "A quantitative assessment of the effectiveness of PRRSV vaccination in pigs under experimental conditions". Vaccine, vol. 19, 2000, pp. 3636-3644.
Notice of Opposition by Akzo Nobel against European Patent No. 0 587 780, Nov. 28, 1995, EP.
Notice of Opposition by Cyanamid Iberica against European Patent No. 0 587 780, Nov. 28, 1995, EP.
Nuttall, P.A., "Growth Characteristics of Two Strains of Bovine Virus Diarrhoea Virus". Archives of Virology, vol. 66, 1980, pp. 365-369.
Oirschot et al., "Development of an ELISA for detection of antibodies to glycoprotein I of Aujeszky's disease virus: a method for the serological differentiation between infected and vaccinated pigs". Journal of Virological Methods, vol. 22, 1988, pp. 191-206.
Ojeh et al., "Isolation, characterisation and serial propagation of a Nigerian strain of porcine group A rotavirus in a monkey kidney cell line (MA104)". Discovery and Innovation, vol. 8, No. 2, Jun. 1996, pp. 159-164.
Oleksiewicz et al., "Epitope Mapping Porcine Reproductive and Respiratory Syndrome Virus by Phage Display: the nsp2 Fragment of the Replicase Polyprotein Contains a Cluster of B-Cell Epitopes". Journal of Virology, vol. 75, No. 7, Apr. 2001, pp. 3277-3290.
Oleksiewicz et al., "Semen from Boars Infected with Porcine Reproductive and Respiratory Syndrome Virus (PRRSV) Contains Antibodies Against Structural as Well as Nonstructural Viral Proteins". Veterinary Microbiology, vol. 81, 2001, pp. 109-125.
Olsthoorn et al., "A conformational switch at the 3' end of a plant virus RNA regulates viral replication". The EMBO Journal, vol. 18, No. 17, 1999, pp. 4856-4864.
Opriessnig et al., "Comparison of Molecular and Biological Characteristics of a Modified Live Porcine Reproductive and Respiratory Syndrome Virus (PRRSV) Vaccine (Ingelvac PRRS MLV), the Parent Strain of the Vaccine (ATCC VR2332), ATCC VR2385, and Two Recent Field Isolates of PRRSV". Journal of Virology, vol. 76, No. 23, Dec. 2002, pp. 11837-11844.
Opriessnig et al., "Use of an Experimental Model to Test the Efficacy of Planned Exposure to Live Porcine Reproductive and Respiratory Syndrome Virus". Clinical and Vaccine Immunology, vol. 14, No. 12, Dec. 2007, pp. 1572-1577.
Ostrowski et al., "Identification of Neutralizing and Nonneutralizing Epitopes in the Porcine Reproductive and Respiratory Syndrome Virus GP5 Ectodomain". Journal of Virology, vol. 76, No. 9, May 2002, pp. 4241-4250.
Pan et al., "Replication of African swine fever virus in cell cultures". American Journal of Veterinary Research, vol. 41, No. 9, Sep. 1980, pp. 1357-1367.
Parratt et al., "Radioimmunoassay of Antibody and its Clinical Applications". John Wiley & Sons, Chichester, 1982, p. 43.
Parsley et al., "Poly (rC) binding protein 2 forms a ternary complex with the 5'-terminal sequences of poliovirus RNA and the viral 3CD proteinase". RNA, vol. 3, 1997, pp. 1124-1134.
Patriarca, et al., "Lack of Significant Person-to-Person Spread of Swine Influenza-Like Virus Following Fatal Infection in an Immunocomprised Child". American Journal of Epidemiology, vol. 119, No. 2, 1984, pp. 152-158.
Paul et al., "Porcine Reproductive and Respiratory Syndrome: An Overview". Journal of Clinical Veterinary Medicine, vol. 11, No. 12, Nov. 1993, pp. 1-16.
Pearson et al., "Improved tools for biological sequence comparison". Proceedings of the National Academy of Sciences, vol. 85, Apr. 1988, pp. 2444-2448.
Pedersen et al., "Open Reading Frame 1a-Encoded Subunits of the Arterivirus Replicase Induce Endoplasmic Reticulum-Derived Double-Membrane Vesicles Which Carry the Viral Replication Complex". Journal of Virology, vol. 73, No. 3, Mar. 1999, pp. 2016-2026.
Chang et al., "Evolution of Porcine Reproductive and Respiratory Syndrome Virus during Sequential Passages in Pigs". Journal of Virology, vol. 76, No. 10, May 2002, pp. 4750-4763.
Chao et al., "Monoclonal Antibodies to Metacyclic Stage Antigens of Trypanosoma Cruzi" The American Journal of Tropical Medicine and Hygiene, vol. 34, No. 4, Jul. 1985, pp. 694-701.
Charley, B., "Interaction of influenza virus with swine alveolar macrophages: Influence of anti-virus antibodies and cytochalasin B". Annales de l'Instiut Pasteur. Virologie, vol. 134, No. 1, Jan. 1983, pp. 51-59.
Chasey et al., "Replication of Atypical Ovine Rotavirus in Small Intestine and Cell Culture". Journal of General Virology, vol. 67, No. 3, Mar. 1986, pp. 567-576.
Chen et al., "Determination of the 5' end of the lactate dehydrogenase-elevating virus genome by two independent approaches". Journal of General Virology, vol. 75, 1994, pp. 925-930.
Christianson et al., "Experimental Reproduction of a Newly Described Viral Disease, Swine Infertility and Respiratory Syndrome (SIRS), in Pregnant Sows". 72nd Annual Meeting of the Conference of Research Workers in Animal Disease, Chicago, IL, Nov. 11 & 12, 1991, p. 48, Abstract No. 269.
Christianson et al., "Experimental reproduction of swine infertility and respiratory syndrome in pregnant sows". American Journal of Veterinary Research, vol. 53, No. 4, Apr. 1992, pp. 485-488.
Christianson et al., "Porcine reproductive and respiratory syndrome: A review"., Journal of Swine Health and Production, vol. 2, No. 2, Mar. and Apr. 1994, pp. 10-28.
Christianson et al., "Swine Infertility and Respiratory Syndrome". Pig Veterinary Journal, vol. 27, No. 9, Apr. 1991, pp. 9-12.
Chutivongse et al., "One-year study of the 2-1-1 intramuscular postexposure rabies vaccine regimen in 100 severely exposed Thai patients using rabies immune globulin and Vero cell rabies vaccine". Vaccine, vol. 9, No. 8, Aug. 1991, pp. 573-576.
Clark et al., "Trypsin enhancement of rotavirus infectivity: mechanism of enhancement". Journal of Virology, vol. 39, No. 3, Sep. 1981, pp. 816-822.
Collins et al., "Experimental Transmission of Swine Reproductive Failure Syndrome (Mystery Swine Disease) in Gnotobiotic Piglets". 71st Annual Meeting of the Conference of Research Workers in Animal Disease, Chicago, IL, Nov. 5-6, 1990, Abstract No. 2.
Collins et al., "Isolation of swine infertility and respiratory syndrome virus (isolate ATCC VR-2332) in North America and experimental reproduction of the disease in gnotobiotic pigs". Journal of Veterinary Diagnostic Investigation, vol. 4, 1992, pp. 117-126.
Collins et al., "Production of infectious human respiratory syncytial virus from cloned cDNA confirms an essential role for the transcription elongation factor from the 5' proximal open reading frame of the M2 mRNA in gene expression and provides a capability for vaccine development". Proceedings of the National Academy of Sciences, vol. 92, Dec. 1995, pp. 11563-11567.
Collins et al., "Respiratory Disease in a Swine Herd Experiencing a Reproductive Failure Syndrome". Minnesota Swine Conference for Veterinarians, Sep. 16-18, 1990, pp. 206-207.
Collins et al., "Swine Diagnostic Pathology". Allen D. Leman Swine Conference, College of Veterinary Medicine, University of Minnesota, Sep. 18-22, 1998, pp. 1-4.
Collins et al., "Swine Infertility and Respiratory Syndrome (Mystery Swine Disease)". Minnesota Swine Conference for Veterinarians, St. Paul, MN, Sep. 15-17, 1991, pp. 200-205.
Collins, J.E., "Newly Recognized Respiratory Syndromes in North American Swine Herds". American Association of Swine Practitioners Newsletter, vol. 3, No. 7, Sep.-Oct. 1991, pp. 7, 10-11.
Conner et al., "Isolation and characteristics of an equine reovirus type 3 and an antibody prevalence survey to reoviruses in horses located in New York State". Veterinary Microbiology, vol. 9, No. 1, Feb. 1984, pp. 15-25.
Conzelmann et al., "Molecular Characterization of Porcine Reproductive and Respiratory Syndrome Virus, a Member of the Arterivirus Group". Virology, vol. 193, 1993, pp. 329-339.
Cooper et al., "Porcine Reproductive and Respiratory Syndrome: NEB-1 PRRSV Infection did not Potentiate Bacterial Pathogens". Journal of Veterinary Diagnostic Investigation, vol. 7, No. 3, Jul. 1995, pp. 313-320.

(56) References Cited

OTHER PUBLICATIONS

Corn et al., "Isolation of Vesicular Stomatitis Virus New Jersey Serotype from Phlebotomine Sand Files in Georgia". The American Journal of Tropical Medicine and Hygiene, vol. 42, No. 5, May 1990, pp. 476-482.
Dacso, et al., "Sporadic occurrence of zoonotic swine influenza virus infections". Journal of Clinical Microbiology, vol. 20, No. 4, Oct. 1984, pp. 833-835.
Database WPIL Week 8702, Derwent Publications Ltd., London, GB; AN 87-009295 [2] & EP, A,208672 (Regional Wallonne-Chiron Corp, Wallonne Regional) Jan. 14, 1987.
Database WPIL Week 8741, Derwent Publications Ltd., London, GB; AN 87-286929 [41] & EP, A,62, 198626 (ZA Bieseibutsu Kagaku Ken) Sep. 2, 1987.
Database WPIL Week 8821, Derwent Publications Ltd., London, GB; AN 88-147502 [21] & WO,A,8 803 410 (Inst Pasteur) May 19, 1988.
De Mazancourt et al., "Antibody response to the rubella virus structural proteins in infants with the congenital rubella syndrome". Journal of Medical Virology, vol. 19, No. 2, Jun. 1986, pp. 111-122.
De Vries et al., "Genetic Manipulation of Equine Arteritis Virus Using Full-Length cDNA Clones: Separation of Overlapping Genes and Expression of a Foreign Epitope". Virology, vol. 270, No. 1, 2000, pp. 84-97.
De Vries et al., "The Genome Organization of the Nidovirales: Similarities and Differences between Arteri-, Toro-, and Coronaviruses". Seminars in Virology, vol. 8, 1997, pp. 33-47.
Dea et al., "Antigenic variant of swine influenza virus causing proliferative and necrotizing pneumonia in pigs". Journal of Veterinary Diagnostic Investigation, vol. 4, No. 4, 1992, pp. 380-392.
Dea et al., "Caracteristiques d'Isolats des virus influenza et de l'encephalomyocardite associes au Syndrome Reproducteur et Respiratoire Porcine (S.R.R.P.) au Quebec.sup.a," Le Medecin Veterinaire Du Quebec, vol. 21, No. 4, Nov. 1991, pp. 170-175.
Dea et al., "Current knowledge on the structural proteins of porcine reproductive and respiratory syndrome (PRRS) virus: comparison of the North American and European isolate". Archives of Virology, vol. 145, No. 4, Apr. 2000, pp. 659-688.
Dea et al., "Isolation of encephalomyocarditis virus among stillborn and post-weaning pigs in Quebec". Archives of Virology, vol. 117, Nos. 1-2, 1991, pp. 121-128.
Dea et al., "Swine reproductive and respiratory syndrome in Quebec: Isolation of an enveloped virus serologically-related to Lelystad virus". Canadian Veterinary Journal, vol. 33, No. 12, Dec. 1992, pp. 801-808.
Dea et al., "Virus Isolations from Farms in Quebec Experiencing Severe Outbreaks of Respiratory and Reproductive Problems". Proceedings of the Mystery Swine Disease Committee Meeting, Denver, CO, Oct. 6, 1990, pp. 67-72.
Del Val et al., "Glycosylated components of African swine fever virus particles". Virology, vol. 152, No. 1, Jul. 1986, pp. 39-49.
Den Boon et al., "Equine Arteritis Virus Is Not a Togavirus but Belongs to the Coronaviruslike Superfamily". Journal of Virology, vol. 65, No. 6, 1991, pp. 2910-2920.
Den Boon et al., "Processing and Evolution of the N-Terminal Region of the Arterivirus Replicase ORF1a Protein: Identification of Two Papainlike Cysteine Proteases". Journal of Virology, vol. 69, No. 7, Jul. 1995, pp. 4500-4505.
Deng et al., "An improved procedure for utilizing terminal transferase to add homopolymers to the 3' termini of DNA". Nucleic Acids Research, vol. 9, No. 16, 1981, pp. 4173-4188.
Derbyshire, J.B. "Porcine Enterovirus Infections". Diseases of Swine, Fifth Edition, Chapter 20, 1981, pp. 265-270.
Devereux et al., "A Comprehensive Set of Sequence Analysis Programs for VAX". Nucleic Acids Research, vol. 12, No. 1, 1984, pp. 387-395.
Dianzani et al., "Is Human Immunodeficiency Virus RNA Load Composed of Neutralized Immune Complexes". The Journal of Infectious Diseases, vol. 185, 2002, pp. 1051-1054.
Dildrop et al., "Immunoglobulin V region variants in hybridoma cells. II. Recombination between V genes". The EMBO Journal, vol. 1, No. 5, 1982, pp. 635-640.
Dreher, T.W., "Functions of the 3'-Untranslated Regions of Positive Strand RNA Viral Genomes". Annual Review of Phytopathology, vol. 37, 1999, pp. 151-174.
Drew et al., "Production, characterization and reactivity of monoclonal antibodies to porcine reproductive and respiratory syndrome virus". Journal of General Virology, vol. 76, 1995, pp. 1361-1369.
Drew, T., "Porcine Reproductive and Respiratory Syndrome Virus: A Review". Apr. 1996, 3 pages.
Duan et al., "Identification of a putative Receptor for Porcine Reproductive and Respiratory Syndrome Virus on Porcine Alveolar Macrophages". Journal of Virology, vol. 72, No. 5, May 1998, pp. 4520-4523.
Duran et al. "Recombinant Baculovirus Vaccines Against Porcine Reproductive and Respiratory Syndrome (PRRS)". Abstracts PRRS, Aug. 9-10, 1995, Copenhagen, Denmark, 2 pages.
Dykhuizen et al., "Determining the Economic Impact of the 'New' Pig Disease", Porcine Reproductive and Respiratory Syndrome, A Report on the Seminar Held in Brussels on Nov. 4-5, 1991 and Organized by the European Commission, pp. 53-60.
Easterday, B.C., "Swine Influenza". Diseases of Swine, Sixth Edition, Iowa State University Press, 1986, pp. 244-315. (Part One of Two—pp. 244-285). This NPL is too large for EFS submission. Therefore filing in two parts.
Hirsch et al., "Ultrastructure of Human Leukocytes After Simultaneous Fixation with Glutaraldehyde and Osmium Tetroxide and "Postfixation" in Uranyl Acetate". The Journal of Cell Biology, vol. 38, 1968, pp. 615-627.
Hofmann et al., "Propagation of the virus of porcine epidemic diarrhea in cell culture". Journal of Clinical Microbiology, vol. 26, No. 11, Nov. 1988, pp. 2235-2239.
Hofmann et al., "Quantitation, biological and physicochemical properties of cell culture-adapted porcine epidemic diarrhea coronavirus (PEDV)". Veterinary Microbiology, vol. 20, No. 2, Jun. 1989, pp. 131-142.
Honda et al., "A Serological Comparison of 4 Japanese Isolates of Porcine Enteroviruses with the International Reference Strains". The Japanese Journal of Veterinary Science, vol. 52, No. 1, 1990, pp. 49-54.
Horowitz et al., "Anti-schistosome monoclonal antibodies of different isotypes—correlation with cytotoxicity". The EMBO Journal, vol. 2, No. 2, 1983, pp. 193-198.
Horsfall et al., "General Principles of Animal Virus Multiplication". Viral and Rickettsial Infections of Man, Fourth Edition, J.B. Lippincott Company, Philadelphia, 1965, pp. 239-241.
Horzinek et al., "Studies on the Substructure of Togaviruses: II. Analysis of Equine Arteritis Rubella, Bovine Viral Diarrhea, and Hog Cholera Viruses". Archiv Für die gesamte Virusforschung, vol. 33, 1971, pp. 306-318.
Hoshino et al., "Isolation and characterization of an equine rotavirus". Journal of Clinical Microbiology, vol. 18, No. 3, Sep. 1983, pp. 585-591.
Hoshino et al., "Serotypic Similarity and Diversity of Rotaviruses of Mammalian and Avian Origin as Studied by Plaque-Reduction Neutralization". The Journal of Infectious Diseases, vol. 149, No. 5, May 1984, pp. 694-702.
Hsue et al., "Characterization of an Essential RNA Secondary Structure in the 3' Untranslated Region of the Murine Coronavirus Genome". Journal of Virology, vol. 74, No. 15, Aug. 2000, pp. 6911-6921.
Huang et al., "Polypyrimidine Tract-Binding Protein Binds to the Complementary Strand of the Mouse Hepatitis Virus 39 Untranslated Region, Thereby Altering RNA Conformation". Journal of Virology, vol. 73, No. 11, Nov. 1999, pp. 9110-9116.
Hurrelbrink et al., "Attenuation of Murray Valley Encephalitis Virus by Site-Directed Mutagenesis of the Hinge and Putative Receptor-Binding Regions of the Envelope Protein". Journal of Virology, vol. 75, No. 16, Aug. 2001, pp. 7692-7702.

(56) References Cited

OTHER PUBLICATIONS

Hwang et al., "A 68-Nucleotide Sequence within the 39 Noncoding Region of Simian Hemorrhagic Fever Virus Negative-Strand RNA Binds to Four MA104 Cell Proteins". Journal of Virology, vol. 72, No. 5, May 1998, pp. 4341-4351.
Hyllseth, B., "Structural Proteins of Equine Arteritis Virus". Archiv Für die gesamte Virusforschung, vol. 30, 1973, pp. 177-188.
Iltis et al., "Persistent Varicella-Zoster virus infection in a human rhabdomyosarcoma cell line and recovery of a plaque variant". Infection and Immunity, vol. 37, No. 1, Jul. 1982, pp. 350-358.
Imagawa et al., "Isolation of Foal Rotavirus in MA-104 Cells". Bulleting of Equine Research Institute, vol. 18, 1981, pp. 119-128.
International Search Report for PCT/NL2000/00152 mailed on Jul. 6, 2000.
Izeta et al., "Replication and Packaging of Transmissible Gastroenteritis Coronavirus-Derived Synthetic Minigenomes". Journal of Virology, vol. 73, No. 2, Feb. 1999, pp. 1535-1545.
Jackwood et al., "Replication of Infectious Bursal Disease Virus in Continuous Cell Lines". Avian Diseases, vol. 31, No. 2, Apr.-Jun. 1987, pp. 370-375.
Johnson et al., "Feline panleucopaenia virus. IV. Methods for obtaining reproducible in vitro results". Research in Veterinary Science, vol. 8, No. 2, Apr. 1967, pp. 256-264.
Johnson et al., "Pathogenic and humoral immune responses to porcine reproductive and respiratory syndrome virus (PRRSV) are related to viral load in acute infection". Veterinary Immunology and Immunopathology, vol. 102, No. 3, PRRS Immunology and Immunopathology Special Issue, Dec. 2004, pp. 233-247.
Johnston et al., "Genetic to genomic vaccination". Vaccine, vol. 15, No. 8, 1997, pp. 808-809.
Joo et al., "Encephalomyocarditis Virus as a Potential Cause for Mystery Swine Disease", Livestock Conservation Institute, Proceedings of the Mystery Swine Disease Committee Meeting, Denver, CO, Oct. 6, 1990, pp. 62-66.
Jun et al., "Comparison of Dynamics in Viremia Levels in Chickens Inoculated with Marek's Disease Virus Strains of Different Pathotypes". Virologica Sinica, vol. 16, No. 1, Mar. 2001, pp. 59-63.
Jusa et al., "Effect of heparin on infection of cells by porcine reproductive and respiratory syndrome virus". American Journal of Veterinary Research, vol. 58, No. 5, May 1997, pp. 488-491.
Just et al., "A/New Jersey/76 influenza vaccine trial in seronegative schoolchildren: Comparison of a subunit vaccine with a whole-virus vaccine". Medical Microbiology and Immunology, vol. 164, No. 4, 1978, pp. 277-284.
Kang et al., "Primary Isolation and Identification of Avian Rotaviruses from Turkeys Exhibiting Signs of Clinical Enteritis in a Continuous MA-104 Cell Line". Avian Diseases, vol. 30, 1986, pp. 494-499.
Kasza et al., "Establishment, viral susceptibility and biological characteristics of a swine kidney cell line SK-6". Research in Veterinary Science, vol. 13, No. 1, Jan. 1972, pp. 46-51.
Kasza et al., "Isolation and Characterization of a Rotavirus from Pits". Veterinary Record, vol. 87, 1970, pp. 681-686.
Katz et al., "Antigenic differences between European and American isolates of porcine reproductive and respiratory syndrome virus (PRRSV) are encoded by the carboxyterminal portion of viral open reading frame 3". Veterinary Microbiology, vol. 44, No. 1, Apr. 1995, pp. 65-76.
Keffaber, K, "Reproductive Failure of Unknown Etiology"., AASP Newsletter, vol. 1, No. 2, Sep.-Oct. 1989, pp. 1, 4-5, 8-10.
Keffaber, K.K., "Swine Reproductive Failure of Unknown Etiology". The George A. Young Swine Conference & Annual Nebraska SPF Swine Conference, Aug. 13-14, 1990, pp. 55-67.
Key et al., "Genetic variation and phylogenetic analyses of the ORF5 gene of acute porcine reproductive and respiratory syndrome virus isolates". Veterinary Microbiology, vol. 83, 2001, pp. 249-263.
Kim et al., "Analysis of cis-Acting Sequences Essential for Coronavirus Defective Interfering RNA Replication". Virology, vol. 197, No. 1, Nov. 1993, pp. 53-63.
Kim et al., "Different Biological Characteristics of Wild-Type Porcine Reproductive and Respiratory Syndrome Viruses and Vaccine Viruses and Identification of the Corresponding Genetic Determinants". Journal of Clinical Microbiology, vol. 46, No. 5, May 2008, pp. 1758-1768.
Klein et al., "Deletion of the IgH enhancer does not reduce immunoglobulin heavy chain production of a hybridoma IgD class switch variant". The EMBO Journal, vol. 3, No. 11, Nov. 1984, pp. 2473-2476.
Klinge et al, "Age-dependent resistance to Porcine reproductive and respiratory syndrome virus replication in swine". Virology Journal, vol. 6, No. 177, Oct. 2009.
Klinge et al., "PRRSV replication and subsequent immune responses in swine of various ages". Abstract of Poster No. 56, International Porcine Reproductive and Respiratory Syndrome (PRRS) Symposium, PRRS and PRRSV-Related Diseases: Prevention and Control Strategies, Chicago, IL, Nov. 30-Dec. 1, 2007.
Klovins et al., "A Long-range Pseudoknot in Qb RNA is Essential for Replication". Journal of Molecular Biology, vol. 294, 1999, pp. 875-884.
Klump et al., "Complete Nucleotide Sequence of Infectious Coxsackievirus B3 cDNA: Two Initial 5' Uridine Residues Are Regained during Plus-Strand RNA Synthesis". Journal of Virology, vol. 64, No. 4, Apr. 1990, pp. 1573-1583.
Klupp et al., "Sequence and expression of the glycoprotein gH gene of pseudorabies virus". Virology, vol. 182, No. 2, Jun. 1991, pp. 732-741.
Knowles et al., "Classification of porcine enteroviruses by antigenic analysis and cytopathic effects in tissue culture: Description of 3 new serotypes". Archives of Virology, vol. 62, No. 3, 1979, pp. 201-208.
Kolodziej et al., "Epitope tagging and protein surveillance". Methods in Enzymology, vol. 194, 1991, pp. 508-519.
Kouvelos et al., "Comparison of Bovine, Simian and Human Rotavirus Structural Glycoproteins". Journal of General Virology, vol. 65, Jul. 1984, pp. 1211-1214.
Kundin, W.D., "Hong Kong A-2 Influenza Virus Infection among Swine during a Human Epidemic in Taiwan". Nature, vol. 228, Nov. 1970, p. 857.
Kuo et al., "A Nested Set of Eight RNAs Is Formed in Macrophages Infected with Lactate Dehydrogenase-Elevating Virus", Journal of Virology, vol. 65, No. 9, Sep. 1991, pp. 5118-5123.
Kusanagi et al., "Isolation and Serial Propagation of Porcine Epidemic Diarrhea Virus in Cell Cultures and Partial Characterization of the Isolate". Journal of Veterinary Medical Science, vol. 54, No. 2, 1992, pp. 313-318.
Kutsuzawa et al., "Isolation of Human Rotavirus Subgroups 1 and 2 in Cell Culture". Journal of Clinical Microbiology, vol. 16, No. 4, Oct 1982, pp. 727-730.
Labarque et al., "Effect of cellular changes and onset of humoral immunity on the replication of porcine reproductive and respiratory syndrome virus in the lungs of pigs". Journal of General Virology, vol. 81, 2000, pp. 1327-1334.
Labarque et al., "Respiratory tract protection upon challenge of pigs vaccinated with attenuated porcine reproductive and respiratory syndrome virus vaccines". Veterinary Microbiology, vol. 95, 2003, pp. 187-197.
Darwich et al., "Genetic and immunobiological diversities of porcine reproductive and respiratory syndrome genotype I strains". Veterinary Microbiology, vol. 150, 2011, pp. 49-62.
Matanin et al., "Purification of the major envelop protein GP5 of porcine reproductive and respiratory syndrome virus (PRRSV) from native virions". Journal of Virological Methods, vol. 147, 2008, pp. 127-135.
Pesch et al., "New insights into the genetic diversity of European porcine reproductive and respiratory syndrome virus (PRRSV)". Veterinary Microbiology, vol. 107, 2005, pp. 31-48.
Gao et al., "Genomic characterization of two Chinese isolates of Porcine respiratory and reproductive syndrome virus*". Archives of Virology, vol. 149, 2004, pp. 1341-1351.
UniProt: Accession No. C9E449. "SubName: Full=M protein; SubName: Full= Membrane protein". Nov. 3, 2009.
UniProt: Accession No. D0VEE4. "SubName: Full=Unglycosylated membrane protein". Dec. 15, 2009.

(56) References Cited

OTHER PUBLICATIONS

UniProt: Accession No. Q6TLB4. "SubName: Full= Membrane protein M". Jul. 5, 2004.
Cano et al., "Impact of a modfied-live porcine reproductive and respiratory syndrome virus vaccine intervention on a population of pigs infected with a heterologous isolate". Vaccine, vol. 25, 2007, pp. 4382-4391.
Lai et al., "Coronavirus: how a large RNA viral genome is replicated and transcribed". Infectious Agents and Disease, vol. 3, Nos. 2-3, 1994, pp. 98-105.
Lai et al., "Coronavirus: organization, replication and expression of genome". Annual Review of Microbiology, vol. 33, 1990, pp. 303-333.
Lai et al., "Infectious RNA transcribed from stably cloned full-length cDNA of dengue type 4 virus". Proceedings of the National Academy of Sciences, vol. 88, Jun. 1991, pp. 5139-5143.
Lazar et al., "Transforming Growth Factor a: Mutation of Aspartic Acid 47 and Leucine 48 Results in Different Biological Activities". Molecular and Cellular Biology, vol. 8, No. 3, Mar. 1988, pp. 1247-1252.
Leitner et al., "DNA and RNA-based vaccines: principles, progress and prospects". Vaccine, vol. 18, 2000, pp. 765-777.
Levy et al., "Freeze-drying is an effective method for preserving infectious type C retroviruses". Journal of Virological Methods, vol. 5, Nos. 3-4, Nov. 1982, pp. 165-171.
Liljestrom et al., "A New Generation of Animal Cell Expression Vectors Based on the Semliki Forest Virus Replicon". Nature Biotechnology, vol. 9, 1991, pp. 1356-1361.
Lin et al., "Deletion Mapping of a Mouse Hepatitis Virus Defective Interfering RNA Reveals the Requirement of an Internal and Discontiguous Sequence fro Replication". Journal of Virology, vol. 67, No. 10, Oct. 1993, pp. 6110-6118.
Lin et al., "Identification of the cis-Acting Signal for Minus-Strand RNA Synthesis of a Murine Coronavirus: Implications for the Role of Minus-Strand RNA in RNA Replication and Transcription". Journal of Virology, vol. 68, No. 12, Dec. 1994, pp. 8131-8140.
Lin et al., "The 3' Untranslated Region of Coronavirus RNA Is Required for Subgenomic mRNA Transcription from a Defective Interfering RNA". Journal ofVirology, vol. 70, No. 10, Oct. 1995, pp. 7236-7240.
Liu et al., "A Specific Host Cellular Protein Binding Element Near the 3? End of Mouse Hepatitis Virus Genomic RNA". Virology, vol. 232, No. 1, May 1997, pp. 74-85.
Loula, T., "Clinical Presentation of Mystery Pig Disease in the Breeding Herd and Suckling Piglets". Proceedings of the Mystery Swine Disease Committee Meeting, Denver, CO, Oct. 6, 1990, pp. 37-40.
Loula, T., "Mystery Pig Disease", Agri-Practice, vol. 12, No. 1, Jan.-Feb. 1991, pp. 29-34.
Luytjes et al., "Replication of Synthetic Defective Interfering RNAs Derived from Coronavirus Mouse Hepatitis Virus-A59". Virology, vol. 216, No. 1, Feb. 1996, pp. 174-183.
Lv et al., "An infectious cDNA clone of a highly pathogenic porcine reproductive and respiratory syndrome virus variant associated with porcine high fever syndrome". Journal of General Virology, vol. 89, 2008, pp. 2075-2079.
Madec et al., "Consequences pathologiques d'un episode grippal severe (virus swine A/H1N1 dans les conditions naturelles chez la truie non immune en debut de gestation". Comparative Immunology, Microbiology and Infectious Diseases, vol. 12, Nos. 1-2, 1989, pp. 17-27.
Madin, S.H. "Vesicular Exanthema Virus". Virus Infections of Porcines, Elsevier Science Publishers B.V., 1989, pp. 267-271.
Makabe et al., "Hemagglutination with Ovine Rotavirus". Archives of Virology, vol. 90, 1986, pp. 153-158.
Makino et al., "Leader sequences of murine coronavirus mRNAs can be freely reassorted: Evidence for the role of free leader RNA in transcription". Proceedings of the National Academy of Sciences, vol. 83, Jun. 1986, pp. 4204-4208.
Makino et al., "Primary Structure and Translation of a Defective Interfering RNA of Murine Coronavirus". Virology, vol. 166, 1988, pp. 550-560.
Mardassi et al., "Identification of major differences in the nucleocapsid protein genes of a Québec strain and European strains of porcine reproductive and respiratory syndrome virus". vol. 75, No. 3, Mar. 1994, pp. 681-685.
Mason, P.W., "Maturation of Japanese encephalitis virus glycoproteins produced by infected mammalian and mosquito cells". Virology, vol. 169, No. 2, Apr. 1989, pp. 354-364.
Masters et al., "Functions of the coronavirus nucleocapsid protein". Coronaviruses and Their Diseases, Plenum Press, New York, pp. 235-238.
Masurel, N., "Swine Influenza Virus and the Recycling of Influenza-A Viruses in Man". The Lancet, Jul. 31, 1976, pp. 244-247.
McAuliffe et al., "Codon Substitution Mutations at Two Positions in the L Polymerase Protein of Human Parainfluenza Virus Type 1 Yield Viruses with a Spectrum of Attenuation In Vivo and Increased Phenotypic Stability In Vitro". Journal of Virology, vol. 78, No. 4, Feb. 2004, pp. 2029-2036.
McCullough et al., "9. Experimental Transmission of Mystery Swine Disease", The New Pig Disease Porcine Respiration and Reproductive Syndrome, A report on the seminar/workshop held in Brussels on Apr. 29-30, 1991, pp. 46-52.
McDaniel, H.A., "African Swine Fever". Diseases of Swine, 5th Edition, Chapter 18, The Iowa State University Press, Ames, Iowa, 1981, pp. 237-245.
McFerran, J.B., "Reovirus Infection". Diseases of Swine, Fifth Edition, Chapter 28, The Iowa State University Press, Ames, Iowa, 1981, pp. 330-334.
McIntosh, "Diagnostic Virology". Fields Virology, Ch. 17, Second Edition, vol. 1, 1990, pp. 411-437.
McKinney, W.P., "Fatal Swine Influenza Pneumonia During Late Pregnancy". Archives of Internal Medicine, vol. 150, No. 1, Jan. 1990, pp. 213-215.
McQueen et al., "Influenza in animals". Advances in Veterinary Science, vol. 12, 1968, pp. 285-336.
Meikeljohn et al., "Respiratory Virus Vaccine Evaluation and Surveillance". Semi-Annual Contract Progress Report to the National Institute of Allergy and Infectious Diseases, Sep. 15, 1965 to Mar. 15, 1966, 21 pgs.
Melchers et al., "Cross-talk between orientation-dependent recognition determinants of a complex control RNA element, the enterovirus oriR". RNA, vol. 6, 2000, pp. 976-987.
Mendez et al., "Molecular Characterization of Transmissible Gastroenteritis Coronavirus Defective Interfering Genomes: Packaging and Heterogeneity". Virology, vol. 217, 1996, pp. 495-507.
Meng et al., "Characterization of a High-Virulence US Isolate of Porcine Reproductive and Respiratory Syndrome Virus in a Continuous Cell Line, ATCC CRL11171". Journal of Veterinary Diagnostic Investigation, vol. 8, No. 3, Jul. 1996, pp. 374-381.
Meng, X.J., "Heterogeneity of porcine reproductive and respiratory syndrome virus: implications for current vaccine efficacy and future vaccine development". Veterinary Microbiology, vol. 74, 2000, pp. 309-329.
Mengeling et al., "An update of research at the National Animal Disease Center on current field strains of Porcine Reproductive and Respiratory Syndrome (PRRS) virus". Allen D. Leman Swine Conference, 1997, pp. 138-145.
Mengeling et al., "Clinical consequences of exposing pregnant gilts to strains of porcine reproductive and respiratory syndrome (PRRS) virus isolated from field cases of "atypical" PRRS". American Journal of Veterinary Research, vol. 59, No. 12, Dec. 1998, pp. 1540-1544.
Mengeling et al., "Clinical Effects of porcine reproductive and respiratory syndrome virus on pigs during the early postnatal interval". American Journal of Veterinary Research, vol. 59, No. 1, Jan. 1998, pp. 52-55.
Mengeling et al., "Comparative safety and efficacy of attenuated single-strain and multi-strain vaccines for porcine reproductive and respiratory syndrome". Veterinary Microbiology, vol. 93, 2003, pp. 25-38.

(56) References Cited

OTHER PUBLICATIONS

Mengeling et al., "Comparison among strains of porcine reproductive and respiratory syndrome virus for their ability to cause reproductive failure". American Journal of Veterinary Research, vol. 57, No. 6, Jun. 1996, pp. 834-839.
Mengeling et al., "Strain specificity of the immune response of pigs following vaccination with various strains of porcine reproductive and respiratory syndrome virus". Veterinary Microbiology, vol. 93, 2003, pp. 13-24.
Meredith, MJ, "Porcine Reproductive and Respiratory Syndrome (PRRS)", Pig Disease Information Center, 1st North American Edition, University of Cambridge, Aug. 1994, pp. 1-57.
Mettenleiter et al., "Isolation of a viable herpesvirus (pseudorabies virus) mutant specifically lacking all four known nonessential glycoproteins". Virology, vol. 179, No. 1, Nov. 1990, pp. 498-503.
Meulenberg et al., "Characterization of Proteins Encoded by ORFs 2 to 7 of Lelystad Virus". Virology, vol. 206, No. 1, Jan. 1995, pp. 155-163.
Meulenberg et al., "Identification and Characterization of a Sixth Structural Protein of Lelystad Virus: The Glycoprotein GP2Encoded by ORF2 Is Incorporated in Virus Particles". Virology, vol. 225, No. 1, Nov. 1996, pp. 44-51.
Meulenberg et al., "Infectious Transcripts from Cloned Genome-Length cDNA of Porcine Reproductive and Respiratory Syndrome Virus". Journal of Virology, vol. 72, No. 1, Jan. 1998, pp. 380-387.
Meulenberg et al., "Lelystad Virus, the Causative Agent of Porcine Epidemic Abortion and Respiratory Syndrome (PEARS), is Related to LDV and EAV". Virology, vol. 192, 1993, pp. 62-72.
Meulenberg et al., "Localization and Fine Mapping of Antigenic Sites on the Nucleocapsid Protein N of Porcine Reproductive and Respiratory Syndrome Virus with Monoclonal Antibodies". Virology, vol. 252, 1998, pp. 106-114.
Meulenberg et al., "Molecular characterization of Lelystad virus". Veterinary Microbiology, vol. 55, 1997, pp. 197-202.
Edwards et al., "Oligodeoxyribonucleotide ligation to single-stranded cDNAs: a new tool for cloning 5' ends of mRNAs and for constructing cDNA libraries by in vitro amplification". Nucleic Acids Research, vol. 19, No. 19, 1991, pp. 5227-5232.
Greiner et al., "Quantitative Effect of Porcine Reproductive Respiratory Syndrome Virus on Pig Growth and Immune Response".,1999, Swine Research Report, Paper 5, 1998, 4 pages.
Hao et al., "Polymorphic genetic characterization of the ORF7 gene of porcine reproductive and respiratory syndrome virus (PRRSV) in China". Virology Journal, vol. 8, No. 73, 2011, pp. 1-9.
Mardassi et al., "Structural Gene Analysis of a Quebec Reference Strain of Porcine Reproductive and Respiratory Syndrome Virus (PRRSV)". Corona- and Related Viruses, Edited by P.J. Talbot and G.A. Levy, Plenum Press, New York, 1995, pp. 277-281.
Masters et al., "Functions of the coronavirus nucleocapsid protein". Coronaviruses and Their Diseases, Plenum Press, New York, 1990, pp. 235-238.
Wootton et al., "Structure-function of the ORF7 protein of porcine reproductive and respiratory syndrome virus in the viral capsid assembly". Proceedings of the International Symposium on PRRS and Aujeszky's Disease, Ploufragan, France, Jun. 21-24, 1999, pp. 37-38.

* cited by examiner

| Mutation | Description | Construct (pABV) | RNA-replication | N-protein expression | virus production |
|---|---|---|---|---|---|
| | wild type | 437 | + | + | + |
| | Gln-5→stop | 522 | + | +* | − |
| | Δ ORF7 | 521 | − | − | − |
| | Δ 348 nt. 5' ORF7 | 605 | − | − | − |
| | Δ 297 nt. 5' ORF7 | 604 | − | − | − |
| | Δ 198 nt. 5' ORF7 | 603 | − | − | − |
| | Δ 99 nt. 5' ORF7 | 602 | − | − | − |
| | Δ 55 nt. 5' ORF7 | 624 | + | +* | − |
| | Δ 45 nt. 5' ORF7 | 625 | + | +* | − |
| | Δ 10 nt. 3' ORF6 | 626 | + | + | − |
| | Δ 54 nt. 3' ORF6 | 627 | + | + | − |
| | Δ ORF2-5'ORF6 | 594 | + | + | − |

*: results in the expression of a truncated N protein

SEQUENCE LISTING

```
<160> NUMBER OF SEQ ID NOS: 29

<210> SEQ ID NO 1
<211> LENGTH: 6
<212> TYPE: PRT
<213> ORGANISM: Porcine reproductive and respiratory syndrome virus

<400> SEQUENCE: 1

Gln Leu Cys Gln Leu Leu
1               5


<210> SEQ ID NO 2
<211> LENGTH: 17
<212> TYPE: PRT
<213> ORGANISM: Porcine reproductive and respiratory virus

<400> SEQUENCE: 2

Pro Glu Lys Pro His Phe Pro Leu Ala Ala Glu Asp Asp Ile Arg His
1               5                   10                  15

His
```

-continued

<210> SEQ ID NO 3
<211> LENGTH: 11
<212> TYPE: PRT
<213> ORGANISM: Porcine reproductive and respiratory virus

<400> SEQUENCE: 3

Ile Ser Thr Ala Phe Asn Gln Gly Ala Gly Thr
1 5 10

<210> SEQ ID NO 4
<211> LENGTH: 26
<212> TYPE: DNA
<213> ORGANISM: Artificial Sequence
<220> FEATURE:
<223> OTHER INFORMATION: PCR Primer

<400> SEQUENCE: 4
cattgcaccc agaactggtt cagttg 26

<210> SEQ ID NO 5
<211> LENGTH: 27
<212> TYPE: DNA
<213> ORGANISM: Artificial Sequence
<220> FEATURE:
<223> OTHER INFORMATION: PCR Primer

<400> SEQUENCE: 5
cgtctggatc gattgcaaga ggaggga 27

<210> SEQ ID NO 6
<211> LENGTH: 69
<212> TYPE: DNA
<213> ORGANISM: Artificial Sequence
<220> FEATURE:
<223> OTHER INFORMATION: PCR Primer

<400> SEQUENCE: 6
tctggatcga ttgcaagcag agggagcgtt cagtctgggt gaggtggtgc cggatgtcat 60
attcagcag 69

<210> SEQ ID NO 7
<211> LENGTH: 28
<212> TYPE: DNA
<213> ORGANISM: Artificial Sequence
<220> FEATURE:
<223> OTHER INFORMATION: PCR Primer

<400> SEQUENCE: 7
gattggatcc aacacatcat tcgagctg 28

<210> SEQ ID NO 8
<211> LENGTH: 28
<212> TYPE: DNA
<213> ORGANISM: Artificial Sequence
<220> FEATURE:
<223> OTHER INFORMATION: PCR Primer

<400> SEQUENCE: 8
ggattgaaaa tgcaattaat tcatgtat 28

<210> SEQ ID NO 9
<211> LENGTH: 20
<212> TYPE: DNA
<213> ORGANISM: Artificial Sequence
<220> FEATURE:

<223> OTHER INFORMATION: PCR Primer

<400> SEQUENCE: 9
cagccagggg aaaatgtggc 20

<210> SEQ ID NO 10
<211> LENGTH: 37
<212> TYPE: DNA
<213> ORGANISM: Artificial Sequence
<220> FEATURE:
<223> OTHER INFORMATION: PCR Primer

<400> SEQUENCE: 10
gattggatcc accatggagt catggaagtt tatcact 37

<210> SEQ ID NO 11
<211> LENGTH: 21
<212> TYPE: DNA
<213> ORGANISM: Artificial Sequence
<220> FEATURE:
<223> OTHER INFORMATION: PCR Primer

<400> SEQUENCE: 11
tctaggaatt ctagacgatc g 21

<210> SEQ ID NO 12
<211> LENGTH: 22
<212> TYPE: DNA
<213> ORGANISM: Artificial Sequence
<220> FEATURE:
<223> OTHER INFORMATION: PCR Primer

<400> SEQUENCE: 12
tctaggaatt ctagacgatc gt 22

<210> SEQ ID NO 13
<211> LENGTH: 20
<212> TYPE: DNA
<213> ORGANISM: Artificial Sequence
<220> FEATURE:
<223> OTHER INFORMATION: PCR Primer

<400> SEQUENCE: 13
agcaacctag gggaggacag 20

<210> SEQ ID NO 14
<211> LENGTH: 44
<212> TYPE: DNA
<213> ORGANISM: Artificial Sequence
<220> FEATURE:
<223> OTHER INFORMATION: PCR Primer

<400> SEQUENCE: 14
ggagtggtta acctcgtcaa gtatggccgg taaaaaccag agcc 44

<210> SEQ ID NO 15
<211> LENGTH: 36
<212> TYPE: DNA
<213> ORGANISM: Artificial Sequence
<220> FEATURE:
<223> OTHER INFORMATION: PCR Primer

<400> SEQUENCE: 15
ccattcacct gactgtttaa ttaacttgca ccctga 36

-continued

<210> SEQ ID NO 16
<211> LENGTH: 72
<212> TYPE: DNA
<213> ORGANISM: Artificial Sequence
<220> FEATURE:
<223> OTHER INFORMATION: PCR Primer

<400> SEQUENCE: 16
aactttgacc ttctcaagtt ggccggcgac gtcgagtcca acccagggcc cggtaaaaac 60
cagagccaga ag 72

<210> SEQ ID NO 17
<211> LENGTH: 75
<212> TYPE: DNA
<213> ORGANISM: Artificial Sequence
<220> FEATURE:
<223> OTHER INFORMATION: PCR Primer

<400> SEQUENCE: 17
gagtggttaa cctcgtcaag tatggccggt aaatacccat acgatgttcc agattacgct 60
aactttgacc ttctc 75

<210> SEQ ID NO 18
<211> LENGTH: 35
<212> TYPE: DNA
<213> ORGANISM: Artificial Sequence
<220> FEATURE:
<223> OTHER INFORMATION: PCR Primer

<400> SEQUENCE: 18
acgtgcgtta actaaggtgc aatgataaag tccca 35

<210> SEQ ID NO 19
<211> LENGTH: 35
<212> TYPE: DNA
<213> ORGANISM: Artificial Sequence
<220> FEATURE:
<223> OTHER INFORMATION: PCR Primer

<400> SEQUENCE: 19
acgtgcgtta actaaatccg gcaccacctc accca 35

<210> SEQ ID NO 20
<211> LENGTH: 35
<212> TYPE: DNA
<213> ORGANISM: Artificial Sequence
<220> FEATURE:
<223> OTHER INFORMATION: PCR Primer

<400> SEQUENCE: 20
acgtgcgtta actaagggaa ggtcagtttt caggt 35

<210> SEQ ID NO 21
<211> LENGTH: 35
<212> TYPE: DNA
<213> ORGANISM: Artificial Sequence
<220> FEATURE:
<223> OTHER INFORMATION: PCR Primer

<400> SEQUENCE: 21
acgtgcgtta actaacgcct gattcgcgtg acttc 35

<210> SEQ ID NO 22
<211> LENGTH: 41
<212> TYPE: DNA

<213> ORGANISM: Artificial Sequence
<220> FEATURE:
<223> OTHER INFORMATION: PCR Primer

<400> SEQUENCE: 22
aaatacccat acgatgttcc agattacgct aaccagagcc a 41

<210> SEQ ID NO 23
<211> LENGTH: 42
<212> TYPE: DNA
<213> ORGANISM: Artificial Sequence
<220> FEATURE:
<223> OTHER INFORMATION: PCR Primer

<400> SEQUENCE: 23
agtggttaac ctcgtcaagt atggccggta aatacccata cg 42

<210> SEQ ID NO 24
<211> LENGTH: 51
<212> TYPE: DNA
<213> ORGANISM: Artificial Sequence
<220> FEATURE:
<223> OTHER INFORMATION: PCR Primer

<400> SEQUENCE: 24
actgtttaat taagcgtaat ctggaacatc gtatgggtaa cttgcaccct g 51

<210> SEQ ID NO 25
<211> LENGTH: 33
<212> TYPE: DNA
<213> ORGANISM: Artificial Sequence
<220> FEATURE:
<223> OTHER INFORMATION: PCR Primer

<400> SEQUENCE: 25
acgtgcgtta actaaccgat ggggaatggc cag 33

<210> SEQ ID NO 26
<211> LENGTH: 42
<212> TYPE: DNA
<213> ORGANISM: Artificial Sequence
<220> FEATURE:
<223> OTHER INFORMATION: PCR Primer

<400> SEQUENCE: 26
ggagtggtta acctcgtcaa gtaaccgatg gggaatggcc ag 42

<210> SEQ ID NO 27
<211> LENGTH: 31
<212> TYPE: DNA
<213> ORGANISM: Artificial Sequence
<220> FEATURE:
<223> OTHER INFORMATION: PCR Primer

<400> SEQUENCE: 27
acgtgcgtta acggccggta aaaaccagag c 31

<210> SEQ ID NO 28
<211> LENGTH: 30
<212> TYPE: DNA
<213> ORGANISM: Artificial Sequence
<220> FEATURE:
<223> OTHER INFORMATION: PCR Primer

<400> SEQUENCE: 28
gctcgtgcta gcctttagca tcacatacac 30

-continued

```
<210> SEQ ID NO 29
<211> LENGTH: 30
<212> TYPE: DNA
<213> ORGANISM: Artificial Sequence
<220> FEATURE:
<223> OTHER INFORMATION: PCR Primer

<400> SEQUENCE: 29

cttgacgagg ttaactggta ctagagtgcc                                30
```

PRRSV VACCINES

This application is a continuation of U.S. application Ser. No. 09/948,747 filed Sep. 7, 2001, now abandoned, which is a continuation-in-part of U.S. patent application Ser. No. 09/874,626 filed Jun. 5, 2001, now abandoned, which is a continuation of International Application No. PCT/NL97/00593 filed Oct. 29, 1997, now abandoned. Said U.S. patent application Ser. No. 09/874,626 is also a continuation of U.S. application Ser. No. 09/297,535 filed Oct. 12, 1999, now U.S. Pat. No. 6,268,199, which is the National Stage of International Application No. PCT/NL97/00593 filed Oct. 29, 1997, now abandoned.

The invention relates to the field of PRRS viruses and infectious clones obtained from PRRS viruses. Furthermore, the invention relates to vaccines and diagnostic assays obtainable by using and modifying such infectious clones of PRRS viruses.

Porcine reproductive and respiratory syndrome virus (PRRSV) is a positive-strand RNA virus that belongs to the family of arteriviruses together with equine arteritis virus (EAV), lactate dehydrogenase-elevating virus (LDV) and simian hemorrhagic fever virus (Meulenberg et al., 1993). Recently, the International Committee on the Taxonomy of Viruses has decided to incorporate this family in a new order of viruses, the Nidovirales, together with the Coronaviridae (genomic length 28 to 30 kb), and Toroviridae (genomic length 26 to 28 kb). The order Nidovirales represents enveloped RNA viruses that contain a positive-stranded RNA genome and synthesize a 3' nested set of subgenomic RNAs during replication. The subgenomic RNAs of coronaviruses and arteriviruses contain a leader sequence which is derived from the 5' end of the viral genome. The subgenomic RNAs of toroviruses lack a leader sequence. Whereas the ORFs 1a and 1b, encoding the RNA dependent RNA polymerase, are expressed from the genomic RNA, the smaller ORFs at the 3' end of the genomes of Nidovirales, encoding structural proteins, are expressed from the subgenomic mRNAs.

A replicon herein is defined as derived from a recombinant nucleic acid. Although genomic information regarding PRRSV is now emerging, it is for example not known where deletions or modifications in the PRRSV genome can be located so that the resulting recombinant nucleic acid can be used as a functional replicon allowing in vivo RNA replication, be it in (complementary) cells expressing essential (PRRS) viral proteins (such as polymerase or structural (envelope) proteins or not, or allowing independent in vivo RNA replication in animals, such as pigs, after vaccination with a vaccine comprising a nucleic acid encoding such a PRRS replicon.

PRRSV (Lelystad virus) was first isolated in 1991 by Wensvoort et al. (1991) and was shown to be the causative agent of a new disease now known as porcine reproductive respiratory syndrome (PRRS). The main symptoms of the disease are respiratory problems in pigs and abortions in sows, sometimes complicated by sow-mortality. Although the major outbreaks, such as observed at first in the US in 1987 and in Europe in 1991, have diminished, this virus, in its various virulent or less-virulent forms, still causes major economic losses in herds in the US, Europe, and Asia.

PRRSV preferentially grows in alveolar lung macrophages (Wensvoort et al., 1991). A few cell lines, such as CL2621 and other cell lines cloned from the monkey kidney cell line MA-104 are also susceptible to the virus. Some well known PRRSV strains are known under accession numbers CNCM I-1102, I-1140, I-1387, I-1388, ECACC V93070108, or ATCC VR 2332, VR 2385, VR 2386, VR 2429, VR 2474, and VR 2402. The genome of PRRSV is 15 kb in length and contains genes encoding the RNA dependent RNA polymerase (ORF1a and ORF1b) and genes encoding structural proteins (ORFs 2 to 7; Meulenberg et al., 1993 and Meulenberg et al., 1996). ORF5 encodes the major envelope glycoprotein, designated $GP_5$. The ORFs 2, 3, and 4 encode glycoproteins designated $GP_2$, $GP_3$, and $GP_4$, respectively. These glycoproteins are less abundantly present in purified virions of the Lelystad virus isolate of PRRSV. The $GP_5$ protein forms a di-sulfide-linked heterodimer with the membrane protein M encoded by ORF6. The nucleocapsid protein N is encoded by ORF7. The analysis of the genome sequence of PRRSV isolates from Europe and North America, and their reactivity with monoclonal antibodies has proven that they represent two different antigenic types. The isolates from these continents are genetically distinct and must have diverged from a common ancestor relatively long ago (Murtaugh et al., 1995).

Pigs can be infected by PRRSV via the oronasal route. Virus in the lungs is taken up by lung alveolar macrophages and in these cells replication of PRRSV is completed within 9 hours. PRRSV travels from the lungs to the lung lymphnodes within 12 hours and to peripheral lymphnodes, bone marrow and spleen within 3 days. At these sites, only a few cells stain positive for viral antigen. The virus is present in the blood during at least 21 days and often much longer. After 7 days antibodies to PRRSV are found in the blood. The combined presence of virus and antibody in PRRS infected pigs shows that the virus infection can persist for a long time, albeit at a low level, despite the presence of antibody. During at least 7 weeks the population of alveolar cells in the lungs is different from normal SPF lungs.

PRRSV needs its envelope to infect pigs via the oronasal route and the normal immune response of the pig thus entails among others the production of neutralising antibodies directed against one or more of the envelope proteins; such antibodies can render the virus non-infective. However, once in the alveolar macrophage, the virus also produces naked capsids, constructed of RNA encapsidated by the M and/or N protein, sometimes partly containing any one of the glycoproteins. The intra- and extracellular presence of these incomplete viral particles or (partly) naked capsids can be demonstrated by electron microscopy. Sometimes, naked capsids without a nucleic acid content can be found. The naked capsids are distributed through the body by the bloodstream and are taken up from the blood by macrophages in spleen, lymphnodes and bonemarrow. These naked but infectious viral capsids can not be neutralised by the antibodies generated by the pig and thus explain the persistence of the viral infection in the presence of antibody. In this way, the macrophage progeny from infected bonemarrow cells is spreading the virus infection to new sites of the body. Because not all bonemarrow macrophage-lineage cells are infected, only a small number of macrophages at peripheral sites are infected and produce virus. PRRSV capsids, consisting of ORF7 proteins only, can be formed in the absence of other viral proteins, by for instance infection of macrophages with a recombinant pseudorabies-ORF7 vector virus. The PRV virus was manipulated to contain ORF7 genetic information of PRRSV. After 18 hours post infection, the cytoplasm of infected cells contains large numbers of small, empty spherical structures with the size of PRRS virus nucleocapsids.

Although live-attenuated and killed PRRSV vaccines are now available, it has been shown that in general these are not immunogenic enough or are too virulent for specific groups of pigs, i.e. for young piglets or sows in the third trimester of pregnancy. It is clear that a PRRSV vaccine that is not sufficiently immunogenic will not stand up in the market. However, several of the existing immunogenic vaccines are not safe illustrating the need for attenuated PRRSV vaccines with reduced virulence.

Furthermore, again under specific circumstances, several of the existing vaccines spread within a population, and may inadvertently infect other pigs that need not or should not be vaccinated, illustrating the need for non-spreading PRRSV vaccines.

Furthermore, the existing vaccines can in general not be distinguished from wild type field virus, illustrating the need for a so-called marker vaccine, obtained for example by mutagenesis of the genome, so that vaccinated pigs can be distinghuished from field virus-infected pigs on the basis of differences in serum antibodies.

In addition, PRRS vaccines, being so widely used throughout the world, and being in general not infectious to other animals but pigs, would be attractive candidate vaccines to carry foreign antigens derived from other (porcine) pathogens to provide for protection against those other pathogens, illustrating the need for PRRSV carrier or vector vaccines allowing vaccination against those other pathogens or allowing positive marker identification.

It goes without saying, that PRRSV vaccines combining one or more of these features would be preferred. It is an object of the present invention to provide solutions to these needs.

The invention provides a porcine reproductive and respiratory syndrome virus (PRRSV) replicon having at least some of its original PRRSV nucleic acid deletions, herein also comprising substitutions, said replicon capable of in vivo RNA replication, said replicon further having been deprived of at least some of its original PRRSV nucleic acid and/or having been supplemented with nucleic acid derived from a heterologous micro-organism.

Surprisingly, it has been found that the genome of PRRSV can be deprived of quite a large amount of its nucleic acid. An independent and functional PRRSV replicon capable of independent in vivo RNA replication can still exist if the stretch, or fragments thereof, of nucleic acid encoding the ORF2-ORF6, but not an essential element from the ORF7 protein, is deleted and/or modified. Having a replicon wherein such a large stretch of nucleic acid has been deleted or modified opens up a large capacity for the addition to said replicon of heterologous nucleic acid from any other organism than PRRSV, thereby providing a PRRSV vector replicon with large carrier capacities. Herewith, the inventor provides identification of specific nucleic acid regions in the genome of porcine reproductive and respiratory syndrome virus, that are important for attenuation of the virus, for making it non- or little spreading or for the introduction of a marker, without crippling the viral nucleic acid so much that it can no longer provide in vivo RNA replication. Furthermore, the inventor demonstrates that a PRRSV replicon can be used as vector for the expression of foreign antigens, preferably derived from other (porcine) pathogens, allowing vaccination against those other pathogens and allowing positive marker identification.

Figure 2:
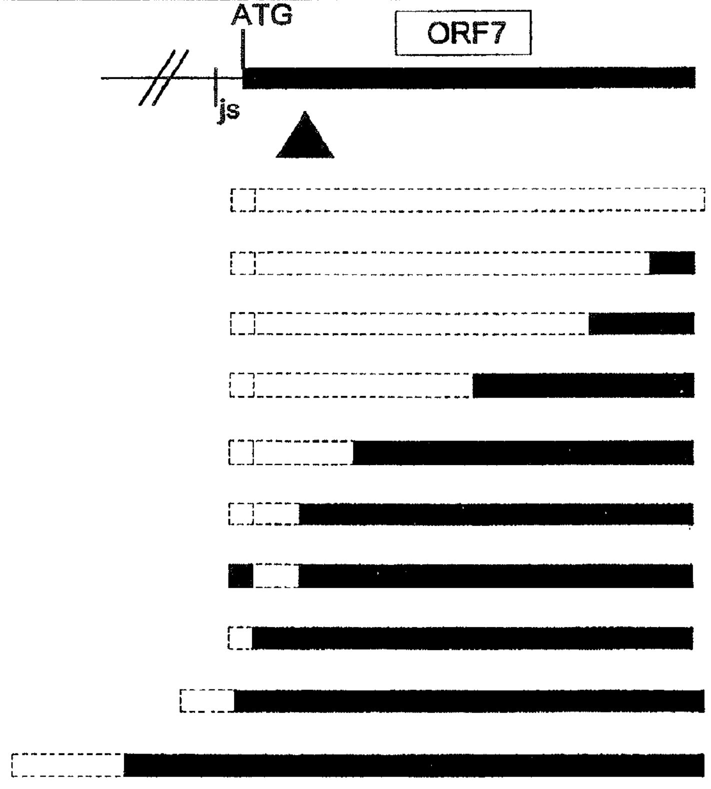

The minimal sequence requirements for a PRRSV replicon or PRRSV vector replicon as provided by the invention are essential elements comprising the 5' noncoding region-ORF1a-ORF1b-ORF7-3' noncoding region, (e.g. from the PRRSV polymerase region) whereby the ORF7 coding region can be deleted further for example according to the data shown in FIG. 2. In a preferred embodiment, the invention provides a PRRSV replicon or vector at least comprising essential elements from the PRRSV polymerase region for example as described below and/or comprising at least nucleic acid derived from a essential region of 44 nucleotides between nucleotides 14642 to 14686 in the ORF7 gene (as identified in the nucleic acid sequence of the Lelystad virus isolate of PRRSV, however, the skilled person can easily determine by alignment wherein in any other PRRSV genome said essential element is located).

In another preferred embodiment, the invention provides a PRRSV replicon comprising at least nucleic acid derived from essential sequence elements from ORF1a and ORF1b, or from the PRRSV polymerase region and having nucleic acid from ORF2, ORF 3, ORF 4, ORF 5, ORF 6, or non-essential elements from ORF7 deleted, allowing insertion of foreign nucleic acid, thereby providing a PRRSV vector replicon having foreign antigen coding capacities. This in contrast to WO08/55626 where the homologous polymerase is replaced with a heterologous Arteriviral one to express ORF2-ORF7, essentially without disclosing expression of foreign antigens derived from other (porcine) pathogens to provide for protection against those other pathogens allowing vaccination against those other pathogens (let alone wherein the PRRSV genome nucleic acid encoding foreign antigens may be located for providing a PRRSV vector replicon or which essential sequence elements should remain).

The replicase polyprotein of PRRSV encoded by ORF1 is thought to be cleaved in 13 processing end-products (designated nonstructural proteins—nsps) and a large number of intermediates. The polyprotein is cleaved by protease domains located in nsp1$\alpha$, nsp1$\beta$, nsp2 and nsp4. Essential PRRSV RNA-dependent RNA polymerase and nucleoside triphosphate-binding/RNA Helicase motifs were identified in nsp9 and nsp10, respectively. Another conserved (essential) domain was found in nsp11, a conserved Cys/His-rich domain was found in nsp10. It has for example been shown that the latter protein plays a role in subgenomic mRNA synthesis.

In a further embodiment, the invention provides a PRRSV replicon capable of independent in vivo RNA replication wherein said replicon is a RNA transcript of an infectious copy cDNA. It has been shown for many positive strand RNA viruses that their 5' and/or 3' noncoding regions contain essential signals that control the initiation of plus- and minus-strand RNA synthesis. It was not determined for PRRSV whether these sequences alone are sufficient for replication. As for most RNA viruses, PRRSV contains a concise genome and most of the genetic information is expected to be essential. Furthermore, the maximum capacity for the integration of foreign genes into the PRRSV genome is not yet known. An extra limitation is that the ORFs encoding the structural proteins of PRRSV are partially overlapping. The introduction of mutations in these overlapping regions often results in two mutant structural proteins and therefore is more often expected to produce a nonviable virus.

The production of an infectious clone allowed us to analyse replication signals in the genome of PRRSV. In this study we have mapped cis-acting sequence elements required for replication by introducing deletions in the infectious clone. Surprisingly, we have shown that also cis-acting sequence elements from the region of the genome encoding structural proteins are essential for proper replication. We have shown that transcripts derived from cDNA clones lacking the ORF7 gene are not replicated. A more systematic deletion analysis showed that a region of 44 nucleotides between nucleotides 14642 to 14686 in the ORF7 gene was essential for replication of RNA of PRRSV. This was an interesting finding, since the sequences essential for replication of most positive strand RNA viruses are present in the 5' and 3' noncoding regions. It is an important finding for studies who’s aim is to develop viral replicons which can only be rescued in complementing cell lines expressing the deleted ORFs. The minimal sequence requirements for these RNAs are located in the 5' noncoding region-ORF1a-ORF1b-ORF7-3' noncoding region. Viral RNA's or replicons containing these sequence elements supplemented with a selection of fragments from other PRRSV open reading frames or fragments of open reading frames expressing antigens of other (heterologous) pathogens can be packaged into virus particles when the proteins essential for virus assembly are supplied in trans. When these particles are given to pigs, for example as vaccine, they will enter specific host cells such as macrophages and virus- or heterologous antigens are expressed and induce immune responses because of the replicating RNA. However, since the RNA does not express (all) the proteins required for packaging and the production of new particles, the replicon can not spread further, creating an extremely efficient, but safe and not-spreading recombinant vaccine effective against PRRSV and/or heterologous pathogens.

In a preferred embodiment, the invention provides a replicon according to the invention incapable of N-protein capsid formation. For example, two Cys residues are present at positions 27 and 76 in the N protein sequence and mutating or deleting Cys-27 and Cys-76 from the N protein inhibits the production of infectious particles of PRRSV. The ORF7 gene encoding the N protein was mutated as such that the Cys residues were substituted for Asn and Leu residues, respectively, however, substitution with another amino acid, or deletion of the coding sequence, leads to the desired result as well, as for example can be seen below.

The Cys-27 and Cys-76 mutations were subsequently introduced in the infectious clone pABV437 of the Lelystad virus isolate of PRRSV, resulting in plasmids pABV534-536 (Cys-27→Asn) and pABV472-475 (Cys-76→Leu). RNA was transcribed from these mutated infectious clones and transfected to BHK-21 cells. The structural proteins were properly expressed, these mutant RNAs were replicated and subgenomic RNAs synthesized. However, infectious particles were not secreted, since the transfer of the supernatant of the transfected BHK-21 cells to macrophages did not result in the production of viral proteins in the macrophages nor in the induction of a cpe.

Thus, these residues are essential for a proper structure or function or both of the N protein in virus assembly of PRRSV. The N protein is involved in the first steps in virus assembly, the binding of the viral genomic RNA and formation of the capsid structure. Since transcripts of genomic length cDNA clones containing the Cys-27 and/or Cys-76 deletion replicated at the wild type level, the mutations in the Cys residues destroy the binding of the RNA by the N protein. Alternatively, they induce a different structure of the N protein that inhibits the formation of proper capsids. The defect in the encapsidation of the viral RNA genome can be complemented by wild type N protein transiently expressed or continuously expressed in a (BHK-21) cell line. In this way a virus is produced that is able to complete only one round of infection/replication. Therefore such a virus is considered to be a very safe vaccine for protection against PRRSV in pigs.

In another example, the invention provides a replicon incapable of N-protein capsid formation wherein substitutions in the genome encoding the N protein area containing two antigenic regions designated B and D inhibited the production of infectious virus particles. The B region (SEQ ID No. 1) comprises amino acids 25-30 (QLCQLL), D region (SEQ ID Nos. 2 and 3); amino acids 51-67 (PEKPHFPLAAEDDIRHH) and amino acids 80-90 (ISTAFNQGAGT), respectively, of the N protein of PRRSV. The corresponding sites in VR2332 and other American strains are found when the N proteins of these strains are aligned. Since RNA replication and subgenomic mARNA synthesis appeared to be at the wild type level, these mutations most likely prevented the formation of proper capsids by the N protein.

The invention furthermore provides a replicon according to the invention wherein a marker allowing serological discrimination has been introduced. For example, mutagenesis of a single amino acid in the D region (Asp-62 or a.a. corresponding thereto) of protein N results in a replicon that has a different MAb binding profile from PRRSV and all other PRRSV viruses. Such a replicon induces a different spectrum of antibodies in pigs, compared to these other PRRSV isolates. Therefore it can be differentiated from field virus on the basis of serum antibodies and is an excellent mutant for further development of marker vaccines against PRRSV.

The above example involves a subtle modification resulting in a replicon useful for a marker vaccine. However, more extensive changes are now also possible, knowing that it is allowed to partly or fully delete the nucleic acid encoding the structural proteins 2, 3, 4, 5, and/or 6 without tampering with the replicative properties of the resulting replicon. A PRRSV replicon lacking one or more (antigenic) fragments of these structural proteins has the advantage that no immune respons, more specifically no antibodies, against these deleted fragments will be formed, for example after vaccination with a vaccine comprising such a replicon. Again, such a replicon induces a different spectrum of antibodies in pigs, compared to wild type PRRSV. Therefore it can be differentiated from field virus on the basis of serum antibodies and is an excellent mutant for further development of marker vaccines against PRRSV.

Furthermore, the invention provides a replicon comprising a nucleic acid modification in a virulence marker of PRRSV. Virulence markers of PRRSV have not been elucidated, despite the fact that various differences in virulence have been observed. However, for successfully attenuating a PRRSV or replicon thereof, such knowledge helps in selecting the least virulent, but most immunogenic replicon or virus possible. Now that it is known that deleting or modifying the ORF2 to ORF 6 region is possible without effecting the in vivo RNA replicative properties, such virulence markers can easily be detected. For example, the invention provides replicon comprising a nucleic acid modification in ORF 6 encoding the membrane spanning M-protein. It has been found that the membrane protein is influencing the virus assembly, the stability of the virus, or the virus entry in macrophages, all factors contributing to the virulence of PRRSV. The M protein is the most conserved structural protein among arteriviruses and coronaviruses. The protein is an integral membrane protein containing three N-terminal hydrophobic membrane spanning domains (Rottier, 1995). The protein spans the membrane three times leaving a short N-terminal domain outside the virion and a short C-terminal domain inside the virion. The M protein of coronaviruses was shown to play an important role in virus assembly (Vennema et al., 1996), but was then not determined to be a virulence factor. In particular, the invention provides a replicon wherein said modification modifies protein M in between its second and third membrane spanning fragment, essential in determining virulence of a specific PRRSV isolate. For example, the invention provides a replicon comprising vABV575. A Thr-59→Asn mutation is located between the second and third membrane spanning fragment of M in vABV575. This mutation influences virus assembly, the stability of the virus, or virus entry in the PAMs.

The invention furthermore provides a replicon according to the invention wherein said heterologous micro-organism comprises a pathogen. Since PRRSV specifically infects macrophages, it can be used as a vector for the delivery of important antigens of other (respiratory) agents to this specific cell of the immune system. The infectious cDNA clone enables us to introduce site specific mutations, deletions and insertions into the viral genome.

In a preferred embodiment, the invention provides a replicon wherein said pathogen is a virus. We have successfully used PRRSV as a vector for the expression of a foreign protein anigen, an HA epitope of the haemagglutinin of influenza A virus. Recombinant PRRSV vector replicons were engineered that produced the HA tag fused to the N- or C-terminus of the N protein. In addition, an PRRSV mutant was created that contained the HA-tag as well as the protease 2A of foot-and-mouth-disease virus (FMDV) fused to the N terminus of the N protein.

Furthermore, the invention provides a vaccine comprising a replicon or vector replicon according to the invention. PRRSV vaccines are now provided with specified antigenicity or immunogenicity that are in for example in addition safe enough for specific groups of pigs, i.e. for young piglets or sows in the third trimester of pregnancy.

Furthermore, the invention provides non-spreading PRRSV vaccines, comprising a replicon or vector replicon for example incapable of N-protein capsid formation, or incapable of further infection due to the absence of (fragments of) structural proteins encoded by ORF 2 to 6, without hampering its in vivo RNA replication properties, thereby allowing the production of proteins against which an immune response is desired.

Furthermore, the invention provides a vaccine that can be distinguished from wild type field virus, a so-called marker vaccine, obtained for example by mutagenesis of the genome, so that vaccinated pigs can be distinguished from field virus-infected pigs on the basis of differences in serum antibodies.

In addition, PRRS vaccines, being so widely used throughout the world, and being in general not infectious to other animals but pigs, are now provided as vector vaccines to carry foreign antigens derived from other (porcine) pathogens, allowing vaccination against those other pathogens and allowing positive marker identification.

Use of a vaccine according to the invention is especially useful for vaccinating pigs, sine the PRRSV is in general very host specific and replicates in macrophages of pigs, thereby targeting an important antigen presenting cell of the immune system.

The invention is further explained in the detailed description, without limiting the invention.

DETAILED DESCRIPTION

1. Mutation of Cys-27 and Cys-76 in the N Protein Inhibits the Production of Infectious Particles of PRRSV The nucleocapsid protein N (expressed by ORF7) is present as a monomer in purified virions of PRRSV. However, in some experiments we also detected a homodimer of N. For instance when the N protein was immunoprecipitated from purified virions with N-specific MAbs and electrophorezed on a sodium dodecyl sulfate polyacrylamide gel (SDS-PAGE), a protein of 15 kDa was predominantly observed under reduced conditions, whereas a homodimer of 30 kDa was predominantly observed under nonreduced conditions (Meulenberg et al., 1996). However, when compounds such as N-methyl maleimide or iodoacetamide were used to prevent the formation of nonspecific disulfide bonds, these dimers of N were not detected. This indicated that dimers of N are formed due to the formation of nonspecific disulfide bonds during the processing of cell lysates for analysis. Two cystein residues are present in the N protein sequence. The question raised which of the cysteine residues was responsible for the formation of nonspecific disulfide bonds and whether the cysteine residues are important for the structure and function of the N protein. To answer this question we mutated the two cystein residues individually in the infectious cDNA clone of PRRSV and studied the infectivity of the resulting mutant viral genomic RNAs.

2. Introduction of a Marker in the N Protein

The N protein of PRRSV contains 4 antigenic sites, designated A-D (Meulenberg et al., 1998). Two sites, B and D, contain epitopes that are conserved in European and North American isolates of PRRSV. To produce viruses that can be serologically distinguished from wild type viruses, mutations in the B and D domain that disrupt the binding of N-specific MAbs were introduced in the infectious cDNA clone of PRRSV. Transcripts of the resulting mutant full length cDNA clones were analyzed for RNA replication by detecting the expression of structural proteins and production of infectious virus.

3. Elucidation of Replication Signals Present in the Region Encoding Structural Proteins of Lelystad Virus Positive strand RNA viruses contain 5' and 3' noncoding regions which are essential for replication. The RNA sequences at the 5' and 3' end usually have a specific secondary structure which is recognized by the viral RNA dependent RNA polymerase to initiate positive and negative strand synthesis and in the case of arteriviruses subgenomic RNA synthesis. We deleted the ORF7 gene from the infectious clone of PRRSV (Meulenberg et al., 1998) in a first attempt to generate a defective RNA replicon that could be complemented for production of infectious particles, when transfected to a cell expressing the N protein. The ORF7 gene was precisely deleted, without affecting the 3' noncoding region of the virus. Surprisingly, the RNA of this deletion mutant did not replicate in BHK-21 cells. This suggested that RNA replication signals are present in the coding region of ORF7. The purpose of this study was to further localize these replication signals. By extensive deletion analysis of the coding region and upstream sequences of ORF7 we were able to identify a region of 44 nucleotides in the ORF7 gene that is important for replication of RNA of PRRSV.

4. Production of an Attenuated PRRSV Virus by Deletion of the NdeI Site in ORF6.

Recently, we have established an infectious clone cDNA clone of PRRSV (Meulenberg et al., 1998). The full length cDNA clone contains two NdeI sites, the first at nucleotide 12559 (ORF3) and the second at nucleotide 14265 (in ORF6) in the genome sequence. To facilitate mutagenesis and exchange of fragments in the region encoding the structural proteins (ORFs 2 to 7) of the virus, we destroyed the second NdeI site by PCR-directed mutagenesis. This resulted in an amino acid substitution at position 59 in the M protein (Thr→Asn). The growth properties of the virus produced from the mutated full length cDNA clone containing a unique NdeI site was analysed.

5. Lelystad Virus as a Vector for the Expression of Foreign Antigens or Proteins.

The generation of an infectious cDNA clone of PRRSV (Meulenberg et al., 1998) is a major breakthrough in PRRSV research and opens up new possibilities for the development of new viral vectors. Since PRRSV specifically infects macrophages, it can be used as a vector for the delivery of important antigens of other (respiratory) agents to this specific cell of the immune system. The infectious cDNA clone enables us to introduce site specific mutations, deletions and insertions into the viral genome. However, it is still not known which regions of the PRRSV genome are essential or allow mutagenesis. As for most RNA viruses, PRRSV contains a concise genome and most of the genetic information is expected to be essential. Furthermore, the maximum capacity for the integration of foreign genes into the PRRSV genome is not yet known. An extra limitation is that the ORFs encoding the structural proteins of PRRSV are partially overlapping. The introduction of mutations in these overlapping regions results in two mutant structural proteins and therefore is more often expected to produce a nonviable virus.

The aim of this study was to identify regions in the PRRSV genome that allow the introduction of foreign antigens that will be exposed to the immune system of the pig after infection with the mutant virus. In a first approach we have selected a small epitope of 9 amino acids of human haemagglutinin of influenza A for expression in PRRSV.

Methods

Cells and Viruses

BHK-21 cells were grown in BHK-21 medium (Gibco BRL), completed with 5% FBS, 10% tryptose phosphate broth (Gibco BRL), 20 mM Hepes pH 7.4 (Gibco BRL) and 200 mM glutamine, 100 U/ml penicillin and 100 μg/ml streptomycin. Porcine alveolar lung macrophages (PAMs) were maintained in MCA-RPMI-1640 medium, containing 10% FBS, 100 μg/ml kanamycin, 200 U/ml penicillin and 200 μg/ml streptomycin. Virus stocks were produced by serial passage of recombinant PRRSV viruses secreted in the culture supernatant of tranfected BHK-21 cells on PAMs. Virus was harvested when PAMs displayed cytopathic effect (cpe) usually 48 hours after infection. Virus titers (expressed as 50% tissue culture infective doses [$TCID_{50}$] per ml) were determined on PAMs using end point dilution (Wensvoort et al., 1986).

Mutagenesis

1. Mutagenesis of Cys-27 and Cys-76.

The Cys-27 was mutated to Asn by PCR-directed mutagenesis with primers LV108 and LV97. The sequences of primers used in this study are listed in Table 1. The generated PCR fragment was digested with HpaI and PflmI and inserted in the ORF7 gene in pABV431 digested with the same enzymes. This resulted in plasmid pABV451 The Cys-76 was mutated to Leu by PCR-directed mutagenesis with primers LV108 and LV100. The generated fragment was digested with HpaI and ClaI and inserted in the ORF7 gene in pABV431 digested with the same enzymes. This resulted in pABV452. The mutated ORF7 genes were subsequently transferred to the genomic-length cDNA clone pABV437(Meulenberg et al., 1998) with the unique HpaI (nt 14581) and PacI (nt 14981) site, to create plasmids pABV534-536 (Cys-27→Asn) and plasmids pABV472-475 (Cys-76→Leu; FIG. 1).

2. Mutagenesis of Antigenic Site B and D in the N Protein

Antigenic sites B (amino acids 25-30) and D (amino acids 51-67 and 80-90) of the N protein of PRRSV were mutated by substitution of the amino acids in this region for the corresponding amino acids of respectively EAV and LDV. Plasmids pABV455, pABV463, and pABV453 containing these respective mutation were described previously in Meulenberg et al. (1998). In addition, the Asp at position 62 in the D region of the N protein was mutated to a Tyr in a PCR with primers LV108 and LV188. The sequences of these primers are shown in Table 1. The PCR fragment was digested with HpaI and ClaI and inserted in the ORF7 gene in pABV431 digested with the same enzymes. This resulted in pABV582. The ORF7 genes containing the mutations were inserted in pABV437 using the unique HpaI (nt 14581) and PacI (nt 14981) (FIG. 1).

3: Creation of Deletion Mutants in the Full-Length cDNA Clone of PRRSV

Several deletions were made in the full-length cDNA clone of pABV437 of PRRSV (FIG. 2). First, ORF2, ORF3, ORF4, ORF5 and the 5' half of ORF6 were deleted. pABV437 was digested with EcoRI and NheI and the sites were made blunt with Klenow fragment (Pharmacia Biotech). The fragment was purified and ligated. This resulted in clone plasmid pABV594. Second, ORF7 was deleted from the infectious copy of PRRSV. For this purpose, the infectious full-length cDNA clone pABV442 that contains a SwaI restriction site directly downstream of the stopcodon of ORF7, was digested with HpaI and SwaI and ligated. This resulted in clone plasmid pABV521. Third, to delete the 3' end of ORF6, PCR-mutagenesis was performed with primers LV198 and LV199. The primers used in PCR-mutagenesis are listed and described in Table 1. The generated product was digested with HpaI and NheI and ligated in the corresponding sites of pABV437. This resulted in plasmid pABV627. Fourth, several deletions in and upstream of the coding region of ORF7 were made. PCR-mutagenesis was performed with forward primers LV188-191 or LV195-197 and reversed primer LV112. The generated products were digested with HpaI and PacI and ligated in the same restriction sites of pABV437, resulting in plasmids pABV602-605 and pABV625-627. Plasmids were transformed to *Escherichia coli* DH5α and grown at 32° C. and 20 μg kanamycin per ml. For each construct two clones containing fragments of two independent PCRs were sequenced to confirm the correct sequence of the clones. The resultant mutants are shown in FIG. 2.

4. Mutagenesis of the NdeI Site at Position 14265 in the Infectious cDNA Clone pABV437 of PRRSV To mutate the NdeI site at position 14265 a fragment of 1.7 kb was amplified by PCR using primers LV27 (nt 12526) and LV182 (nt 14257; Table 1) Primer LV182 contains an AseI site. AseI and NdeI have compatible ends, but ligation of their ends to each other destroys both restriction sites. The PCR fragment was digested with NdeI and AseI and ligated in pABV437 digested with NdeI. The full length clone pABV575 (FIG. 3) that contained the PCR fragment in the proper orientation, lacked the NdeI site at position 14265 and had no other mutations between 12559 and 14265 due to PCR errors was selected for further analysis.

Figure 4:
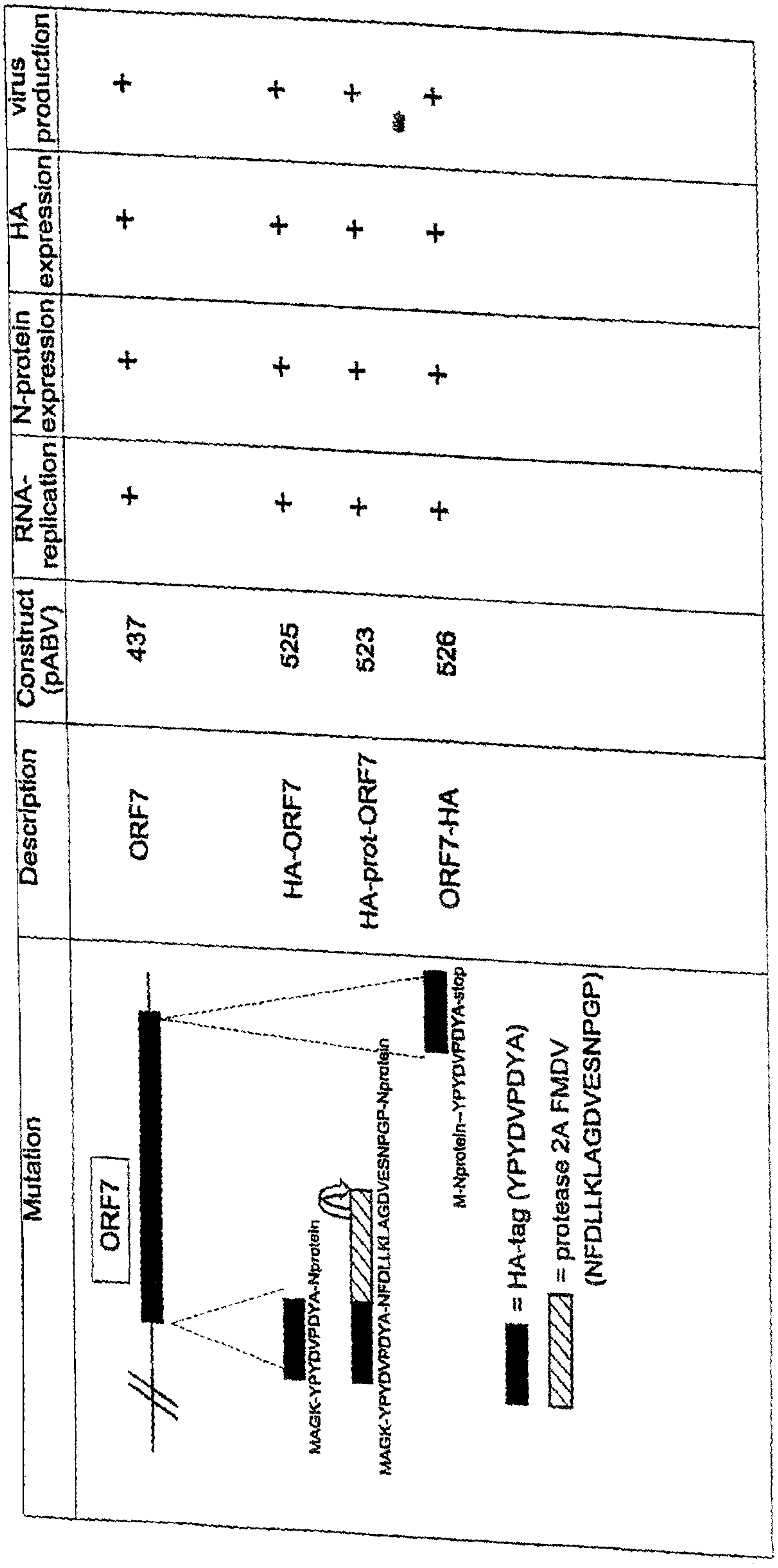

5: Construction of Full-Length Genomic cDNA Mutants of PRRSV Encoding an Antigenic HA tag PCR-mutagenesis was used to create mutants in the infectious clone of PRRSV. First, a sequence of 27 nucleotides encoding an epitope of the human haemagglutinin of influenza A (HA-tag; Kolodziej et al., 1991) was introduced directly downstream of the start codon of ORF7 in the PacI mutant of the genome-length cDNA clone of Lelystad Virus (pABV437; Meulenberg et al., 1998). Two sequential PCRs were performed with primers LV192 and LV112 and with primers LV193 and LV112. Primers used to create the PCR-fragments are listed and described in Table 1. Second, both this HA-tag and a sequence of 51 nucleotides encoding the protease 2A of FMDV (Percy et al., 1994) were introduced directly downstream of the startcodon of ORF7. Two sequential PCR-reactions were performed with primers LV139 and LV112 and with LV140 and LV112. Third, the HA-tag was introduced at the 3' end of the ORF7 gene in a PCR with primers LV108 and LV194. The three PCR fragments obtained were digested with HpaI and PacI and ligated into pABV437 digested with the same enzymes. Standard cloning procedures were performed essentially as described in Sambrook et al., (1989). Plasmids were transformed into *Escherichia coli* DH5α and grown at 32° C. and 20 μg kanamycin per ml. For each construct two clones containing fragments of two independent PCRs were sequenced to confirm the correct sequence of the clones. Introduction of the HA epitope at the 5' end of ORF7 resulted in the generation of clone pABV525, introduction of both the HA-tag and the protease 2A at the 5' end of ORF7 resulted in clone pABV523, and the introduction of the HA-epitope at the 3' end of ORF7 resulted in clone pABV526 (FIG. 4).

Sequence Analysis

The generated cDNA clones were analyzed by oligonucleotide sequencing. Oligonucleotide sequences were determined with the PRISM Ready Dye Deoxy Terminator cycle sequencing kit and the automatic sequencer (Applied Biosystems).

In Vitro Transcription and Transfection of RNA

Full-length genomic cDNA clones and derivatives thereof were linearized with PvuI, which is located directly downstream of the poly(A) stretch. The linearized plasmids were precipitated with ethanol and 1.5 μg of these plasmids was used for in vitro transcription with T7 RNA polymerase by the methods described for SFV by Liljeström and Garoff (1991). The in vitro transcribed RNA was precipitated with isopropanol, washed with 70% ethanol and stored at −20° C. until use.

BHK-21 cells were seeded in 35-mm wells (approximately $10^6$ cells/well) and were transfected with 2.5 μg in vitro transcribed RNA mixed with 10 ml lipofectin in optimem as described earlier (Meulenberg et al., 1998). Alternatively, RNA was introduced in BHK-21 cells in 20-mm wells with 0.5 μg in vitro transcribed RNA mixed with 2 ml lipofectin in optimem. The medium was harvested 24 h after transfection, and transferred to CL2621 cells or PAMs to rescue infectious virus. Transfected and infected cells were tested for expression of PRRSV proteins by an immunoperoxidase monolayer assay (IPMA), essentially as described by Wensvoort et al. (1986). Monoclonal antibodies (MAbs) 122.14, 122.1, and 126.3 directed against respectively the $GP_3$, $GP_4$, M protein (van Nieuwstadt et al., 1996) were used for staining in this assay. A panel of MAbs (122.17, 125.1, 126.9, 126.15, 130.2, 130.4, 131.7, 131.9, 138.22, WBE1, WBE4, WBE5, WBE6, SDOW17, NS95, and NS99) directed to four different antigenic sites A-D were used to study the expression of the N protein (Meulenberg et al., 1998). MAb 12CA5 was used to detect the expression of the HA-epitope and was purchased from Boehringer Mannheim. In addition, we analyzed the expression of PRRSV proteins by metabolic labeling of transfected or infected cells, followed by immunoprecipitation using specific monoclonal antibodies or peptide sera directed to the structural proteins of PRRSV, as described by Meulenberg et al (1996).

Sequence Analysis of Genomic RNA of Recombinant Viruses

The culture supernatant of the PAMs infected with passage 3 of the HA-expressing viruses was used to analyze viral RNA by RT-PCR. A volume of 500 μl proteinase K buffer (100 mM Tris-HCl [pH 7.2], 25 mM EDTA, 300 mM NaCl, 2% [wt/vol] sodium dodecyl sulfate) and 0.2 mg Proteinase K was added to 500 μl supernatant. After incubation for 30 minutes at 37° C., the RNA was extracted with phenol-chloroform and precipitated with ethanol. The RNA was reverse transcibed with primer LV76. Then, PCR was performed with primers LV37 and LV112 to amplify fragments of vABV523 and vABV525 and with primers LV37 and LV75 to amplify fragments of vABV526 (Table 1). Sequence analysis was performed to determine whether the mutant viruses at passage 4 still contained the inserted foreign sequences.

Results

1. Mutation of Cys-27 and Cys-76 in Full Length cDNA Clone pABV437

Two Cys residues are present at positions 27 and 76 in the N protein sequence. The ORF7 gene encoding the N protein was mutated as such that the Cys residues were substituted for Asn and Leu residues, respectively. The Cys-27 and Cys-76 mutations were subsequently introduced in the infectious clone pABV437 of the Lelystad virus isolate of PRRSV, resulting in plasmids pABV534-536 (Cys-27→Asn) and pABV472-475 (Cys-76→Leu; FIG. 1). RNA was transcribed from these mutated infectious clones and transfected to BHK-21 cells. These cells stained positive with N-specific MAbs in IPMA. Analysis of the N protein synthesized by pABV534-536 and pABV472-475 in immuno precipitation and SDS-PAGE indicated that its apparent molecular weight was similar to the wild type N protein and migrated at 15 kDa under reducing conditions. Next we analyzed the N protein under nonreducing conditions in the absence of N-methyl maleimide or iodoacetamide. Under these conditions, the N protein expressed by pABV472-475 (Cys-76→Leu) resembled the wild type N protein and was mainly detected as a dimer, whereas the N protein expressed by pABV534-536 (Cys-27→Asn) was detected as a monomer. This indicated that the Cys residue at position 27 was responsible for the formation of nonspecific disulfide bonds. The production of other structural proteins such as $GP_3$, $GP_4$, and M was also detected in IPMA and immune precipitation after transfection of full length RNA from plasmids pABV534-536 (Cys-27→Asn) and pABV472-475 (Cys-76→Leu: FIG. 1). Since the structural proteins were properly expressed, these mutant RNAs were replicated and subgenomic RNAs synthesized. However, infectious particles were not secreted, since the transfer of the supernatant of the transfected BHK-21 cells to PAMs did not result in the production of viral proteins in the PAMs nor in the induction of a cpe. Therefore both Cys residues are essential for a proper structure or function or both of the N protein in virus assembly.

2. Characterization of Full Length cDNA Clones Containing Mutations in Antigenic Sites of the N Protein of PRRSV Site B (amino acids 25-30) and D (amino acids 51-67 and 80-90) are two antigenic regions that are conserved in European and North American PRRSV isolates. When we mutated site B and D by substituting their amino acid sequence for the corresponding amino acids of the LDV or EAV N protein, the binding of the N protein by respectively B-specific and D-specfic MAbs was disrupted (Meulenberg et al., 1998). To produce a PRRSV virus that is antigenically different from PRRSV field viruses, we introduced the ORF7 genes containing a mutated B or D region in our infectious clone pABV437. This resulted in pABV527-533, containing a mutated B site (amino acids 25-30), pABV537-539 containing a mutated D domain (amino acids 51-67), and pABV512-515 containing a mutated D domain (amino acids 80-90) (FIG. 1). When RNA of these full length clones was transfected to BHK-21 cells, these cells stained positive with N-specific MAbs at 24 h after transfection. As expected, the N protein expressed by pABV527-533 was recognized by A-, C-, and D-specific MAbs, but not by B-specific MAbs. On the other hand the N protein expressed by pABV537-539 and pABV512-515 was recognized by A-, B-, and C-specific MAbs but not by D-specific MAbs. The staining of cells transfected with the RNA derived from pABV527-533, pABV537-539 and pABV512-515 with MAbs directed against $GP_3$, $GP_4$, and M, was similar to that observed in transfections with RNA derived from wild type pABV437. This suggested that RNA replication and subgenomic mRNA synthesis were not affected by the mutations. When the supernatant of the cells transfected with RNA derived from pABV527-533, pABV537-539 and pABV512-515 was transferred to PAMS, cpe was not produced. Most likely, the mutations in the B and D region destroyed the function of the N protein in the formation of a proper capsid structure.

Since the mutation of 4 amino acids in domain B and 5 or 9 amino acids in domain D did not allow the generation of infectious particles we then created a more subtle mutation of 1 amino acid in the D region. We introduced an Asp-62 to Tyr mutation in the N-protein in the infectious clone of PRRSV. The amino acid Asp-62 in the PRRSV N protein was mutated to Tyr by PCR directed mutagenesis and transferred to pABV437, resulting in pABV600. RNA transcribed from pABV600 was tranfected to BHK-21 cells. These cells stained positive with MAbs directed against $GP_3$, $GP_4$, M and N. At 24 h after transfection, suggesting that the RNA was replicated and subgenomic mRNAs were synthesized. When the supernatant of the BHK-21 cells transfected with transcripts from pABV600 was transferred to PAMs, cpe was detected at 2-3 days after inoculation. The infected cells stained positive with PRRSV specific MAbs, which further confirmed that infectious virus was produced. Therefore, the mutation of Asp-62 to Tyr in the N protein is tolerated in the virus and does not destroy the function of the N protein. The mutant virus vABV600 was further typed with a panel of N-specific MAbs (Table 2). Not only the binding of D-specific MAb SDOW17, but also the binding of D-specific MAbs 130.2, 130.4, 131.7, and 131.9 and WBE1 to vABV600 was greatly reduced. If hybridoma culture supernatant of these MAbs was diluted to 0.3-0.5 μg IgG/ml bright staining was observed for wild type PRRSV, but no staining could be observed for vABV600. However, when the IgG of MAbs 130.2, 130.4, 131.7, and 131.9 was purified and used more concentrated (10 μg IgG/ml) faint staining was observed. Staining of vABV600 with A- and B-specific MAbs was comparable to PRRSV. These data indicated that we have created a virus that is antigenically different from wild type PRRSV or North American PRRS viruses.

3: Identification of Replication Signals at the 3' End of the PRRSV Genome

In order to determine cis-acting sequences that are essential signals for RNA replication (plus and/or minus strand synthesis and/or subgenomic mRNA synthesis), several deletions were made in the infectious cDNA clone and transcripts derived from these deletion mutants were analysed for replication in BHK-21 cells. When transcripts from pABV521, lacking the entire ORF7 gene were transfected to BHK-21 cells, the expression of the N-protein could not be detected in IPMA (FIG. 2). Interestingly, these transcripts were also defective in the expression of other structural proteins, such as $GP_3$, $GP_4$ and M. This indicated that these RNAs were not replicated and did not produce subgenomic mRNAs. On the other hand, the deletion of ORF2, ORF3, ORF4, ORF5 and the 5' end ORF6 from the infectious copy (pABV594) resulted in viral RNA that was still capable of replication. Therefore, replication signals are present in the coding region of ORF7 and not in the coding region of ORF's 2-6. To test this and further locate the regions involved in replication, mutants containing smaller deletions in ORF7 were constructed. The transcripts of these constructs were tested for their ability to replicate by detecting the expression of PRRSV proteins in IPMA of transfected BHK-cells (FIG. 2). From these results, it could be concluded that essential signals for replication of the PRRSV genome are present between nucleotides 14643 to 14687. Viral RNAs lacking this region were defective in replication.

4. Analysis of Full Length cDNA Clone pABV575 Lacking the NdeI Site in ORF6

Figure 3:
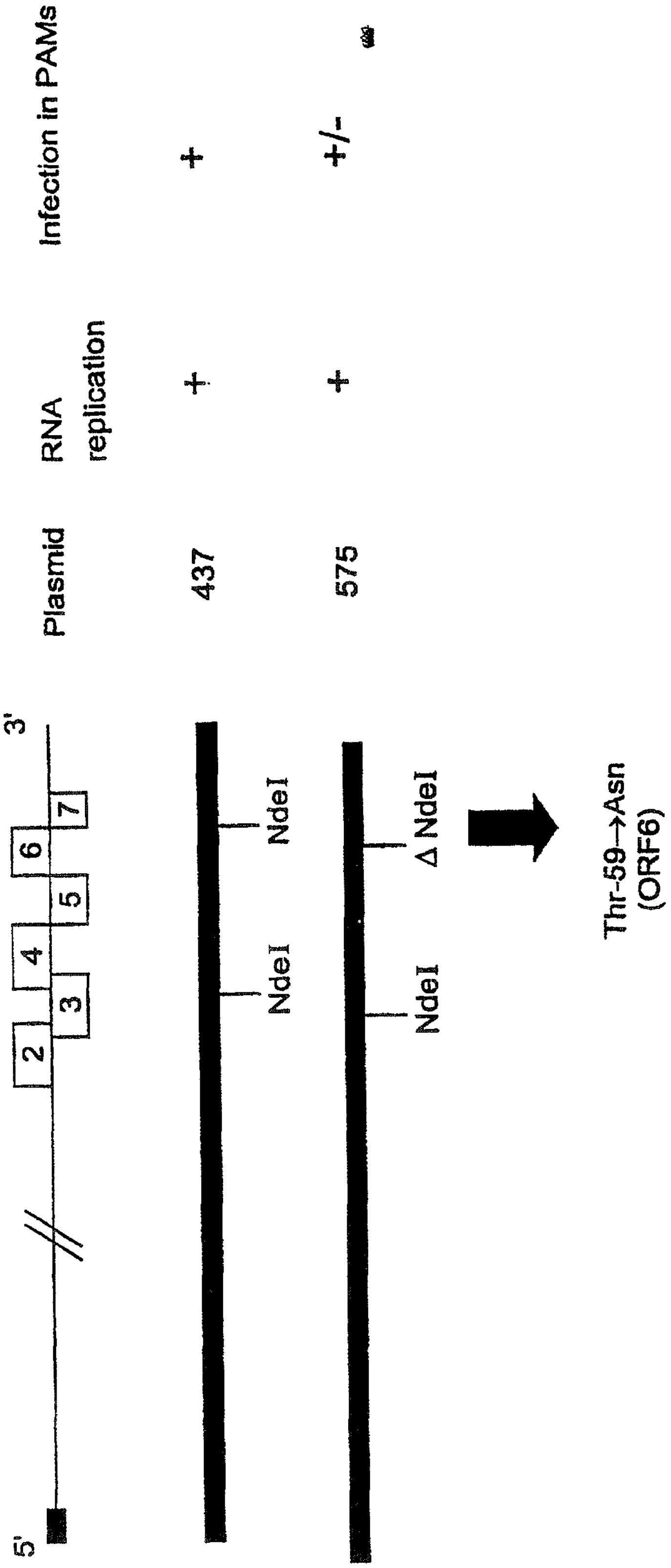

A full length cDNA clone, pABV575, was created that had a unique NdeI site at position 12559 due to mutation of the second NdeI site at position 14265 by PCR. RNA was produced from pABV575 and transfected to BHK-21 cells together with RNA from its parent clone pABV437. At 24 h after transfection with pABV575 RNA and pABV437 RNA an equal number of cells stained positive in IPMA with M-specific and N-specific MAbs (FIG. 3). Furthermore, the intensity of the staining was similar. However, when the supernatant of the transfected BHK-21 cells was transferred to PAMs and incubated for 24 h, the number of cells infected by vABV575 was much lower than that observed for vABV437. Furthermore, the cpe developed much slower in the PAMs inoculated with vABV575 than with vABV437. Although the replication of the RNA and synthesis of the subgenomic RNAs of vABV575 in BHK-21 appeared to be at the wild type level, the virus that is produced was less infectious for macrophages. This was most likely due to the amino acid mutation in the M protein (Thr→Asn) that resulted from the destruction of the NdeI site at position 14265.

5: Introduction of an HA-tag in the Infectious Clone of PRRSV

An epitope of the haemagglutinin of influenza A (HA-tag; Kolodziej et al., 1991) was expressed by different recombinant PRRSV viruses. The HA epitope was chosen as foreign antigen for expression in PRRSV mainly for two reasons; First, the tag has a limited size (27 nucleotides), which reduces the chance to disturb the replication of the virus or the expression or function of the protein to which it is fused. Second, antibodies to detect the expression of this epitope are available. The HA-tag was introduced at the 5' end of ORF7 (pABV525), and at the 3' end of ORF7 (pABV526; FIG. 4) as such that it did not induce mutations in other ORFs. We expected to get high expression of the foreign antigen by inserting it in the ORF7 gene, because subgenomic messenger RNA7 (encoding ORF7) is most abundantly produced in infected cells. Since we could not predict the influence of the HA-epitope on the function and the structure of the N protein, we created an additional in frame insertion of the 16-amino acid self-cleaving 2A protease of foot-and-mouth disease virus (FMDV; Percy et al., 1994). This protease was introduced downstream of the HA-tag at the 5' end of ORF7, which resulted in clone pABV523 (FIG. 4). We expected that this would result in the expression of a polyprotein, which could be proteolytically cleaved to release both the HA-tag and the N-protein.

5. Analysis of Recombinants of PRRSV Expressing the HA Epitope

First, the expression of the structural proteins by the various transcripts from the recombinant full-length cDNA clones was tested in IPMA. BHK-21 cells, transfected with transcripts of pABV523, 525, and 526 stained positive with MAbs directed against $GP_3$, $GP_4$, the M protein, and the N protein, which indicated that these PRRSV proteins were properly expressed (FIG. 4). The cells also stained positive with a MAb directed against HA, indicating that the HA epitope was expressed by all three RNAs. Therefore, the HA-expressing transcripts replicated in BHK-21 cells. In addition, the N-protein to which the HA-tag was fused was still expressed by the mutant RNAs.

To examine whether the transcripts of pABV523, 525 and 526 were able to produce infectious virus, the culture supernatant of transfected BHK-21 cells was used to infect PAMs.

PAMs not only stained positive with MAbs directed against the PRRSV proteins GP3, GP4, M protein and N protein in IPMA, but also with MAb 12CA5 directed against the HA epitope. However, when PAMs were double stained, both with MAbs against the HA-tag and the N protein, we also detected PAMs which could only be stained with the MAb against the N protein but not with that against the HA-tag. For viruses derived from pABV525 and pABV526 the percentage of cells that stained only with N-specific Mabs was higher than for the viruses derived form pABV523, which contained the additional protease 2A. This indicated that the HA-tag directly attached to the N- or C-terminus of the N protein disturbed to some extent either the packaging of the viral RNA or the infectivity of the virus. However, when the protease 2A was introduced to cleave the HA-tag from the N protein by the protease 2A, the fitness of the resulting virus (vABV523) was not or hardly reduced (FIG. 4). The recombinant viruses were designated vABV523, vABV525 and vABV526.

Analysis of Protease 2A Activity in vABV523

The activity of the protease 2A was further analyzed by radioimmunoprecipitation. Besides a 15 kDa protein, an additional protein of approximately 18 kDa was immunoprecipitated with N-specific MAb 122.17 from cells transfected with transcripts of pABV523. The 15 kDa protein was similar in size to the wild type N protein; the 18 kDa protein resembled the expected size of the polyprotein of HA-protease 2A-N. These data indicated that protease 2A of FMDV is able to cleave the HA-protease 2A-N polyprotein in the cell, which results in the release of the HA-tag from the N protein.

5. Growth Characteristics of HA-Expressing Viruses

The amount of virus produced by BKH-21 cells transfected with transcripts from pABV437 and pABV523 was generally higher than that produced by BHK-21 cells transfected with transcripts from pABV525 and pABV526.

Serial passage of HA-expressing viruses on PAMs resulted in stocks of vABV523, vABV525, and vABV526 with titers of approximately $10^7$ $TCID_{50}$/ml. It needs to be resolved whether the HA-expressing viruses have the same growth properties as the wild type virus of the infectious copy of PRRSV (vABV437). This will be studied in growth curves.

5. Analysis of the Stability of HA-Expressing Viruses.

To determine the stability of HA-expressing viruses, viral RNA was examined at passage 4. For this purpose, RT-PCR was performed on isolated viral RNA. Part of the ORF7 gene, the site at which the HA-tag was inserted, was amplified by PCR and the obtained fragments were analyzed on agarose gel. We obtained two fragments for vABV523 and vABV525 and one fragment for vABV526. Sequence analysis of the most abundantly amplified fragment showed that vABV523 at passage 4 still contained the properly inserted nucleotide sequence encoding the HA-tag and the protease 2A gene. In contrast, both vABV525 and vABV526 had lost the inserted nucleotide sequence encoding the HA-tag.

1. Mutation of Cys-27 and Cys-76 in the N Protein Inhibits the Production of Infectious Particles of PRRSV In this study we have found that mutation of Cys-27→Asn and Cys-76→Leu in the N protein of PRRSV interferes with the production of infectious particles in BHK-21 cells. We conclude that these residues are essential for a proper structure or function or both of the N protein in virus assembly of PRRSV. The N protein is involved in the first steps in virus assembly, the binding of the viral genomic RNA and formation of the capsid structure. Since transcripts of genomic length cDNA clones containing the Cys-27→Asn and Cys-76→Leu replicated at the wild type level, the mutations in the Cys residues destroy the binding of the RNA by the N protein. Alternatively, they induce a different structure of the N protein that inhibits the formation of proper capsids. The defect in the encapsidation of the viral RNA genome can be complemented by wild type N protein transiently expressed or continuously expressed in a (BHK-21) cell line. In this way a virus is produced that is able to complete only one round of infection/replication. Therefore such a virus is considered to be a very safe vaccine for protection against PRRSV in pigs.

2. Introduction of a Marker in the N Protein of PRRSV.

The aim of this study was to create mutant PRRS viruses that can be serologically differentiated from field virus and therefore may be promising mutants for marker vaccine development against PRRSV. The N protein was chosen as a first candidate for mutagenesis to create a virus with a serologic marker since many studies have shown that the N protein is the most antigenic protein of PRRSV. For example, pigs infected with PRRSV develop strong antibody responses against the N protein of PRRSV (Meulenberg et al., 1995). In addition, the N protein contains two antigenic regions designated B and D that are conserved in European and US PRRSV isolates and MAbs directed to these regions are available (Meulenberg et al., 1998). Here, we have demonstrated that mutation of 4 amino acids in site B to corresponding amino acids of the EAV N protein and mutation of 5 or 9 amino acids in domain D to corresponding amino acids of the LDV N protein inhibited the production of infectious virus particles. Since RNA replication and subgenomic mRNA synthesis appeared to be at the wild type level, these mutations most likely prevented the formation of proper capsids by the N protein. However, mutagenesis of a single amino acid in the D region (Asp-62→Tyr) resulted in virus vABV600 that had a different MAb binding profile from PRRSV and all other PRRSV viruses. vABV600 induces a different spectrum of antibodies in pigs, compared to these other PRRSV isolates. Therefore vABV600 can be differentiated from field virus on the basis of serum antibodies and is an excellent mutant for further development of marker vaccines against PRRSV.

3: Elucidation of Replication Signals in ORF7 of Lelystad Virus

It has been shown for many positive strand RNA viruses that their 5' and/or 3' noncoding regions contain essential signals that control the initiation of plus- and minus-strand RNA synthesis. It was not yet determined for PRRSV whether these sequences alone are sufficient for replication. The production of an infectious clone allowed us to analyse replication signals in the genome of PRRSV. In this study we have mapped cis-acting sequence elements required for replication by introducing deletions in the infectious clone. We have shown that transcripts derived from cDNA clones lacking the ORF7 gene are not replicated. A more systematic deletion analysis showed that a region of 44 nucleotides between nucleotides 14644 to 14687 in the ORF7 gene was important for replication of RNA of PRRSV. This was an essential interesting finding, since the sequences essential for replication of most positive strand RNA viruses are present in the 5' and 3' noncoding regions. It is also an important finding for studies who's aim is to develop viral replicons which can only be rescued in complementing cell lines expressing the deleted ORFs. The minimal sequence requirements for these RNAs are 5' noncoding region-ORF1a-ORF1b-ORF7-3' noncoding region. Viral RNA s or replicons containing these sequence elements supplemented with a selection of fragments from other PRRSV open reading frames or fragments of open reading frames expressing antigens of other (heterologous) pathogens can be packaged into virus particles when the proteins essential for virus assembly are supplied in trans. When these particles are given to pigs, for example as vaccine, they will enter specific host cells such as macrophages and virus- or heterologous antigens are expressed and induce immune responses because of the replicating RNA. However, since the RNA does not express (all) the proteins required for packaging and the production of new particles, the replicon can not spread further, creating an extremely efficient, but safe and not-spreading recombinant vaccine effective against PRRSV and/or heterologous pathogens.

4. Production of an Attenuated PRRSV Virus by Deletion of the NdeI Site in ORF6.

In this study we have produced a mutant PRRS virus vABV575 that had different growth characteristics in PAMs compared to the parent strain vABV437. Whereas no difference in the expression of structural proteins in BHK-21 cells by RNAs of vABV575 or vABV437 was observed, the vABV575 virus produced in BHK-21 cells infected PAMs slower than vABV437. The growth kinetics of vABV575 need to be analyzed further by performing growth curves in PAMs. In the cDNA clone pABV575, that was used to produce vABV575, the NdeI site at position 14265 in ORF6 was mutated. This resulted in an amino acid change of Thr-59→Asn in the M protein. The mutated M protein was still bound by M-specific MAb 126.3. The M protein is the most conserved structural protein among arteriviruses and coronaviruses. The protein is an integral membrane protein containing three N-terminal hydrophobic membrane spanning domains (Rottier, 1995). The protein spans the membrane three times leaving a short N-terminal domain outside the virion and a short C-terminal domain inside the virion. The M protein of coronaviruses was shown to play an important role in virus assembly (Vennema et al., 1996). The Thr-59→Asn mutation is located between the second and third membrane spanning fragment of M in vABV575. This mutation influences virus assembly, the stability of the virus, or virus entry in the PAMs.

5. Expression of the HA Epitope in Recombinant PRRSV Viruses

In this study we have successfully used PRRSV as a vector for the expression of a foreign antigen, an HA epitope of the haemagglutinin of influenza A virus. Recombinant PRRSV viruses were engineered that produced the HA tag fused to the N- or C-terminus of the N protein. In addition, a PRRSV mutant was created that contained the HA-tag as well as the protease 2A of FMDV fused to the N terminus of the N protein. The protease 2A was functionally active in the context of the PRRSV virus, and cleaved the HA-tag from the N protein. This resulted in an N protein that is identical to the wild type N protein, except for the first and second amino acids (Met and Ala) that are lacking in the mutant. Genetic analysis of passage 4 of the recombinant viruses indicated that the mutant virus containing both the HA-tag and the protease 2A was more stable than the mutant viruses expressing the HA-N-fusion proteins. Apparently, the lack of the first methionine? and mutation of the second amino acid at the N-terminus of N is better tolerated by the virus than the addition of the HA-tag of 9 amino acids to the N- or C-terminus of N. Further genetic and functional analysis needs to be done to explain the differences in stability observed for these viruses. In addition, pigs need to be infected with these HA-expressing mutants to determine whether antibody responses are induced against the HA epitope.

The ORF7 gene was selected for insertion of the HA-tag mainly for two reasons; (I) The subgenomic RNA7 expressing this gene is the most abundant subgenomic RNA produced in infected cells and (II) the HA-tag could be inserted without mutating other ORFs since ORF7 has very little overlap with ORF6 at the 5' end and no overlap with other ORFs at the 3' end. However, similar constructs can be made by introducing the HA-tag and protease 2A at the 5' end of ORF2 and at the 5' end of ORF5 without affecting other ORFs.

The successful expression of the HA-tag in combination with the protease 2A at the 5' end of ORF7 creates new opportunities to express other foreign antigens such as the E2 protein of hog cholera virus, or B cell epitopes of parvo virus by PRRSV. Since PRRSV specifically infects macrophages, cells of the immune system that have antigen presentation and processing capacities, PRRSV might be an excellent vector for the expression of antigens and induction of immunity to these antigens in the pig.

LEGENDS TO THE FIGURES

FIG. 1. Properties of full length cDNA clones of PRRSV containing mutations in the ORF7 gene. The mutated ORF7 genes were inserted in infectious cDNA clone pABV437 with the unique HpaI and PacI site that are indicated. The plasmid (pABV) numbers of the resulting constructs are shown. RNA replication was determined by detecting the expression of structural proteins in IPMA after transfection of the transcripts of the full length cDNA clones in BHK-21 cells. N protein production was determined in IPMA or immunoprecipitation. Production of infectious virus was established by transfer of the supernatant of transfected BHK-21 cells to PAMs and detection of cpe.

FIG. 2. Properties of full length cDNA clones of PRRSV containing deletions in the region encoding the structural proteins of LV in order to elucidate the presence of replication signals in this region. The deleted regions (dotted bars), the regions of ORF7 still present (dark bars) and the plasmid (pABV) numbers of the resulting clones are shown. RNA replication was determined by detecting the expression of structural proteins, and the expression of the N-protein in particular, both in IPMA. Production of infectious virus was established by infecting PAMs with the supernatant of transfected BHK-21 cells. IPMA was performed to detect the expression of LV-proteins.

FIG. 3. Properties of infectious cDNA clone pABV575. This clone was constructed by mutation of the NdeI site at position 14265 in ORF6. RNA replication was determined by detecting the expression of structural proteins in IPMA after transfection of the transcripts of the full length cDNA clones in BHK-21 cells. Production of infectious virus was established by transfer of the supernatant of transfected BHK-21 cells to PAMs and detection of cpe.

FIG. 4. Introduction of an antigenic marker in the infectious clone of PRRSV. The insertion of the HA tag and protease 2A sequence in plasmids pABV 525, 523 and 526 is indicated. RNA replication was determined by detecting the expression of structural proteins in IPMA after transfection of the transcripts of the full length cDNA clones. The expression of N and HA was also determined in IPMA. Production of infectious virus was established by transfer of the supernatant of transfected BHK-21 cells to PAMS and detection of cpe.

REFERENCES

1. Liljeström, P. and Garoff, H. (1991). A new generation of animal cell expression vectors based on the Semliki Forest virus replicon. *Biotechnol.* 9, 1356-1361.
2. Kolodziej, P. A. and Young, R. A. Epitope tagging and protein surveillance. 1991. *Methods Enzymol.* 194, 508-519
3. Meulenberg, J. J. M., Bende, R. J., Pol, J. M., Wensvoort, G., and Moormann, R. J. M. (1995). Nucleocapsid protein N of Lelystad virus: expression by recombinant baculovirus, immunological properties, and suitability for detection of serum antibodies. *Clin. Diagn. Laboratory Immunol.* 2, 652-656.

4. Meulenberg, J. J. M., Hulst, M. M., de Meijer, E. J., Moonen, P. L. J. M., den Besten, A., de Kluyver, E. P., Wensvoort, G., and Moormann, R. J. M. (1993). Lelystad virus, the causative agent of porcine epidemic abortion and respiratory syndrome (PEARS) is related to LDV and EAV. *Virology* 192, 62-74.
5. Meulenberg, J. J. M., and Petersen-den Besten, A. (1996). Identification and characterization of a sixth structural protein of Lelystad virus: The glycoprotein $GP_2$ encoded by ORF2 is incorporated in virus particles. *Virology* 225, 44-51.
6. Meulenberg, J. J. M., Bos-de Ruijter, J. N. A, van de Graaf, R., and Wensvoort, G., and R. J. M. Moormann. (1998) Infectious transcripts from cloned genome-length cDNA of porcine reproductive and respiratory syndrome virus. *J. of Virology* 72, 380-387.
7. Meulenberg, J. J. M., van Nieuwstadt, A. P., van Essen-Zandbergen, A., Bos-de Ruijter, J. N. A., Langeveld, J. P. M., and Meloen, R. H. (1998) Localization and fine mapping of antigenic sites on the nucleocapsid protein N of porcine reproductive and respiratory syndrome virus with monoclonal antibodies. *Virology,* 252, 106-114.
8. Murtaugh, M. P., Elam, M. R., and Kakach, L. T., (1995). Comparison of the structural protein coding sequences of the VR-2332 and Lelystad virus strains of the PRRS virus. *Arch. Virol.* 140, 1451-1460.
9. Percy, N., Barclay, W. S., Garcia-Sastre, A. and Palese, P. Expression of a foreign protein by influenza A virus. 1994. *J. Virol.* 68: 4486-4492
10. Rottier, P. J. M. (1995) The coronavirus membrane protein, p. 115-139. In: S. D. Siddell (ed.), The Coronaviridae. Plenum Press, New York N.Y.
11. Sambrook, J., Fritsch, E. F. and Maniatis, T. Molecular cloning a laboratory manual. 1989. 2nd edition, Cold Spring Harbor Laboratory, Cold Spring Harbor, N.Y.
12. van Nieuwstadt, A. P., Meulenberg, J. J. M., van Essen-Zandbergen, A., Petersen-den Besten, A., Bende, R. J., Moormann, R. J. M., and Wensvoort, G. (1996). Proteins encoded by ORFs 3 and 4 of the genome of Lelystad virus (Arteriviridae) are structural proteins of the virion. *J. Virol.* 70, 4767-4772.
13. Wensvoort, G., Terpstra, C., Pol, J. M. A., Ter Laak, E. A., Bloemraad, M., de Kluyver, E. P., Kragten, C., van Buiten, L., den Besten, A., Wagenaar, F., Broekhuijsen, J. M., Moonen, P. L. J. M., Zetstra, T., de Boer, E. A., Tibben, H. J., de Jong, M. F., van't Veld, P., Groenland, G. J. R., van Gennep, J. A., Voets, M. Th., Verheijden, J. H. M., and Braamskamp, J. (1991). Mystery swine disease in the Netherlands: the isolation of Lelystad virus. *Vet. Quart.* 13, 121-130.
14. Vennema, H., Godeke, G.-J., Rossen, J. W. A., Voorhout, W. F., Horzinek, M. C., Opstelten, D.-J. E., and Rottier, P. J. M. (1996) Nucleocapsid-independent assembly of coronavirus-like patricales by viral envelope protein genes. *EMBO J.* 15, 2020-2028

Wensvoort, G., Terpstra, C., Boonstra, J., Bloemraad, M., and van Zaane, D. (1986). Production of monoclonal antibodies against swine fever virus and their use in laboratory diagnosis. *Vet. Microbiol.* 12, 101-108.

TABLE 1

Primers used in PCR-mutagenesis and sequencing

| Primer (nt.) | Sequence of primer[a] | Sense(+) antisense(-) | Purpose |
|---|---|---|---|
| LV97 | 5' CATTGCAC*CCAG*CAAC*TGG*TTCAGTTG 3' | - | Cys-27→Asn |
| LV100 | 5' CGTCTGG*ATCGATT*GCAAGAGGAGGGA 3' | - | Cys-76→Leu |
| LV188 | 5' TCTGG*ATCGATT*GCAAGCAGAGGGAGCGTTCAGTCT GGGTGAGGTGGTGCCGGATGTCATATTCAGCAG 3' | - | Asp-62→Tyr |
| LV27 | 5' GATTGGATCCAACACATCATTCGAGCTG 3' | + | ΔNdeI |
| LV182 | 5' GGATTGAAAATGCA*ATTAAT*TCATGTAT 3' | - | ΔNdeI |
| 118U250 (14755) | 5' CAGCCAGGGGAAAATGTGGC 3' | - | Sequencing |
| LV37 (14340) | 5' GATTGGATCCACCATGGAGTCATGGAAGTTTATCACT 3' | + | Sequencing |
| LV75 (15088) | 5' TCTAGGAATTCTAGACGATCG 3' | - | Sequencing |
| LV76 (15088) | 5' TCTAGGAATTCTAGACCATCG$(T)_{40}$ 3' | - | RT-PCR |
| LV82 (14703) | 5' AGCAACCTAGGGGAGGACAG 3' | + | Sequencing |
| LV108 (14566) | 5' GGAGTGGTTAACCTCGTCAAGTATGGCCGGTAAAAACCAGAGCC 3' | + | ORF7-HA |
| LV112 (14958) | 5' CCATTCACCTGACTGTTTAATTAACTTGCACCCTGA 3' | - | PacI site |
| LV139 (14609) | 5' AACTTTGACCTTCTCAAGTTGGCCGGCGACGTCGAGTCCA ACCCAGGGCCCGGTAAACCAGAGCCAGAAG 3' | + | $1^{st}$ HA-prot-ORF7 |
| LV140 (14609) | 5' GAGTGGTTAACCTCGTCAAGTATGGCCGGTAAATACCCAT ACGATGTTCCAGATTACGCT AACTTTGACCTTCTC 3' | + | $2^{nd}$ HA-prot-ORF7 |
| LV188 (14687) | 5' ACGTGCGTTAACTAAGGTGCAATGATAAAGTCCCA 3' | + | Δ 99 nt. 5' ORF7 |

TABLE 1-continued

Primers used in PCR-mutagenesis and sequencing

| Primer (nt.) | Sequence of primer[a] | Sense(+) antisense(-) | Purpose |
|---|---|---|---|
| LV189 (14796) | 5' ACGTGCGTTAACTAAATCCGGCACCACCTCACCCA 3' | + | Δ 198 nt. 5' ORF7 |
| LV190 (14885) | 5' ACGTGCGTTAACTAAGGGAAGGTCAGTTTTCAGGT 3' | + | Δ 297 nt. 5' ORF7 |
| LV191 (14936) | 5' ACGTGCGTTAACTAACGCCTCATTCGCGTGACTTC 3' | + | Δ 348 nt. 5' ORF7 |
| LV192 (14609) | 5' AAATACCCATACGATGTTCCAGATTACGCTAACCAGAGCCA 3' | + | 1st HA-ORF7 |
| LV193 (14609) | 5' AGTGGTTAACCTCGTCAAGTATGGCCGGTAAA TACCCATACG 3' | + | 2nd HA-ORF7 |
| LV194 (14971) | 5' ACTGTTTAATTAAGCGTAATCTGGAACATCGTATGGGTAACTTGCACCCTG 3' | - | ORF7-HA |
| LV195 (14642) | 5' ACGTGCGTTAACTAACCGATGGGGAATGGCCAG 3' | + | Δ 55 nt 5' ORF7 |
| LV196 (14642) | 5' GGAGTGGTTAACCTCGTCAAGTAACCGATGGGGAATGGCCAG 3' | + | Δ 45 nt 5' ORF7 |
| LV197 (14597) | 5' ACGTGCGTTAACGGCCGGTAAAAACCAGAGC 3' | + | Δ 10 nt 3' ORF6 |
| LV198 (141333) | 5' GCTCGTGCTAGCCTTTAGCATCACATACAC 3' | + | Δ 54 nt 3' ORF6 |
| LV199 (14596) | 5' CTTGACGAGGTTAACTGGTACTAGAGTGCC 3' | - | Δ 54 nt 3' ORF6 |

[a]Restriction sites are underlined, inserted foreign sequences are boxed (HA: line; protease: dotted line)

TABLE 2

Staining of LV4.2.1, vABV600 (Asp-62→Tyr mutation), ATCCVR2332-like PRRSV containing an Asp61→ Tyr mutation in the N protein, and ATCC-VR2332 with various N-specific MAbs in IPMA

| MAb | Site | LV4.2.1 | vABV600 (Asp-62→ Tyr) | ATCCVR2332-like (Asp61→ Tyr) | ATCC-VR2332 |
|---|---|---|---|---|---|
| 138.22 | A | + | + | – | – |
| NS99 | B | + | + | + | + |
| 122.17 | D | ++ | ++ | ++ | ++ |
| 130.2 | D | ++ | –[1)] | – | + |
| 130.4 | D | ++ | –[1)] | – | + |
| 131.7 | D | ++ | –[1)] | – | + |
| 131.9 | D | ++ | –[1)] | – | + |
| SDOW17 | D | ++ | –[1)] | –[1)] | ++ |
| WBE1 | D | + | – | – | – |
| WBE4 | D | ++ | ++ | – | – |
| WBE5 | D | ++ | ++ | – | – |
| WBE6 | D | ++ | ++ | – | – |
| VO17 | ? | – | – | + | + |

[1)]No staining in IPMA with hybridoma culture supernatant diluted to 0.3-0.5 μg/ml, but faint staining with IgG purified from the culture supernatant diluted to 10 μg/ml.

The invention claimed is:

1. A vector comprising a replicon of Porcine Reproductive and Respiratory Virus (PRRSV) capable of in vivo replication, the replicon comprises (i) the 5' noncoding region;

(ii) the ORF1a and ORF1b;

(iii) a replicon-ORF7 comprising a fragment of the ORF7 encoding nucleotides of a PRRSV, wherein the fragment comprises the region of the ORF7 that comprises ORF7 nucleotides 14642 to 14686 as identified in the nucleic acid sequence of the Lelystad virus isolate of PRRSV or an ORF7 encoding sequence from another PRRSV genome that aligns with nucleotides 14642 to 14686 of Lelystad virus and does not encode the complete ORF7 of said PRRS and (iv) the 3' non-coding region, but no sequence corresponding to one or more of ORF2, ORF3, ORF4, ORF5 and ORF6 sequence of PRRSV.

2. The vector of claim 1, further comprising nucleic acid derived from at least one heterologous microorganism.

3. The vector of claim 1 wherein the replicon-ORF7 further comprises a mutation rendering the nucleocapsid protein N incapable of forming a proper capsid.

4. The vector of claim 3 wherein the replicon-ORF7 further comprises a nucleic acid modification, whereby a cysteine in the nucleocapsid protein N is substituted or deleted.

5. The vector of claim 1, further comprising a marker allowing serological discrimination.

6. The vector of claim 5 wherein the marker comprises a nucleic acid modification, whereby Asp-62 in nucleocapsid protein N is substituted or deleted.

7. The vector of claim 1, further comprising a nucleic acid modification in a virulence marker of PRRSV.

8. The vector of claim 1, wherein the replicon ORF-7 further comprises a nucleic acid modification leading to an amino acid change in an antigenic region of the nucleocapsid protein N, whereby the replicon is antigenically different from Lelystad isolate PRRSV or North American PRRSV.

9. The vector of claim 8 wherein the antigenic region comprises amino acids selected from the group consisting of amino acids 25 to 30 of the nucleocapsid protein N (SEQ ID NO:1), amino acids 80 to 90 of the nucleocapsid protein N (SEQ ID NO:3), and combinations thereof.

10. A vaccine comprising the vector of claim 1.

11. The vaccine of claim 10, wherein the replicon-ORF7 further comprises a mutation leading to the nucleocapsid protein N incapable of forming a proper capsid.

12. The vaccine of claim 10, further comprising a marker allowing serological discrimination.

13. The vaccine of claim 10 further comprising a nucleic acid modification in a virulence marker of PRRSV.

14. A method of vaccinating pigs comprising administering to a pig a vaccine of claim 10.

* * * * *